(12) United States Patent
Corbin, III et al.

(10) Patent No.: US 10,976,105 B2
(45) Date of Patent: Apr. 13, 2021

(54) LYOPHILIZATION

(71) Applicant: Terumo BCT, Inc., Lakewood, CO (US)

(72) Inventors: Frank Corbin, III, Littleton, CO (US); Dennis J. Hlavinka, Arvada, CO (US); Rajesh Pareta, Lakewood, CO (US); Mark E. Hillam, Wheat Ridge, CO (US)

(73) Assignee: Terumo BCT, Inc., Lakewood, CO (US)

( * ) Notice: Subject to any disclaimer, the term of this patent is extended or adjusted under 35 U.S.C. 154(b) by 0 days.

(21) Appl. No.: 16/736,430

(22) Filed: Jan. 7, 2020

(65) Prior Publication Data

US 2020/0141646 A1    May 7, 2020

Related U.S. Application Data

(62) Division of application No. 15/863,390, filed on Jan. 5, 2018, now Pat. No. 10,539,367, which is a division
(Continued)

(51) Int. Cl.
*F26B 5/06* (2006.01)
*A61J 1/14* (2006.01)
(Continued)

(52) U.S. Cl.
CPC .............. *F26B 5/06* (2013.01); *A01N 1/0252* (2013.01); *A01N 1/0263* (2013.01);
(Continued)

(58) Field of Classification Search
CPC ...... F26B 5/06; A61M 1/0286; A61M 1/0209; A61M 1/0272; A61M 2202/0415; A61J 1/1468; A61J 1/10; A61J 1/14; A61J 1/1475; A01N 1/0252; A01N 1/0263; A01N 1/0284; A01N 1/0289; A61L 2/084; A61L 2/2085; A61L 2/088; A61L 2/10; A61L 2202/22
(Continued)

(56) References Cited

U.S. PATENT DOCUMENTS 1,441,570 A    1/1923    Fitzgerald
1,504,225 A    8/1924    Fitzgerald
(Continued)

FOREIGN PATENT DOCUMENTS

CN    203572189 U    4/2014
DE    19729778 A1    1/1999
(Continued)

OTHER PUBLICATIONS

US 8,359,766 B2, 01/2013, Hubbard, Jr. et al. (withdrawn)
(Continued)

*Primary Examiner* — Stephen M Gravini
(74) *Attorney, Agent, or Firm* — Terumo BCT, Inc. IP Law Department

(57) ABSTRACT

Embodiments of methods, systems, and apparatuses for lyophilizing, storing, and transfusing materials are described. In embodiments, the materials may include whole blood or a component of whole blood such as plasma.

3 Claims, 24 Drawing Sheets

Related U.S. Application Data of application No. 14/734,832, filed on Jun. 9, 2015, now Pat. No. 9,863,699.

(60) Provisional application No. 62/009,629, filed on Jun. 9, 2014, provisional application No. 62/010,027, filed on Jun. 10, 2014, provisional application No. 62/142,146, filed on Apr. 2, 2015.

(51) Int. Cl.
*A61L 2/08* (2006.01)
*A61M 1/02* (2006.01)
*A01N 1/02* (2006.01)
*A61L 2/10* (2006.01)
*A61J 1/10* (2006.01)

(52) U.S. Cl.
CPC ......... *A01N 1/0284* (2013.01); *A01N 1/0289* (2013.01); *A61J 1/10* (2013.01); *A61J 1/14* (2013.01); *A61J 1/1468* (2015.05); *A61J 1/1475* (2013.01); *A61L 2/084* (2013.01); *A61L 2/085* (2013.01); *A61L 2/088* (2013.01); *A61L 2/10* (2013.01); *A61M 1/0209* (2013.01); *A61M 1/0272* (2013.01); *A61M 1/0286* (2014.02); *A61L 2202/22* (2013.01); *A61M 2202/0415* (2013.01)

(58) Field of Classification Search
USPC ............................................ 34/92, 284, 287
See application file for complete search history.

(56) References Cited

U.S. PATENT DOCUMENTS

| | | | |
|---|---|---|---|
| 2,767,117 | A | 10/1956 | Crawley |
| 3,375,824 | A | 4/1968 | Krakauer et al. |
| 3,466,249 | A | 9/1969 | Anderson |
| 3,537,189 | A | 11/1970 | Bender et al. |
| 3,571,940 | A | 3/1971 | Bender |
| 3,607,858 | A | 9/1971 | Querry et al. |
| 3,945,523 | A | 3/1976 | Wertlake et al. |
| 3,964,865 | A | 6/1976 | Das |
| 4,001,944 | A | 1/1977 | Williams |
| 4,056,484 | A | 11/1977 | Heimburger et al. |
| 4,134,943 | A | 1/1979 | Knitsch et al. |
| 4,218,321 | A | 8/1980 | Sasaki et al. |
| 4,650,678 | A | 3/1987 | Fuhge et al. |
| 4,730,460 | A | 3/1988 | Coelho et al. |
| 4,874,690 | A | 10/1989 | Goodrich, Jr. et al. |
| 4,904,641 | A | 2/1990 | Eibl et al. |
| 4,973,327 | A | 11/1990 | Goodrich, Jr. et al. |
| 5,043,261 | A | 8/1991 | Goodrich et al. |
| 5,045,446 | A | 9/1991 | Goodrich, Jr. et al. |
| 5,171,661 | A | 12/1992 | Goodrich, Jr. et al. |
| 5,178,884 | A | 1/1993 | Goodrich et al. |
| 5,213,814 | A | 5/1993 | Goodrich, Jr. et al. |
| 5,257,983 | A | 11/1993 | Garyantes et al. |
| 5,340,592 | A | 8/1994 | Goodrich, Jr. et al. |
| 5,425,951 | A | 6/1995 | Goodrich, Jr. et al. |
| 5,552,320 | A * | 9/1996 | Smith ................. A61L 2/28 435/287.4 |
| 5,648,206 | A | 7/1997 | Goodrich, Jr. et al. |
| 5,656,498 | A | 8/1997 | Iijima et al. |
| 5,759,774 | A | 6/1998 | Hackett et al. |
| 5,849,473 | A | 12/1998 | Cabrera et al. |
| 6,132,454 | A | 10/2000 | Fellows |
| 6,148,536 | A | 11/2000 | Iijima |
| 6,221,575 | B1 | 4/2001 | Roser et al. |
| 6,517,526 | B1 | 2/2003 | Tamari |
| 6,608,237 | B1 | 8/2003 | Li et al. |
| 6,645,180 | B1 * | 11/2003 | Hatch ................. A61M 5/282 604/181 |
| 6,773,425 | B1 | 8/2004 | Tamari |
| 6,869,901 | B2 | 3/2005 | Lubker, II |
| 7,179,951 | B2 | 2/2007 | Krishnaswamy-Mirle et al. |
| 7,249,880 | B2 | 7/2007 | Zambaux |
| 7,370,436 | B2 * | 5/2008 | Auer .................. A23L 3/44 34/284 |
| 7,422,726 | B2 | 9/2008 | Hammerstedt et al. |
| 7,776,022 | B2 | 8/2010 | McCarthy et al. |
| 7,931,919 | B2 | 4/2011 | Bakaltcheva et al. |
| 8,053,248 | B2 | 11/2011 | Bakaltcheva et al. |
| 8,057,872 | B2 | 11/2011 | Chen |
| 8,097,403 | B2 | 1/2012 | Ho et al. |
| 8,372,343 | B2 | 2/2013 | Goldstein |
| 8,449,520 | B2 | 5/2013 | Pepper et al. |
| 8,491,178 | B2 | 7/2013 | Breidenthal et al. |
| 8,492,081 | B2 | 7/2013 | Nichols et al. |
| 8,516,714 | B2 | 8/2013 | Biemans et al. |
| 8,518,452 | B2 | 8/2013 | Bjornstrup et al. |
| 9,046,303 | B2 | 6/2015 | Yagi |
| 9,161,527 | B2 | 10/2015 | Cutting et al. |
| 9,540,416 | B2 * | 1/2017 | Diaz Garcia ........... A61P 37/04 |
| 9,561,893 | B2 | 2/2017 | Root et al. |
| 9,863,699 | B2 * | 1/2018 | Corbin, III ........... A01N 1/0252 |
| 10,539,367 | B2 * | 1/2020 | Corbin, III ........... A61J 1/14 |
| 2002/0035354 | A1 | 3/2002 | Mirle et al. |
| 2003/0014017 | A1 * | 1/2003 | Hatch ................. A61M 5/282 604/181 |
| 2004/0081588 | A1 | 4/2004 | Hammerstedt et al. |
| 2006/0216687 | A1 | 9/2006 | Alves-Filho et al. |
| 2006/0263759 | A1 | 11/2006 | Alves-Filho et al. |
| 2008/0119818 | A1 | 5/2008 | Bakaltcheva et al. |
| 2008/0206293 | A1 | 8/2008 | Toreki et al. |
| 2008/0234654 | A1 | 9/2008 | McCarthy et al. |
| 2008/0299538 | A1 | 12/2008 | Goodrich et al. |
| 2009/0107001 | A1 | 4/2009 | McCarthy |
| 2009/0113753 | A1 | 5/2009 | Pepper et al. |
| 2009/0223080 | A1 | 9/2009 | McCarthy et al. |
| 2009/0324929 | A1 | 12/2009 | Yamakawa et al. |
| 2010/0049156 | A1 | 2/2010 | Dickhorner et al. |
| 2010/0273141 | A1 | 10/2010 | Bakaltcheva et al. |
| 2011/0114524 | A1 | 5/2011 | Eibl |
| 2011/0183311 | A1 | 7/2011 | Ho et al. |
| 2011/0282325 | A1 | 11/2011 | Gregory |
| 2012/0231485 | A1 | 9/2012 | Önundarson et al. |
| 2013/0143198 | A1 | 6/2013 | Sailliol |
| 2013/0326899 | A1 | 12/2013 | Yagi |
| 2014/0287643 | A1 | 9/2014 | Nozaki et al. |
| 2015/0158652 | A1 | 6/2015 | Root et al. |
| 2015/0354894 | A1 * | 12/2015 | Corbin, III ........... A61L 2/084 34/296 |
| 2016/0375184 | A1 | 12/2016 | Albert et al. |
| 2018/0128544 | A1 * | 5/2018 | Corbin, III ........... A01N 1/0284 |
| 2020/0141646 | A1 * | 5/2020 | Corbin, III ........... A01N 1/0289 |

FOREIGN PATENT DOCUMENTS

| | | | |
|---|---|---|---|
| EP | 1087990 B1 | 9/2004 | |
| EP | 1958618 A1 | 8/2008 | |
| EP | 1407780 B1 | 5/2013 | |
| EP | 2877479 B1 * | 11/2018 | ........... C07H 15/256 |
| GB | 450146 A | 7/1936 | |
| GB | 748784 A | 5/1956 | |
| GB | 814491 A | 6/1959 | |
| GB | 1486787 A | 9/1977 | |
| GB | 1497517 | 1/1978 | |
| JP | H63-036828 A | 2/1988 | |
| JP | 6360830 B2 * | 7/2018 | ........... C07H 15/256 |
| WO | 96/29556 A1 | 9/1996 | |
| WO | 96/31748 A1 | 10/1996 | |
| WO | WO-0222191 A2 * | 3/2002 | ............ A61M 5/282 |
| WO | WO-0222191 A3 * | 9/2003 | ............ A61M 5/282 |
| WO | 2005089816 A1 | 9/2005 | |
| WO | 2006028648 A2 | 3/2006 | |
| WO | 2006028648 A3 | 1/2007 | |
| WO | 2007104760 A2 | 9/2007 | |
| WO | 2008115548 A2 | 9/2008 | |
| WO | 2010019217 A1 | 2/2010 | |
| WO | 2010033169 A1 | 3/2010 | |
| WO | 2010093429 A1 | 8/2010 | |
| WO | 2013062479 A1 | 5/2013 | |
| WO | WO-2014016374 A1 * | 1/2014 | ............... C07H 1/08 |

(56) References Cited

FOREIGN PATENT DOCUMENTS

| WO | 2014033228 A1 | 3/2014 |
| WO | 2015191599 A2 | 12/2015 |
| WO | 2015191599 A3 | 4/2016 |

OTHER PUBLICATIONS

Cherry, Chris, "Containment systems for freeze-drying," ISL-FD, Sep. 7, 2015.
Cherry, Christopher Lee Albert, "Development of Novel Containment Systems for Freeze-Drying," a thesis submitted to Cardiff Metropolitan University, Apr. 10, 2013.
Communication under Rule 94(3) EPC, European Patent Application No. 15731441.4, dated Aug. 29, 2018.
Communication under Rule 164(2)(a) EPC, European Patent Application No. 15731441.4, dated Sep. 26, 2018.
Communication pursuant to Rule 164(2)(b) and Article 94(3) EPC, European Patent Application No. 15731441.4, dated Feb. 14, 2019.
Invitation to Pay Additional Fees and Partial International Search, PCT/US2015/034927, dated Sep. 9, 2015.
International Search Report and Written Opinion, PCT/US2015/034927, dated Feb. 16, 2016.
International Preliminary Report on Patentability, PCT/US2015/034927, dated Dec. 22, 2016.
Pan et al, "Study of Banana Dehydration Using Sequential Infrared Radiation Heating and Freeze-Drying", LWT—Food Science and Technology, 2008 v. 41, pp. 1944-1951.
Pisano et al. "Heat Transfer in Freeze-Drying Apparatus", Developments in Heat Transfer, edited by Dr. Marco Aurelio Dos Santos Bernardes, In Tech, Sep. 15, 2011, pp. 91-114.

* cited by examiner

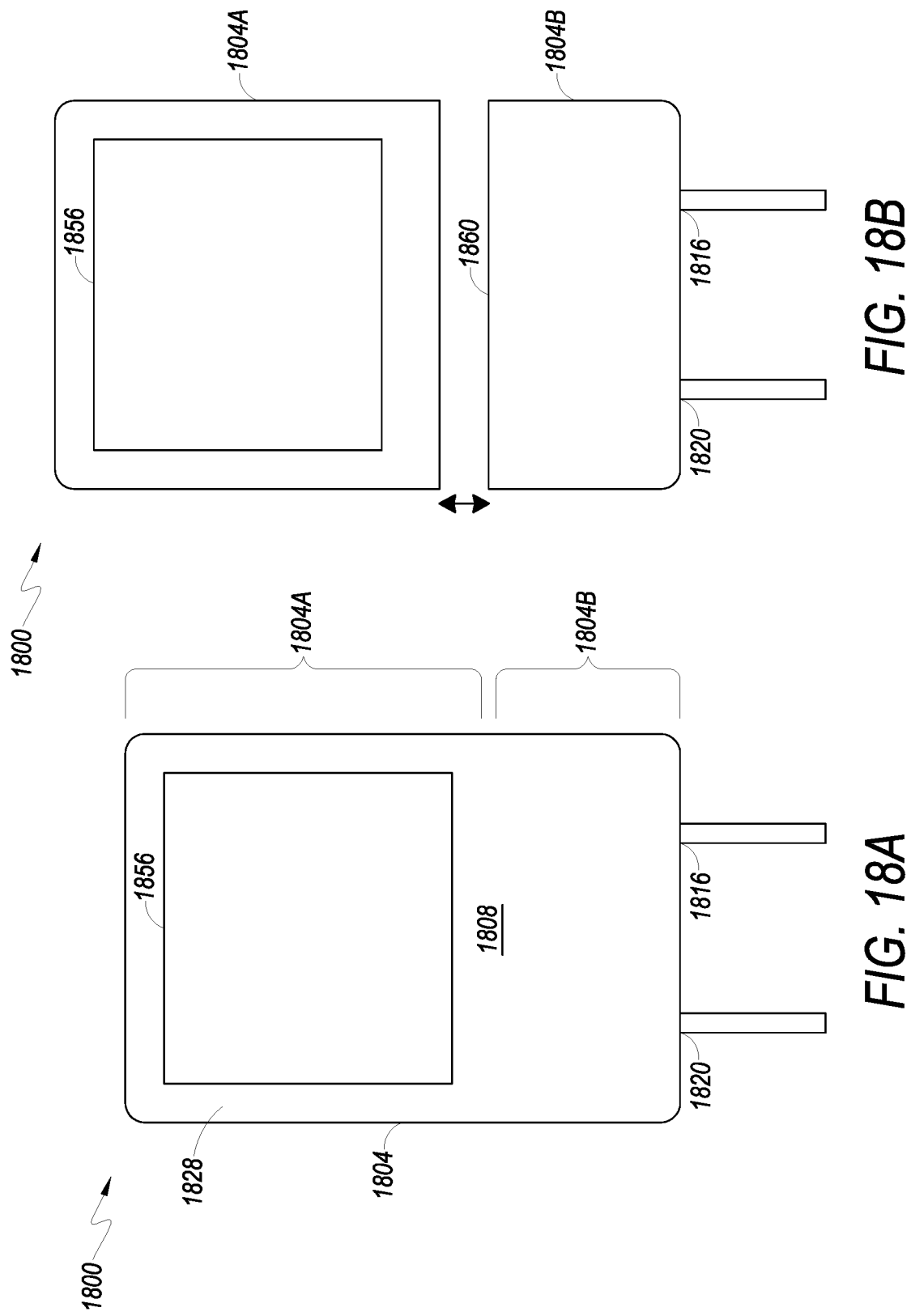

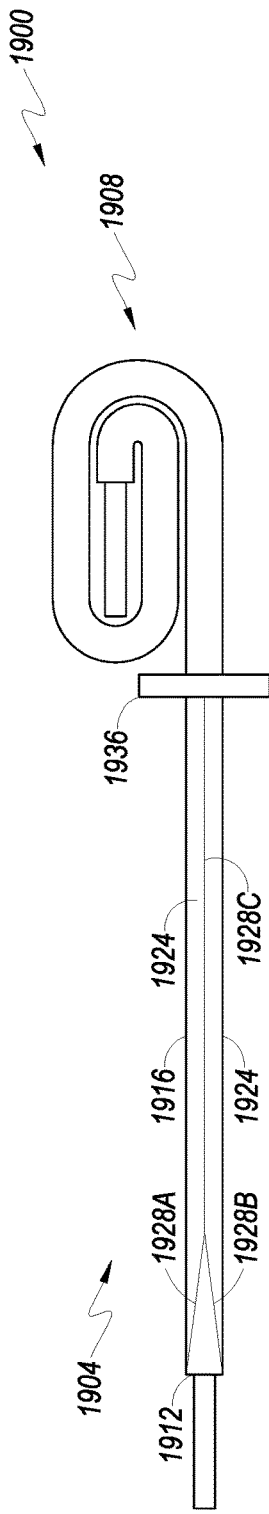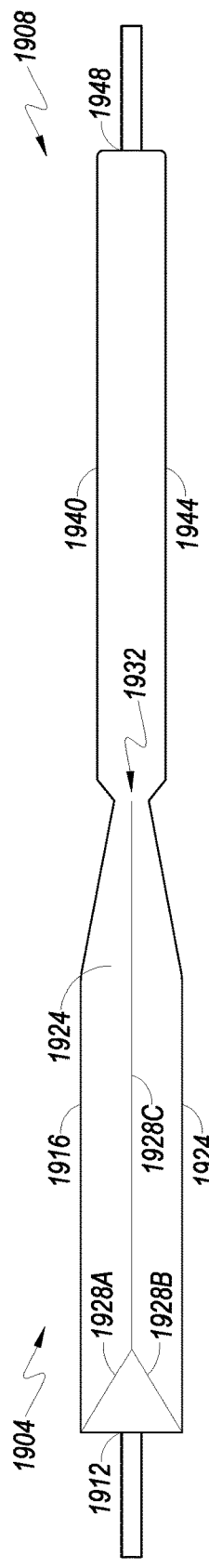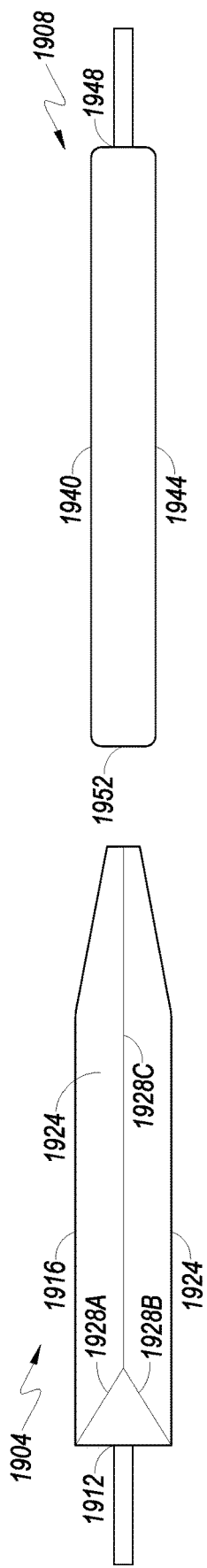

LYOPHILIZATION

CROSS-REFERENCE TO RELATED PATENT APPLICATION(S)

This patent application is a divisional application of and claims priority to, U.S. patent application Ser. No. 15/863,390, entitled LYOPHILIZATION, filed on Jan. 5, 2018 and, which is a divisional application of, and claims priority to, U.S. patent application Ser. No. 14/734,832, entitled LYOPHILIZATION, filed on Jun. 9, 2015 and issued as U.S. Pat. No. 9,863,699 on Jan. 9, 2018. U.S. patent application Ser. No. 14/734,832 claims priority to: U.S. Provisional Patent Application No. 62/009,629, filed Jun. 9, 2014, entitled LYOPHILIZATION; U.S. Provisional Patent Application No. 62/010,027, filed Jun. 10, 2014, entitled LYOPHILIZATION; and U.S. Provisional Patent Application No. 62/142,146 filed Apr. 2, 2015, entitled CONTAINER FOR LYOPHILIZATION. U.S. patent application Ser. No. 15/863,390, U.S. patent application Ser. No. 14/734,832 and all three of the above-identified provisional patent applications are hereby incorporated by reference in their entirety as if set forth herein in full.

BACKGROUND

Lyophilization is a process that is used to preserve materials and increase their shelf life, including biological materials, food, and pharmaceuticals. Lyophilization occurs by first freezing material to solidify it and then subjecting the material to a low pressure environment (below atmospheric pressure) to allow for sublimation of a component of the material. Typically the component is a liquid at standard temperature and pressure, one example being water.

Depending on the type of material and volume being lyophilized, the process may take several days to complete. There is a need to improve the efficiency and shorten the time to lyophilize material without affecting the ability to later use the final lyophilized product.

Embodiments of the present invention have been made in light of these and other considerations. However, the relatively specific problems discussed above do not limit the applicability of the embodiments of the present invention.

SUMMARY

The summary is provided to introduce aspects of some embodiments of the present invention in a simplified form, and is not intended to identify key or essential elements of the claimed invention, nor is it intended to limit the scope of the claims.

Some embodiments relate to containers for lyophilizing, storing, and transfusing a blood component. The containers may include, in embodiments, a first wall comprising a flexible polymeric material and a second wall attached to the first wall to define an interior volume of the container. The second wall in embodiments is made from a gas permeable material that allows gas to move from an interior of the container to an exterior. In some embodiments, the containers may include a second chamber (or portion), where the lyophilized material is stored after processing.

Other embodiments relate to methods of lyophilizing a multi-component liquid. In embodiments, the methods may involve maintaining the multi-component liquid in a container and subjecting the multi-component liquid to a first pressure, which may be below atmospheric pressure. At least one component of the multi-component liquid may then be evaporated for a predetermined time. After the evaporation step, the multi-component liquid may be frozen to form a solid. In some embodiments, the multi-component liquid may be subjected to shaping, e.g., pressing with a compressive force, during the freezing step. The solid may then be subjected to a second pressure that in embodiments is lower than the first pressure. A portion of the solid may then be sublimated. A component of the solid may then be desorbed from the solid.

Yet other embodiments relate to a system for lyophilizing a multi-component liquid. Embodiments of the system may include a first plate with a first surface and a second plate with a second surface opposed to the first surface. The second plate may include channels for circulating a fluid. The system may also include a plate moving system that is operable to increase and decrease a space between the first surface and the second surface. In some embodiments, the first plate may include a second layer that forms the first surface. The second layer may in some embodiments be an infrared radiator for adding energy to materials that are being lyophilized.

BRIEF DESCRIPTION OF THE DRAWINGS

Non-limiting and non-exhaustive embodiments are described with reference to the following figures.

FIGS. 18A and 18B illustrate a container that may be used to store material for lyophilization and after lyophilization according to other embodiments.

FIGS. 19A-19C illustrate a container that may be used to store material for lyophilization and after lyophilization according to other embodiments.

DETAILED DESCRIPTION

Figure 1:
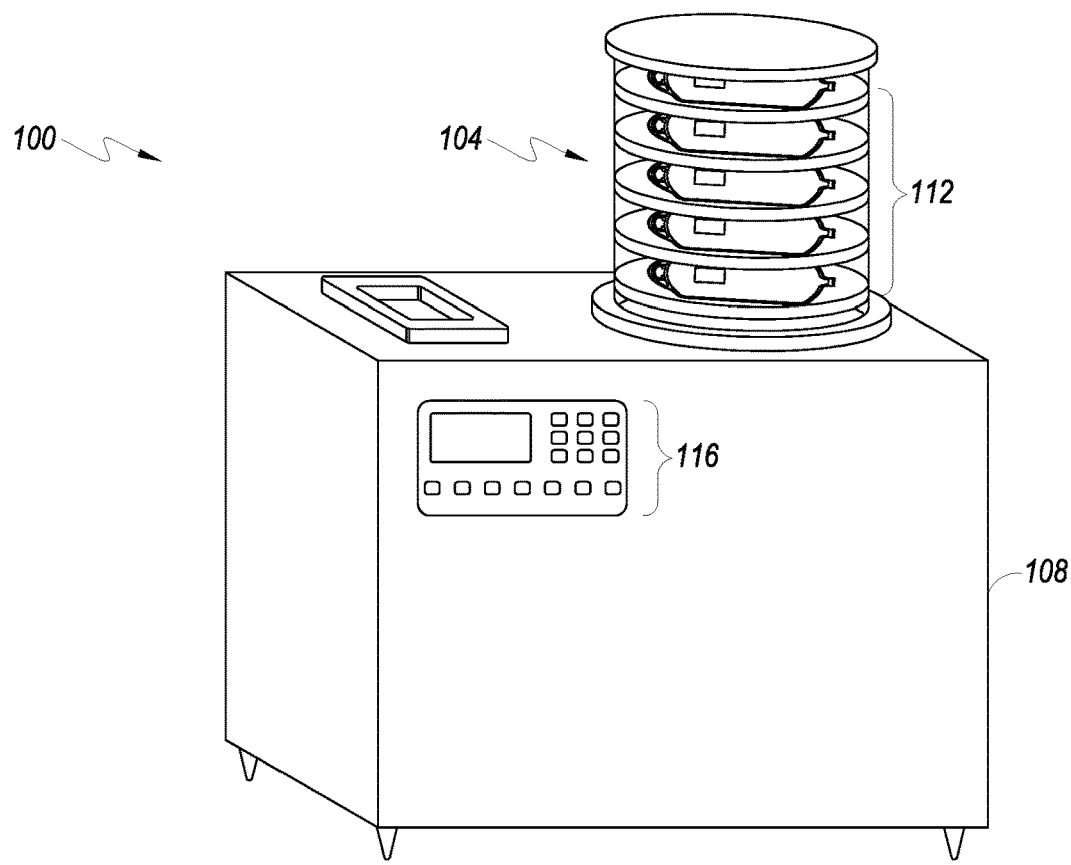
FIG. 1 illustrates a first embodiment of an apparatus for lyophilizing materials.

The principles of the present invention may be further understood by reference to the following detailed description and the embodiments depicted in the accompanying drawings. It should be understood that although specific features are shown and described below with respect to detailed embodiments, the present invention is not limited to the embodiments described below.

Reference will now be made in detail to the embodiments illustrated in the accompanying drawings and described below. Wherever possible, the same reference numbers are used in the drawings and the description to refer to the same or like parts.

FIG. 1 illustrates a first embodiment of an apparatus 100 for lyophilizing materials (e.g., in the form of liquids, solids, or combinations thereof) according to embodiments. As shown in FIG. 1, apparatus 100 includes a chamber 104, a housing 108, a shelf system 112, and an interface 116. Housing 108 houses, among other components, a vacuum system for creating a low pressure (e.g., below atmospheric pressure) environment in chamber 104, a temperature control system for controlling the temperature of the shelf system 112, and a control system, which may include a computer system (with one or more processors) for controlling various functions of the apparatus 100. User interface 116 can be used by an operator to input data, parameters, and other information to control the functions of apparatus 100. In one embodiment, user interface 116 may allow an operator to create and run custom processes for lyophilizing material, including multi-step programmable cycles.

In embodiments, material to be lyophilized is placed on the shelf system 112 in chamber 104. The vacuum system may then bring the environment in chamber 104 to a first pressure, which may be a pressure below atmospheric pressure. In some embodiments, the first pressure may be selected based on evaporation, while in a liquid state, of a component in the material to be lyophilized. After the chamber 104 has reached the first pressure, at least a portion of the first component may be evaporated from the material. Evaporation may be performed for a first period of time, or until a predetermined amount of the first component has been evaporated away from the material.

After the portion of the first component has been evaporated, the remaining material may be cooled to freeze any remaining liquid into a solid. In embodiments, the evaporation described above may be part of the freezing step. As can be appreciated, in some embodiments, the evaporation may cool off the remaining material to such an extent that liquid freezes into a solid. In other embodiments, the freezing may involve cooling using other mechanisms in addition to, or in lieu of, evaporation.

The vacuum system may bring the environment in chamber 104 to a second pressure, which in embodiments may be lower than the first pressure. Under the second pressure, a second portion of the first component may be sublimated from the material. In some embodiments, the sublimation may also include sublimating other components of the material.

In some embodiments, after sublimation, the material may be maintained at the second pressure for an additional period of time to desorb one or more components from the material. The component that is desorbed may be previously absorbed or adsorbed by the material.

As described in greater detail below, in embodiments, the shelf system 112 may include features that transfer/add energy to, or remove energy from, the material being lyophilized. The addition or removal of energy may be used in one or more of the steps described above. For example, the shelf system 112 may be used to add energy to the material to effect the evaporation of the component from the material. The shelf system 112 may also be used to remove energy of the system to cool the material and freeze any liquid in the material into a solid. The shelf system 112 may also be used, in embodiments, to add energy to the material during the sublimation step.

Figure 2:
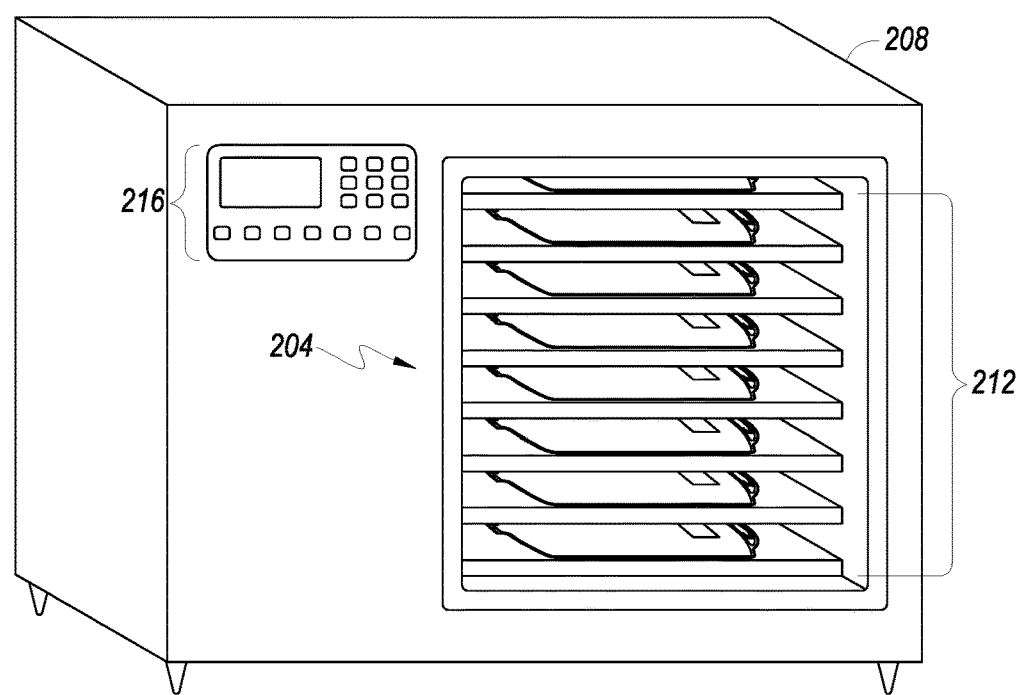
FIG. 2 illustrates a second embodiment of an apparatus for lyophilizing materials.

FIG. 2 illustrates a second embodiment of an apparatus 200 for lyophilizing materials according to embodiments. Apparatus 200 has similar features as apparatus 100 including a chamber 204 that is housed within housing 208. Apparatus 200 also includes a shelf system 212 and a user interface 216. Apparatus 200 may, in embodiments, provide similar functionality and operate similarly as apparatus 100. It is noted that apparatus 100 and apparatus 200 are shown and described merely to illustrate that embodiments may be implemented in any lyophilization apparatus or system and are not limited to any particular design or arrangement of system components.

Below various structures may be described as being part of embodiments of a lyophilization apparatus or system, e.g., apparatus 100 or apparatus 200. However, the present invention is not limited thereto. Various steps of a lyophilization process may be performed by different structures, apparatuses, or systems. As one non-limiting example, the evaporation step, the freezing step, and the sublimation step (described above) may, in some embodiments, be performed by three separate apparatuses each performing a single step. In other embodiments, one or more apparatuses may have various functionalities allowing more than one step of a lyophilization process to be performed in one apparatus.

As one example, an evaporation step may be performed in an apparatus that also performs a freezing step. As described below with respect to FIG. 29, evaporation may cool material during a freezing step. After the evaporation and freezing, the material may be transferred to an apparatus that sublimates a component of the material.

In some embodiments, an apparatus may be used to evaporate a liquid component from a material in a first apparatus. The material may then be transferred to a second apparatus where the material is frozen. After freezing, the material may be returned to the first apparatus for lyophilization.

In other embodiments, an evaporation step may not be performed as part of a process. Material may be frozen in one apparatus and then the material may be transferred to a second apparatus for sublimation. As the embodiments described above illustrate, the present invention is not limited to performing a process on any one apparatus but may involve steps performed on multiple apparatuses.

Figure 3:
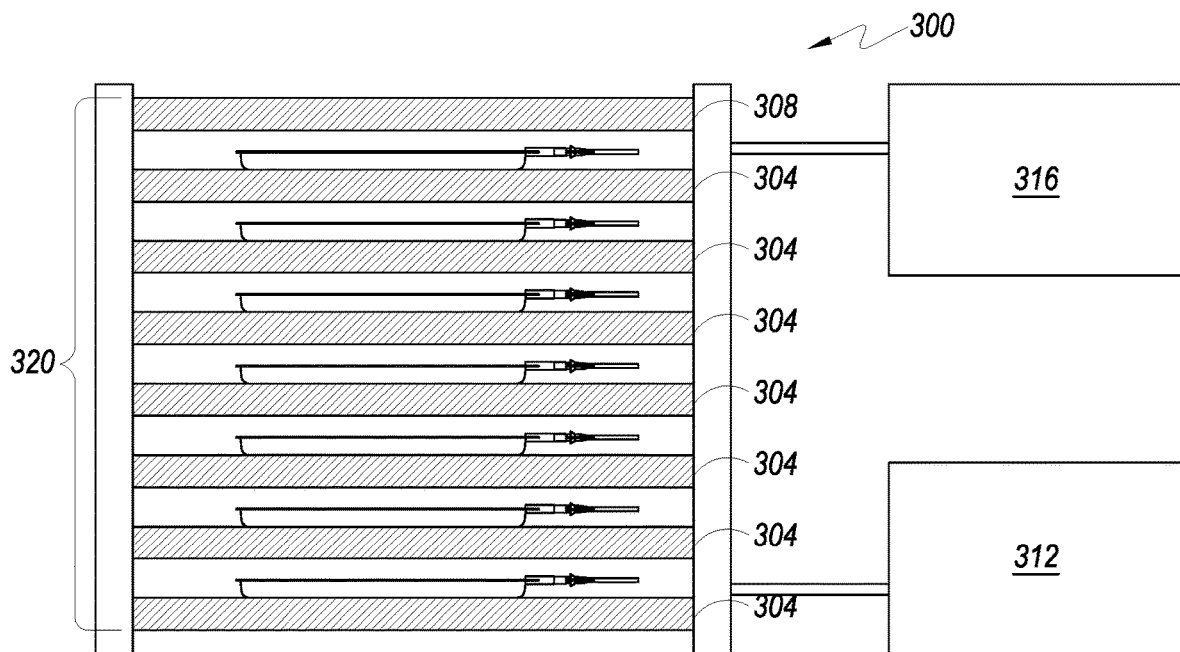
FIG. 3 illustrates an embodiment of a shelf system.

FIG. 3 illustrates an embodiment of a shelf system 300 that may be used in a lyophilization process/apparatus for example apparatus 100 or apparatus 200 described above. Shelf system 300 includes plates 304 that make up shelves 320 and provide a surface for placing material to be lyophilized. Depending on the type of material to be lyophilized, the material may be maintained within a container such as a tray, bag, or bottle and the container placed on the plates 304. FIG. 3 illustrates containers on the plates 304. The containers store material to be lyophilized. Shelf system 300 also includes an end plate 308, which in embodiments may be stationary as described in greater detail below.

Additionally, shelf system 300 also includes a movement control system 312 that may be used in embodiments to change the distance between plates 304. As described in detail below, the distance between plates 304 can be changed so that materials to be lyophilized may be shaped by being pressed, during a freezing step of a lyophilization process. The movement control system 312 may be designed, in embodiments, to move plates 304 toward, and away from, each other.

Figure 4:
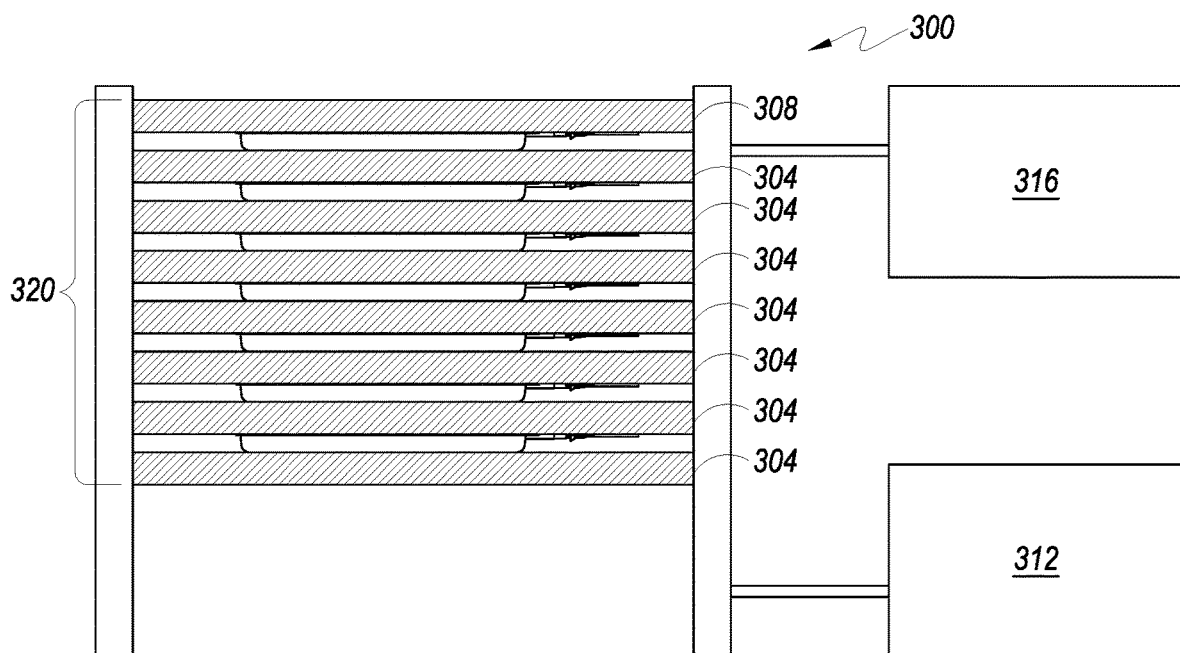
FIG. 4 illustrates the shelf system of FIG. 3 with the plates having been moved as compared to FIG. 3.

FIG. 4 illustrates shelf system 300 with plates 304 moved, e.g., in a fully collapsed position, to compress material during a lyophilization process, and in particular during a freezing step of a lyophilization process. As shown in FIG. 4, end plate 308 remains in the same position as is shown in FIG. 3, however each of plates 304 have moved up, with the first plate (right below end plate 308) having moved the least amount and the seventh plate (furthest away from end plate 308) having moved the most amount. In the collapsed position shown in FIG. 4, pressure is applied to each of the containers on the plates 304 to press the containers and the material. In other words, a compressive force is applied to the container and material within the container. As described in greater detail below, it is believed that the application of pressure, e.g., pressing a container, may provide some benefit to the process of lyophilization and is used in some embodiments.

As may be appreciated, the movement control system 312 may include a number of different components that are used to move plates 304. For example, movement control system 312 may include, in embodiments, computer system(s), such as controllers, that include processor(s), memory, input devices, output devices, communication devices, or any combination thereof. Movement control system 312 may also include other subsystems such as hydraulic, pneumatic, or mechanical systems that may include one or more motors, actuators, pumps, compressors, cylinders, pistons, tubing, valves, bladders, sensors, regulators, or any combination thereof.

System 300 also includes a thermal fluid system 316. The thermal fluid system 316 circulates a thermal fluid through at least a portion of shelves 320 to control the temperature of at least some of the plates 304 and consequently material that is position on the plates 304 for lyophilization. Thermal fluid system 316 may be used in removing or adding energy to plates 304 of shelves 320, during various steps of a lyophilization process.

Figure 5:
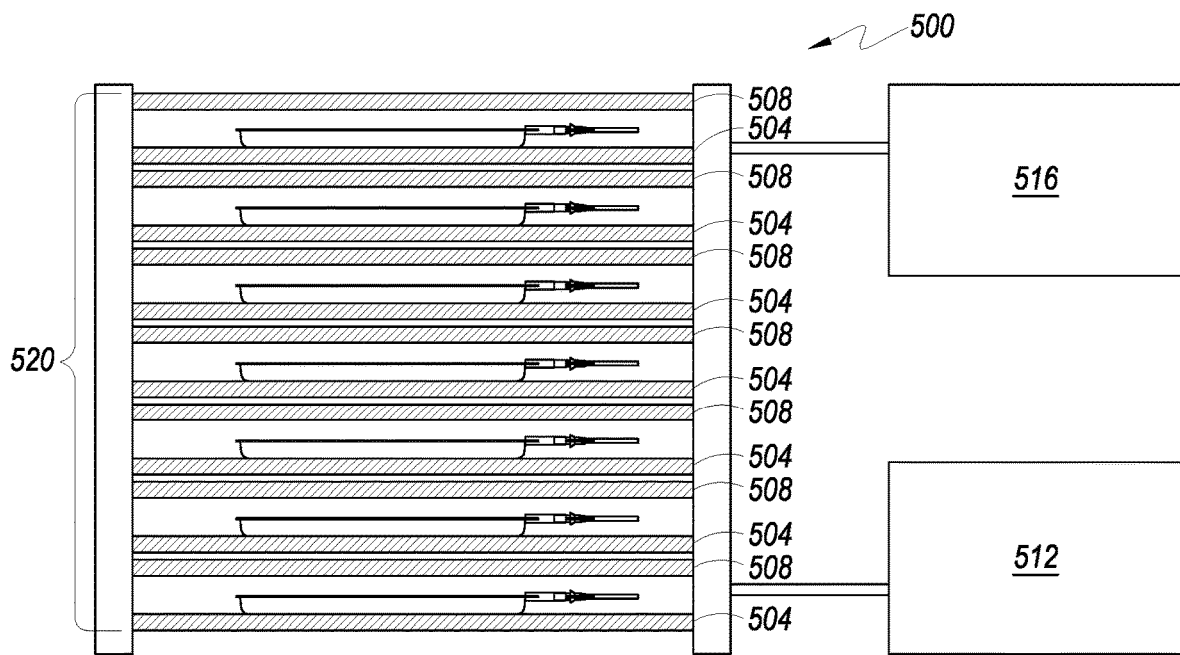
FIG. 5 illustrates a second embodiment of a shelf system.

FIG. 5 illustrates another embodiment of a shelf system 500 that may be used in a lyophilization process/apparatus for example apparatus 100 or apparatus 200 described above. Shelf system 500 includes shelves 520, which provide a surface for placing material to be lyophilized. The material may be maintained within a container such as a tray, bag, or bottle and the container placed on first plates 504 of shelves 520. Shelf system 500 also includes second plates 508 that are also part of shelves 520 and that are opposed to, and positioned above at least one of first plates 504. Additionally, shelf system 500 also includes a movement control system 512 that may be used in embodiments to change the distance between first plates 504 and second plates 508 of shelves 520. As described in greater detail below, the distance between first plates 504 and second plates 508 can be changed to apply some pressure to materials that are being lyophilized. The movement control system 512 may be designed, in embodiments, to move first plates 504 toward, and away from, stationary second plates 508, while in other embodiments second plates 508 may be moved toward, and away from, stationary first plates 504. In yet other embodiments, the movement control system 512 may be designed to move both first plates 504 and second plates 508 toward and away from each other.

Movement control system 512 may include any appropriate system(s) for moving plates 504 and/or 508 of shelves 520, and may, in embodiments, have similar components as movement control system 312 (FIG. 3), including computer system(s), such as controllers, that include processor(s), memory, input devices, output devices, communication devices or any combination thereof. System 512 may also include other subsystems such as hydraulic, pneumatic, or mechanical systems that may include one or more motors, actuators, pumps, compressors, cylinders, pistons, tubing, valves, bladders, sensors, regulators, or any combination thereof.

Figure 6:
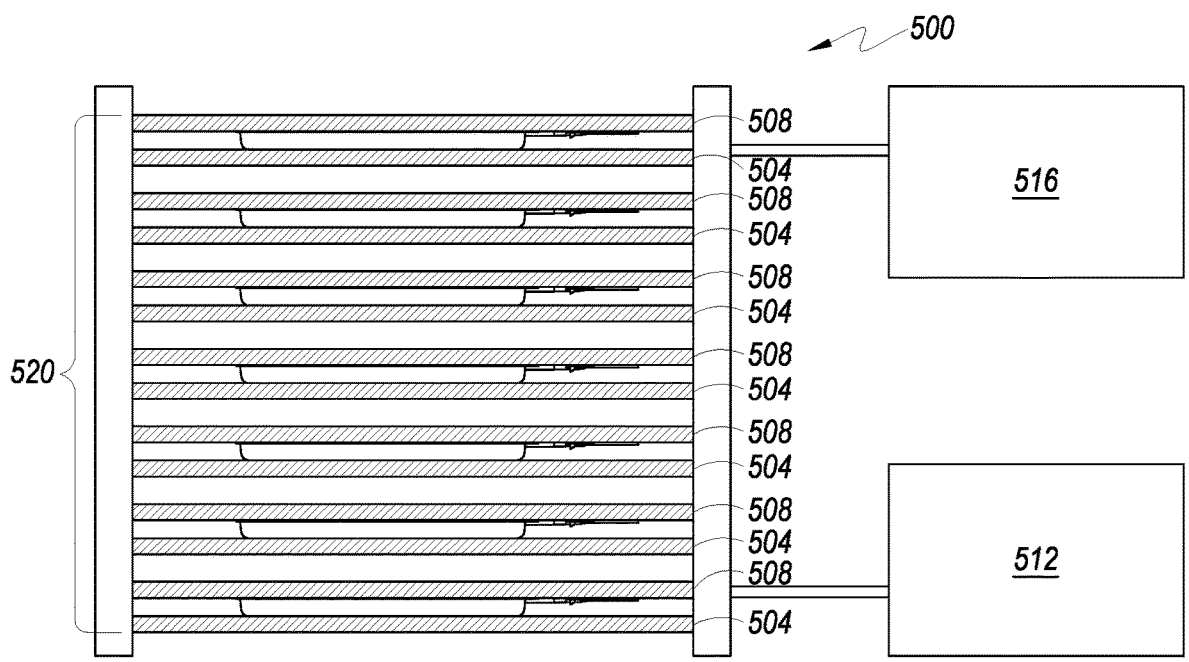
FIG. 6 illustrates the shelf system of FIG. 5 with the plates having been moved as compared to FIG. 5.

FIG. 6 illustrates shelf system 500 from FIG. 5, with the plates 504 and 508, of shelves 520, moved to press material during a lyophilization process, and in particular during a freezing step of a lyophilization process. As shown in FIG. 6, second plates 508 have been moved down toward first plates 504. In the position shown in FIG. 6, pressure is applied to each of the containers on the first plates 504 by applying some pressure with the second plates 508. The application of some pressure, and/or generally shaping the material during freezing, is believed to improve the efficiency in the process of lyophilization and is used in some embodiments.

System 500 also includes a thermal fluid system 516, which may be similar to thermal fluid system 316. The thermal fluid system 516 circulates a thermal fluid within at least some portion of shelves 520 to control the temperature of at least some of the plates 504, 508 and consequently material that is on the plates 504, 508 for lyophilization. Thermal fluid system 516 may be used to remove or add energy to shelves 520, during various steps of a lyophilization process as described in greater detail below.

The description of the shelf systems 300 and 500 above are provided for purposes of illustrating some features of embodiments of the present invention. It is noted that embodiments of the present invention may include additional features that are not described above but are still within the scope of the present invention. For example, the number of plates in the system may vary. In some embodiments, the plates for holding material to be lyophilized (e.g., 304, 504) may be more than two (2), more than three (3), more than four (4), more than 5, or more than (6). In other embodiments, the plates for holding material to be lyophilized (e.g., 304, 504) may be less than twelve (12), less than (11), less than ten (10), less than nine (9), or less than (8). In one embodiment, there are seven (7) plates for holding material to be lyophilized (e.g., 304, 504).

In other embodiments, the plates for holding material to be lyophilized (e.g., 304, 504) may have other features. For example, the plates may have a raised lip around the perimeter to ensure that any leakages are maintained on the plate and can be easily cleaned up. Also, the plates may be connected to the movement control systems (312, 512) and/or thermal fluid systems (316, 516) using any appropriate connections including connectors, tubing, fittings, pipes, adapters etc. In one embodiment, the plates are connected so that they may be easily disconnected (e.g., using quick disconnect valve fittings) from the movement control systems (312, 512) and/or thermal fluid systems (316, 516) to allow them to be easily cleaned.

Figure 7:
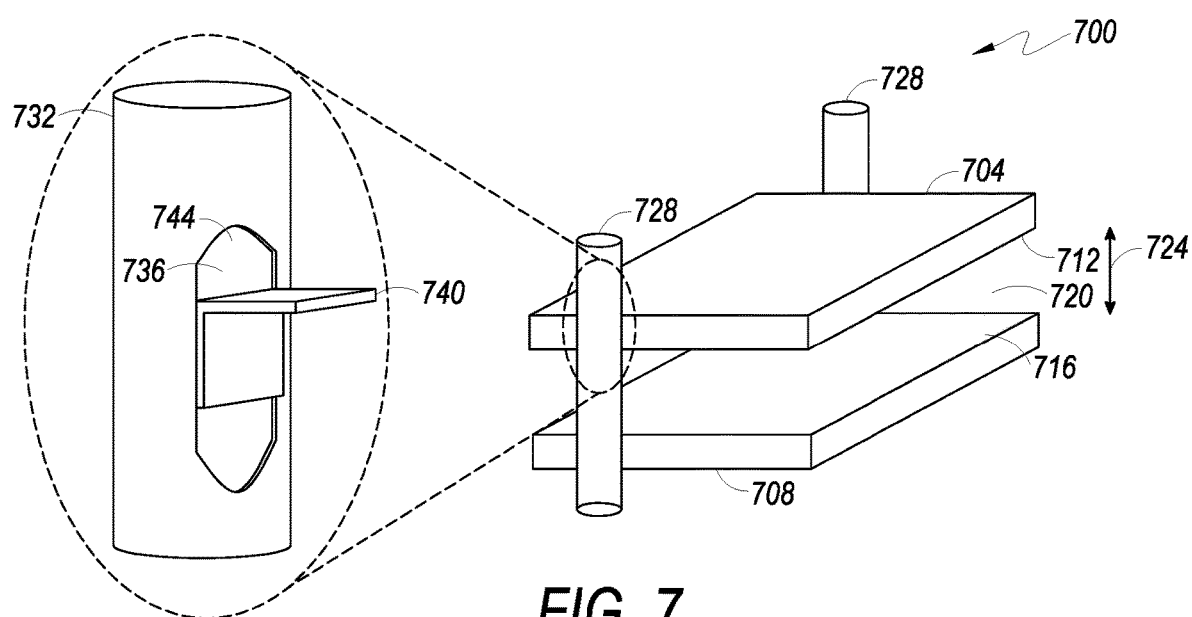
FIG. 7 illustrates an embodiment of a mechanism for moving two plates of a shelf system that may be part of the systems shown in FIGS. 3-6.

FIG. 7 illustrates an embodiment of a system 700 that includes two plates and a mechanism for moving plates that may be part of the shelf systems 300 or 500 shown in FIGS. 3-6. First plate 704 is positioned above a second plate 708 such that surface 712 of first plate 704 is opposed to surface 716 of second plate 708. As shown in FIG. 7, a space 720 is defined between the two surfaces 712 and 716 where material is placed to be lyophilized. As illustrated by arrow 724, the space 720 may be increased or decreased by movement of one or more of plates 704 and 708. The space 720 may be decreased so that in embodiments the material to be lyophilized may be pressed during one or more steps of the lyophilization process. The space 720 may be increased to relieve the pressure, or when positioning material to be lyophilized onto plate 708.

It is noted that any mechanism for moving one or more of plates 704 and 708 may be used with embodiments. FIG. 7 illustrates one example of a mechanism for moving the plates 704 and/or 708 to increase or decrease the size of space 720. In the embodiment shown in FIG. 7, support members 728 are designed to be attached to both plates 704 and 708, as well as allow movement of plates 704 and 708 toward and away from each other.

Support members 728 may include an outer support 732 and an inner support 736. For example, outer support 732 may be a hollow tube with the inner support 736 being a shaft positioned inside the hollow tube. In some embodiments, one of plates 704 or 708 may be attached to the outer support 732 and the other may be attached to the inner support 736. The plates 704, 708 may be attached to the support member(s) 728 by any suitable mechanism one non-limiting example includes the use of L-bracket(s) such as L-bracket 740. Also, in some embodiments, fasteners such as screws, nuts, bolts, washers, or any combination thereof, may be used to attach plates 704 and 708 to portions of support members 728.

In the embodiment shown in FIG. 7, outer support 732 includes an opening 744 to allow L-bracket 740 to attach to inner support 736 and still allow the L-bracket 740 to move vertically. The movement of L-bracket 740, which is attached to one of plates 704 or 708, increases or decreases space 720.

In embodiments, at least portions of support members 728 are connected to a movement control system such as movement control system 312 (FIGS. 3 and 4) or movement control system 512 (FIGS. 5 and 6). As noted above, the movement control system may be used to control the distance of space 720, and may increase space 720 during loading and some lyophilization steps, and decrease space 720 during some lyophilization steps to press the material being lyophilized.

It is noted that the support members 728 and bracket 740 are merely one example of a mechanism for moving plates 704 and 708. In other embodiments, different components may be used as part of different mechanisms for moving plates 704 and 708; non-limiting examples include brackets, rails, fasteners, bearings, bushings, shafts, tubes, plates, welds, or any combination thereof.

Plates 704 and 708 in FIG. 7 are illustrated as merely one embodiment of a plate structure that may be part of a shelf system such as the shelf systems 300 or 500 shown in FIGS. 3-6. Other embodiments may utilize different structures or designs. As noted above, other embodiments may have different mechanisms for changing the distance of space 720 between plates 704 and 708. Other shelf systems may also include more than the two support members 728 shown in FIG. 7, such as four or more support members located near the four corners of plates 704 and 708. This is merely another example, and other embodiments are included within the scope of the present invention.

Figure 8A:
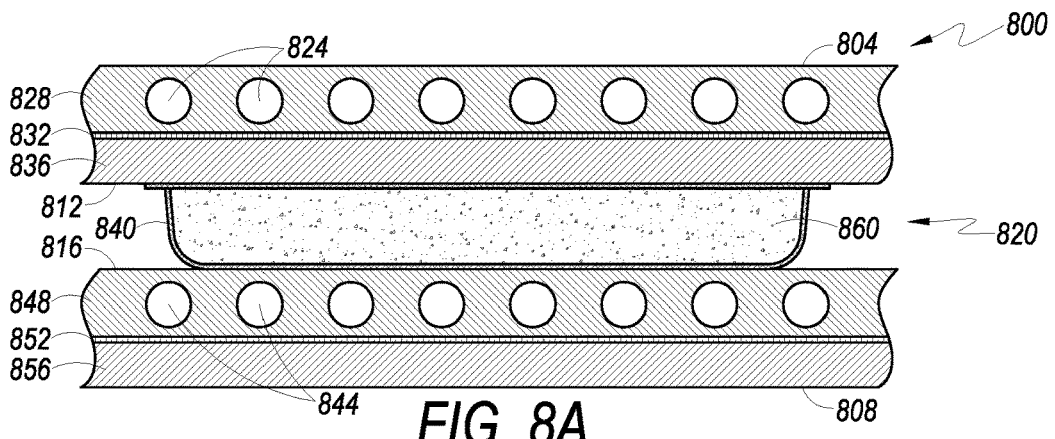
FIGS. 8A and 8B illustrate first embodiments of a structure of two plates that may be used as part of a shelf system.
Figure 8B:
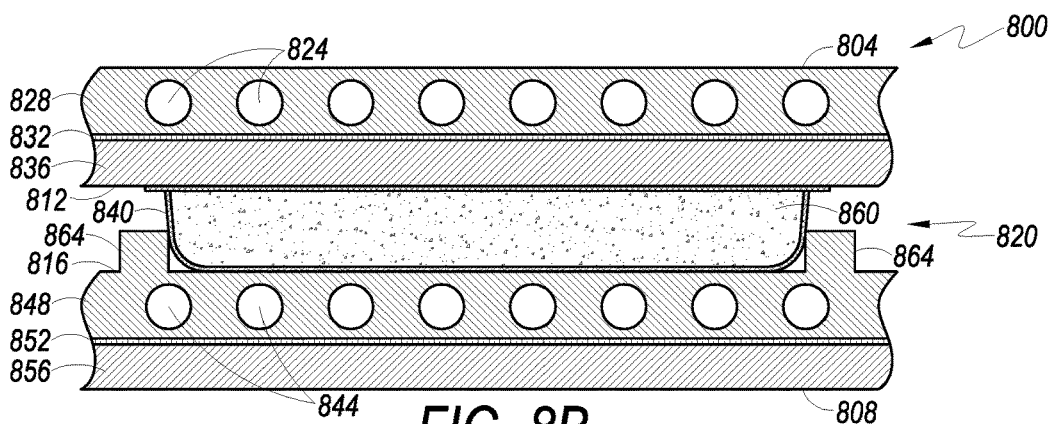

FIGS. 8A and 8B illustrates a first embodiment of a two plate structure 800 that may be used as part of a shelf system, such as system 300 illustrated in FIGS. 3 and 4. The structure 800 includes a first plate 804 and a second plate 808. First plate 804 includes a surface 812 that is opposed to a surface 816 of plate 808. The two opposed surfaces 812 and 816 define a space 820 between them.

Each of plates 804 and 808 in embodiments has similar structures. Plate 804 has a first layer 828, which in embodiments may be made from a thermally conductive material. The first layer 828 includes channels 824 that provide a flow path for a thermal fluid. The thermal fluid may be used in embodiments to control the temperature of the first layer 828 by heating or cooling the first layer 828.

The plate 804 may also include an interface 832 between the first layer 828 and a second layer 836. In embodiments, interface 832 may include thermal insulating material that allows the temperature of first layer 828 to be different than the temperature of second layer 836. In other embodiments, interface 832 may alternatively, or in addition, have properties that help adhere second layer 836 to first layer 828.

In one embodiment, second layer 836 comprises an IR radiating material, which in embodiments may be a ceramic material, metallic material, intermetallic material, and/or a composite material. In particular embodiments, the material may be an infrared (IR) radiator that radiates IR energy. In these particular embodiments, the second layer 836 may include embedded elements for heating layer 836 to facilitate IR radiation from surface 812. For example, the second layer 836 may include, electrodes, heating element(s), sensor(s) (e.g., thermocouple(s)), and/or combinations thereof. As discussed in greater detail below, the IR energy radiated by second layer 836 from surface 812 may be used in performing some steps of a lyophilization process. As is shown in the embodiment of FIGS. 8A and 8B, plate 808 has a similar structure as plate 804 with similar first layer 848, second layer 856, interface 852, and channels 844 for circulating thermal fluid.

In embodiments, plate structure 800 may be used in shelf system 300 (FIGS. 3 and 4) as part of a lyophilization apparatus that also includes other components such as a vacuum system for creating a low pressure environment around at least the shelves of shelf system 300. In these embodiments, plates 804 and 808 may comprise part of shelves 320 and be connected to shelf movement system 312, as well as thermal fluid system 316.

In operation, shelf system 300 (with plate structure 800) may be positioned within a vacuum chamber (e.g., 104 or 204) that is used to create a low pressure (below atmospheric pressure) environment around at least the shelves 320 (e.g., plates 804 and 808) of system 300. Shelf movement system 312 may then increase space 820 to allow container 840 (containing material 860, which in embodiments may be a liquid such as a biological liquid) to be positioned onto surface 816 of plate 808. System 312 may then move one or more plates 804 and/or 808 to decrease space 820 and slightly press on container 840 (as shown in FIG. 8). In embodiments, thermal fluid system 316 may then circulate a thermal fluid through channels 844 of plate 808 to cool first layer 848 of plate 808, and consequently the material 860 within container 840.

Without being bound by theory, it is believed that pressing the material to be lyophilized, e.g., material 860 in container 840, during a freezing step, may shape the material to create a more uniform cross-section of material 860. Accordingly, it is believed that the more uniform cross-section will increase the efficiency of removing a component, e.g., in embodiments ice, from the material 860 during a subsequent sublimation step. In other words, reducing variations in thickness may allow sublimation to occur at a uniform rate as the sublimation interface advances through the material 860.

After material 860 has been frozen, the environment around shelves 320 may be brought to a low pressure to promote sublimation of at least one component of the material 860. Shelf movement system 312 may then increase space 820 in preparation for the sublimation step. In addition, the thermal fluid may be circulated through channels 844 to add thermal energy to material 860 in container 840 (through first layer 848, which would be made from a thermally conductive material) to promote sublimation of a component in material 860.

As noted above, in some embodiments, second layer 836 may comprises an IR radiator. In these embodiments, the IR radiator may be activated to direct IR energy to material 860 in container 840. The IR energy may provide additional energy for sublimating a component from material 860. In these embodiments, the sublimation step may be completed more quickly by the addition of both thermal energy (from thermal fluid circulating in channels 844) as well as IR energy (from IR radiator in second layer 836 of plate 804).

In some embodiments, after sublimation, the material 860 may be maintained at the low pressure with the continued addition of energy (thermal and/or IR). In some embodiments this is done to remove the same, or some additional component, that is chemically combined with other compound(s) in the material 860. As one example, water of hydration may be removed during this step.

Once the component has been removed from material 860 by sublimation, the environment around shelves 320 may be brought to atmospheric pressure and the material 860 (and container 840) may then be removed from plate 808 for storage or additional processing.

As may be appreciated, structure 800 also allows a plate (e.g., plate 804 or 808) to be used to process material positioned both below and above the plate. For example, as described above, second layer 836 may include an IR radiator to add energy to material located beneath it. However, first layer 828 may be used to cool the material positioned above the first layer 828 and freeze any liquid in the material into a solid, as well as add thermal energy to the material (e.g., by circulating thermal fluid in channels 824). Similarly, second layer 856 of plate 808 may be used as an IR radiator for material positioned below second layer 856, while as noted above first layer 848 may be used to cool the material 860 and freeze any liquid in the material and add thermal energy during the sublimation step.

FIG. 8B illustrates another embodiment of plate structure 800. In this embodiment, plate 808 has features that are shaped to hold a container and/or material for lyophilization. As shown in FIG. 8B, plate 808 includes a lip 864 that in embodiments corresponds to at least a portion of the shape of the container 840. Lip 864 may be used in embodiments to define a location where a container 840 may be placed on plate 808. Also, in some embodiments when plate 804 is used to press container 840. Lip 864 may be used to ensure that container 840 does not move when being pressed by plate 804 and may also be used as a form, during a freezing step, for the material being lyophilized.

In some embodiments, lip 864 may surround only a portion of a container. For example, the lip may be on two sides of the container, on three sides of the container, or be discontinuous around some portion of the container but not others.

The description above regarding use of plate structure 800 in shelf system 300 is provided merely for illustrative purposes. A lyophilization process that utilizes plate structure 800 and shelf system 300 may include additional steps not described above. The description above is not intended to be complete and is provided merely to illustrate some features of plate structure 800.

Figure 9:
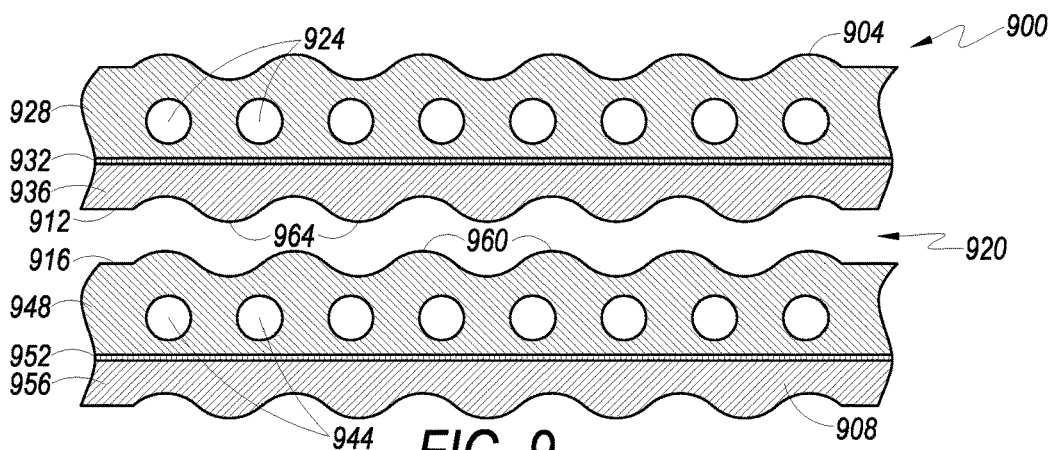
FIG. 9 illustrates a second embodiment of a structure of two plates that may be used as part of a shelf system.

FIG. 9 illustrates a second embodiment of a two plate structure 900 that may be used as part of a shelf system, such as part of shelves 320 in system 300 (FIGS. 3 and 4). Structure 900 has some similar features to structure 800 described above. Structure 900 may include a first plate 904 and a second plate 908. First plate 904 includes a surface 912 that is opposed to a surface 916 of plate 908. The two opposed surfaces 912 and 916 define a space 920 between them.

As is illustrated in FIG. 9, surface 916 includes some features, e.g., ridges 960. The features are provided to create a surface that has an improved heat and/or mass transfer surface area. In embodiments, this may be accomplished by imparting a macro texture. For example, ridges 960 and 964 may impart a texture to a surface on a material during a freezing step of a lyophilization process. Without being bound by theory, it is believed that the improved heat and/or mass transfer surface area on the material may promote sublimation (of a component of the material being lyophilized) during a sublimation step. Although, surface 912 is shown with ridges 964 and surface 916 is shown with ridges 960, it is noted that surfaces 912 and 916 may include other types of textures that may provide improved surface area for heat and mass transfer. As one non-limiting example, surface 916 may have some pattern (random or regular) of concave and/or convex half spheres of the same or different sizes.

In one embodiment, the size, shape, or geometry of the features may depend upon a number of considerations. For example, for features on surface 916, the features may depend upon factors that affect the transfer of thermal energy to the material being lyophilized, for example the stiffness of the container in which the material to be lyophilized is stored. The stiffness of the container may affect the contact between the material to be lyophilized and the surface 916, which may affect the thermal energy transfer.

Each of plates 904 and 908 in embodiments has similar structures which may be different in other embodiments. Plate 904 has a first layer 928, which in embodiments may be made from a thermally conductive material. The first layer 928 includes channels 924 that provide a flow path for a thermal fluid. The thermal fluid may be used in embodiments to control the temperature of the first layer 928 by heating or cooling the first layer 928.

Plate 904 may also include an interface 932 between the first layer 928 and a second layer 936. In embodiments, interface 932 may include thermal insulating material that allows the temperature of first layer 928 to be different than the temperature of second layer 936. In other embodiments, interface 932 may alternatively, or in addition, have properties that help adhere second layer 936 to first layer 928.

In one embodiment, second layer 936 comprises an IR radiating material. In particular embodiments, the IR radiating material may be an infrared (IR) radiator that radiates IR energy. In these particular embodiments, the second layer 936 will include embedded electrodes for heating layer 936 and a surface 912 for radiating IR energy. The IR energy may be used in performing some steps of a lyophilization process. As is shown in the embodiment of FIG. 9, plate 908 has a similar structure as plate 904 with similar first layer 948, second layer 956, interface 952, and channels 944 for circulating thermal fluid.

Figure 10:
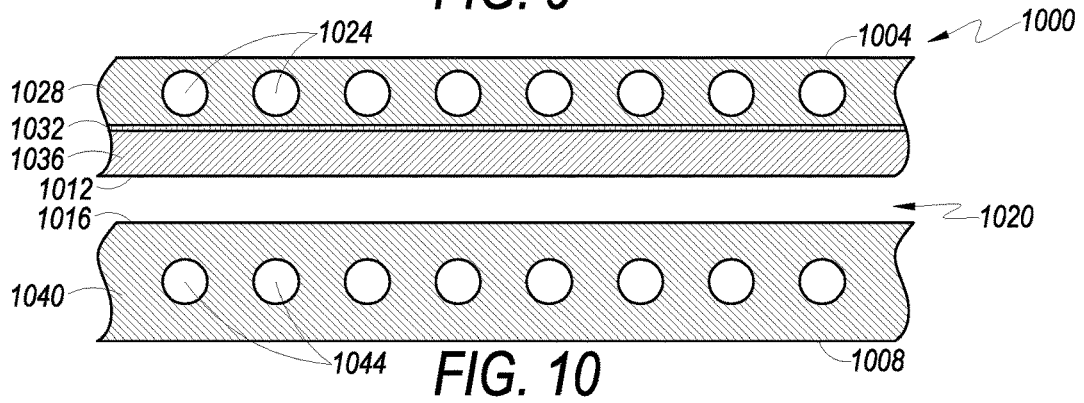
FIG. 10 illustrates a third embodiment of a structure of two plates that may be used as part of a shelf system.

FIG. 10 illustrates a third embodiment of a two plate structure 1000 that may be used as part of a shelf system, such as shelves 520, of system 500 illustrated in FIGS. 5 and 6. Structure 1000 may include a first plate 1004 and a second plate 1008. First plate 1004 includes a surface 1012 that is opposed to a surface 1016 of plate 1008. The two opposed surfaces 1012 and 1016 define a space 1020 between them where material to be lyophilized may be positioned.

Plates 1004 and 1008 in embodiments have a different structure. Plate 1004 has a first layer 1028, which in embodiments may be made from a thermally conductive material. The first layer 1028 includes channels 1024 for circulating a thermal fluid. Plate 1004 may also include an interface 1032 between the first layer 1028 and a second layer 1036. In embodiments, interface 1032 may include thermal insulating material that allows the temperature of first layer 1028 to be different than the temperature of second layer 1036. In other embodiments, interface 1032 may alternatively, or in addition, have properties that help adhere second layer 1036 to first layer 1028.

In one embodiment, second layer 1036 comprises an IR radiating material. In particular embodiments, the IR radiating material may be an infrared (IR) radiator that radiates IR energy. In these particular embodiments, the second layer 1036 will include embedded elements for generating and radiating IR energy. For example, the second layer 1036 may include, electrodes, heating element(s), sensor(s) (e.g., thermocouple(s)), and/or combinations thereof. The IR energy radiated by second layer 1036 may be used in performing some steps of a lyophilization process.

As is shown in the embodiment of FIG. 10, plate 1008 may include a layer 1040. In embodiments, the layer 1040 may be made from a thermally conductive material. The layer 1040 may include channels 1044 that provide a flow path for circulating a thermal fluid. The thermal fluid may be used in embodiments to control the temperature of the layer 1040 by heating or cooling the first layer 1040 and any material positioned on surface 1016, which may be undergoing lyophilization.

In embodiments, plate structure 1000 may be used in shelf system 500 (FIGS. 5 and 6) as part of a lyophilization apparatus that also includes other components such as a vacuum system for creating a low pressure (below atmospheric pressure) environment around the shelf system 500. In these embodiments, plates 1004 and 1008 may be part of shelves 520 and be connected to shelf movement system 512 as well as thermal fluid system 516.

In operation, shelf system 500 with plate structure 1000 (as part of shelves 520) may operate similar to shelf system 300 with plate structure 800 as described above. The plate structure 1000 as part of shelves 520 may be positioned within a vacuum chamber that is used to create a low pressure, e.g., less than atmospheric pressure, environment around at least the shelves 520 of system 500. Shelf movement system 512 may then be operated to increase space 1020 to allow a container (containing material, e.g., a biological liquid, to be lyophilized) to be positioned onto surface 1016 of plate 1008. System 512 may then move one or more plates 1004 and/or 1008 to decrease space 1020 and press the container with material to create a layer of material of substantially uniform thickness. In embodiments, thermal fluid system 516 may then circulate a thermal fluid through channels 1044 of plate 1008 to cool layer 1044 of plate 1008, and consequently the material to be lyophilized.

As noted above, (without being bound by theory) it is believed that pressing the material to be lyophilized, during a freezing step, may create a more uniform cross-section of material. Accordingly, it is believed that the more uniform cross-section will increase the efficiency of removing a component, such as ice, from the material during a subsequent sublimation step. In other words, reducing variations in thickness may allow sublimation to occur at a uniform rate as the sublimation advances through the material making the sublimation step more efficient and possibly shorter.

In other embodiments, during a freezing step, the material to be lyophilized may be shaped or formed, e.g., on a surface. For example, as noted above, a texture may be imprinted on the material to increase surface area, see e.g., FIG. 9. In other embodiment, the material may be shaped based on the shape of a shelf or the container storing the material.

After the material on surface 1016 has been frozen, the environment around shelves 520 (with plate structure 1000) may be brought to a low pressure to promote sublimation of at least one component of the material. Shelf movement system 512 may then increase space 1020 in preparation for the sublimation step. In addition, the thermal fluid may be circulated through channels 1044 to add some thermal energy to the material to promote sublimation of a component in the material.

As noted above, in some embodiments, second layer 1036 is a layer that comprises an IR radiator. In these embodiments, the IR radiator may be activated to direct IR energy to the material on surface 1016. The IR energy may provide additional energy for sublimating a component from the material. In these embodiments, the sublimation step may be completed more quickly by the addition of both thermal energy (from thermal fluid circulating in channels 1044) as well as IR energy (from IR radiator in second layer 1036 of plate 1004).

In some embodiments, only IR energy may be used to perform the sublimation step. As noted above, the IR radiator in second layer 1036 may add energy to the frozen material. In some of these embodiments, thermal fluid circulating in channels 1044 may be used to cool the material being lyophilized. Without being bound by theory, it is believed that during a lyophilization process, sublimation of material takes place at a surface of the material. When thermal energy is applied to a bottom surface of the material (e.g., when using a plate structure shown in FIG. 10) to be lyophilized, the energy must be conducted to the top surface where the sublimation is taking place. While the heat travels through the material, it may raise the temperature of the material to a point where a component, e.g., ice, melts, making it even more difficult to transfer thermal energy to the surface of the material.

As a result, in some embodiments, only IR energy is used to sublimate the material. In addition, to avoid any melting, thermal energy may be removed from a bottom surface of the material to cool the material and avoid any melting. For example, referring to FIG. 10, material may be positioned in space 1020 for sublimation. An IR radiator in second layer 1036 may be used to provide IR energy to the material to sublimate a component of the material from a top surface of the material opposed to second layer 1036. To avoid any melting that may take place, thermal fluid in channels 1044 may be circulated at a temperature that removes energy, e.g., acts as a heat sink, to keep the material cool and avoiding any melting. These are merely some examples of processes that may be performed using the plate structure shown in FIG. 10. Other embodiments may utilize the plate structure in FIG. 10 in performing processes that include different steps.

In some embodiments, after sublimation, the material may be maintained at the low pressure (e.g., less than atmospheric pressure) with the continued addition of energy (thermal and/or IR). In some embodiments this is done to remove the same, or some additional component that is chemically combined with other compound(s) in the material. As one example, water of hydration may be removed during this step.

Once the component (e.g., sorbed component) has been removed from the material by sublimation, the environment around shelves 520 may be brought to atmospheric pressure and the material may then be removed from plate 1008 for storage or subsequent processing.

It is noted that although the description above of plate structures 800, 900, and 1000 has been made with respect to embodiments that incorporate the plate structures in a lyophilization apparatus or system, e.g., apparatus 100 or apparatus 200, the present invention is not limited thereto. In other embodiments, plate structures 800, 900, and 1000 may be part of different apparatuses that are used as part of a lyophilization process that is not performed in a single apparatus. As one non-limiting example, the evaporation step and the freezing step described above may be performed in an apparatus that includes one or more features of plate structures 800, 900, or 1000. The sublimation step may then be performed in another machine that may incorporate the same, different, or none of the features of plate structures 800, 900, or 1000.

As another example, a process may involve only a freezing and a sublimation step. The freezing step may be performed in an apparatus that includes one or more features of plate structures 800, 900, or 1000, or other features that may for example shape the material during freezing. The sublimation step may then be performed in another machine that may incorporate the same, different, or none of the features of plate structures 800, 900, or 1000.

As one additional example, the freezing step that may include creating a surface on material that has improved heat and mass transfer surface area may be performed in a separate apparatus. In these embodiments, features of plate structure 900 may be used in the apparatus. Prior step, and subsequent steps, may be performed by one or more different apparatuses.

Furthermore, although specific features have been described above, it is noted that other embodiments may include additional structures, processes, or steps and still be within the scope of the present invention. As one non-limiting example, a lyophilization process may involve sterile material that must remain sterile. In these embodiments, the apparatuses may include features that for example maintain sterility of shelf systems, plates, or other structures used in the lyophilization process. The sterility may be maintained using a variety of systems some non-limiting examples including a UV (ultraviolet) radiation system, microwave systems, washing systems, steam systems, pressure systems, additional vacuum systems, filter systems, and/or combinations thereof. As one example, a UV radiation system with UV lamps or UV LED's may be utilized to sterilize components of a lyophilization apparatus or system to maintain a sterile environment for materials being lyophilized that must be maintained sterile.

Figure 11:
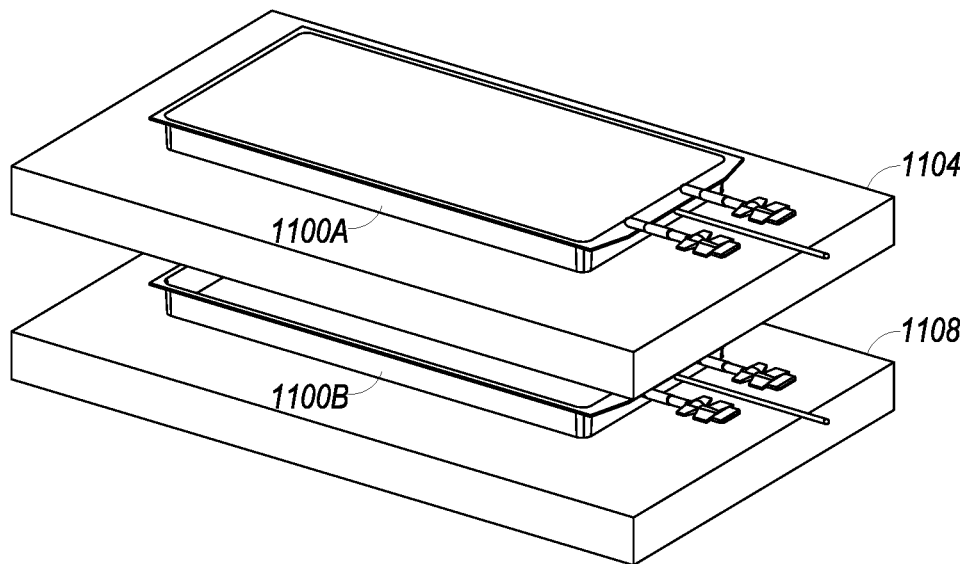
FIG. 11 illustrates containers that may be used to store material for lyophilization.

FIG. 11 illustrates an embodiment of containers 1100A and 1100B that may be used to store material for lyophilization. As shown in FIG. 11, containers 1100A and 1100B are positioned on plates 1104 and 1108 which may be part of a shelf system in a lyophilization apparatus such as apparatus 100 or apparatus 200.

Figure 12:
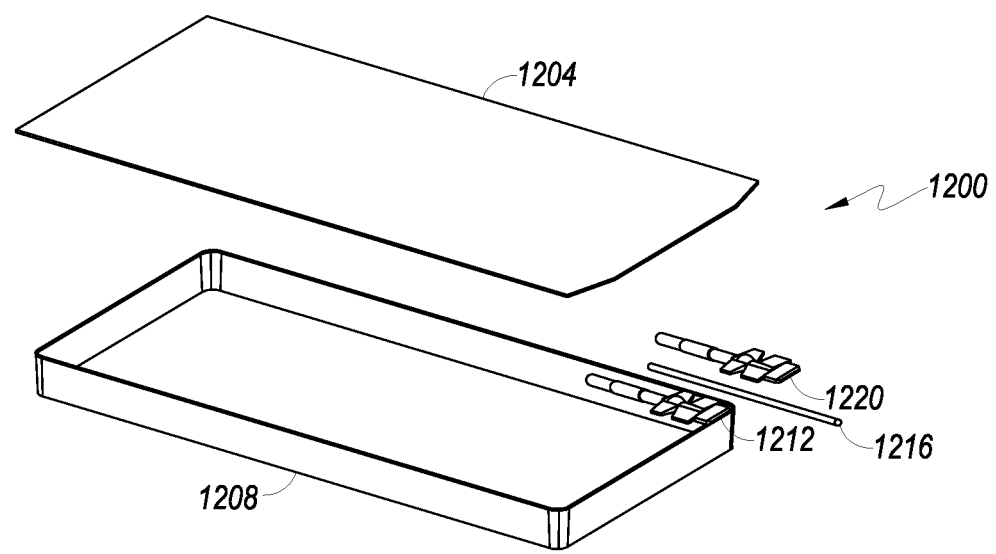
FIG. 12 illustrates an exploded view of a container similar to the containers of FIG. 11.

FIG. 12 illustrates an exploded view of container 1200, which includes similar features as containers 1100A and 1100B. Container 1200 includes a first wall 1204, a second wall 1208, and three port connectors 1212, 1216, and 1220. As illustrated in FIG. 12, the three port connectors 1212, 1216, and 1220 are positioned between first wall 1204 and second wall 1208. The port connectors may be used to connect to other containers, in some embodiments, in order to fill container 1200 with material for lyophilization, to add a liquid to container 1200 to reconstitute the lyophilized material, and/or to remove material from container 1200 (e.g., reconstituted lyophilized material). In embodiments, port connectors 1212, 1216, and 1220 may not be positioned between the first wall 1204 and the second wall 1208. For example, in embodiments, one or more of port connectors 1212, 1216, or 1220 may be integrated into one of walls 1204 or 1208.

First wall 1204 may in some embodiments be made from a material that is permeable to at least some gasses. For example, 1204 may be made of a material that has a relatively high permeability to water vapor but low penetration of liquid water, i.e., is water resistant. Furthermore, in other embodiments, first wall 1204 is also made of a material that is biocompatible. Non-limiting examples of possible materials for use in first wall 1204 include materials made from flashspun high-density polyethylene (HDPE) and polytetrafluoroethylene (PTFE). In one embodiment, first wall 1204 may include a non-woven textile that includes fibers made from flashspun HDPE. In other embodiments, the first wall 1204 may be made from copolymers such as polyethylene copolymers, vinyl copolymers, acrylic copolymers, polypropylene copolymers, or amide copolymers that may be cast on a substrate (e.g., woven or nonwoven textile). In one specific embodiment, first wall 1204 may be made of an acrylic copolymer cast on a nylon nonwoven textile.

In embodiments, wall 1204 may be made from materials that are manufactured using particular processes. For example, as noted above, the materials may be manufactured using a spinning process including, without limitation, flashspun, spunbonded, dry-laid, wet-laid, melt blow, and spunlaced. These processes may produce nonwoven textiles, or may be used to generate fibers that are further processed, e.g., by stretching, weaving, etc. As another example, the materials may include polymers or copolymers that are cast on a substrate such as a woven or nonwoven textile. Any of these processes may be used in making the material of first wall 1204 to create the material with the desired properties, gas permeability, tensile strength, water resistance, etc.

In embodiments, first wall 1204 has a water vapor transmission of greater than about 15 metric perms (perms are metric perms unless otherwise noted), greater than about 20 perms, greater than about 25 perms, greater than 30 perms, greater than about 35 perms. In other embodiments, the water vapor transmission of first wall 1204 may be greater than about 50 perms, greater than about 75 perms, or greater than 100 perms, greater than about 150 perms or even greater than about 200 perms. In some embodiments, first layer 1204 has a water vapor permeability of between about 10 perms to about 70 perms, such as between about 15 perms and about 65 perms, or between about 20 perms and about 60 perms. In other embodiments, first layer 1204 may have a water vapor permeability of between about 50 perms to about 1000 perms, such as between about 100 perms and about 750 perms, or between about 200 perms and about 500 perms. Also, in some embodiments, the first layer 1204 may have a water resistance (i.e. hydrostatic head) of greater than about 100 cm, greater than 150 cm, greater than about 200 cm, and even greater than about 250 cm. In some embodiments, first layer 1204 has a water resistance value of between about 50 cm to about 400 cm, such as between about 100 cm and about 350 cm, or between about 150 cm and about 300 cm. It is noted that in some embodiments, layer 1204 may have any of the above-mentioned water vapor transmission values in combination with any of the above-mentioned water resistance values. In some embodiments, wall 1204 may be made from material that includes a nonwoven textile made from polymer fibers manufactured using a spinning process. In other embodiments, wall 1204 may be made from material that includes a copolymer cast on a nonwoven textile. These materials may be manufactured specifically to provide the water vapor transmission and water resistance values described above.

In embodiments, wall 1208 may be made from any suitable material including polymers. In some embodiments, wall 1208 is made from a transparent or translucent material, non-limiting examples including polycarbonate, acrylics, polystyrene, polysulfone, polyethylene, polyolefin, polypropylene, polyvinylchloride, or combinations thereof. The use of a transparent or translucent material may be useful in embodiments where the material within container 1200 may be subjected to a pathogen reduction process that involves the use of a photosensitizer and illumination. In these embodiments, container 1200 may be able to be used as an illumination container. In embodiments, wall 1208 is also biocompatible, including at temperatures and pressures typical of a lyophilization process. In embodiments, wall 1208 includes a polyolefin material.

Wall 1208 may in some embodiments be a single sheet of material, such as when container 1200 is a bag. In other embodiments, wall 1208 may provide some depth for material that is stored in container 1200. In these embodiments, wall 1208 may be in the form of a tray.

Figure 13:
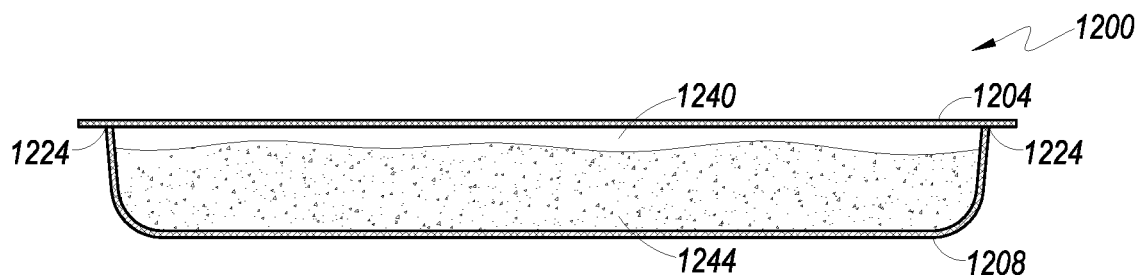
FIG. 13 illustrates a cross sectional view of the container of FIG. 12 maintaining a fluid.

FIG. 13 illustrates a cross sectional view of container 1200 showing volume 1240. As shown in FIG. 13, wall 1204 is attached to wall 1208 at one or more joints 1224. Therefore, in addition to the properties of walls 1204 and 1208 mentioned above, the walls are also in embodiments made of materials that are compatible with each other to allow them to be attached together to form container 1200. Walls 1204 and 1208 may be attached together using one or more suitable techniques, some non-limiting examples including heat sealing, ultrasonic welding, RF welding, solvent welding, laser welding, adhesive bonding, and/or combinations thereof.

In one embodiment, container 1200 is used to lyophilize a biological fluid such as plasma 1244 (e.g., human plasma) shown in FIG. 13 maintained within volume 1240. In this embodiment, wall 1204 may be made of a material with a water vapor transmission of greater than about 35 perms and a water resistance of greater than about 100 cm so that during sublimation of ice, water vapor may escape through layer 1204 easily, but the liquid plasma will not leak out of volume 1240. Also, the water resistance is useful when the plasma is reconstituted using a water based solution.

In addition to the other features of container 1200, it may also, in embodiments, be capable of maintaining the material to be lyophilized sterile. That is, both walls 1204 and 1208 provide barriers to pathogens, bacteria, or other microorganisms to prevent contamination of the material within container 1200. This feature may be particularly useful in situations where the material to be lyophilized is a biological fluid that may be later infused into a patient. The ability to maintain a closed sterile environment within container 1200 avoids the need to ensure sterility of the environment during lyophilization. In other words, the lyophilization process may not require sterilization of the apparatus(es) used in the process before performing the various steps of the lyophilization process. This may eliminate the need for expensive vacuum systems, filter systems, or other systems used in a clean room environment. In these embodiments, the container 1200 maintains a closed system during lyophilization and additional handling of container 1200 (e.g., storing, rehydrating the lyophilized material, and utilizing the rehydrated material).

Figure 14:
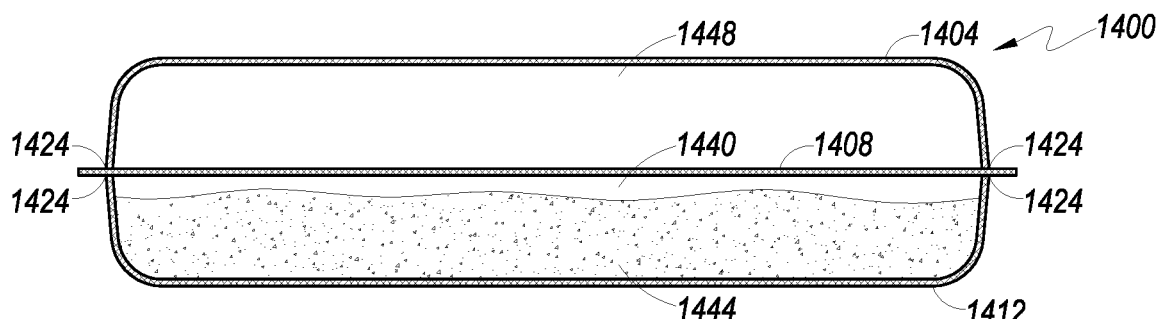
FIG. 14 illustrates a cross sectional view of a three walled container according to an embodiment.

FIG. 14 illustrates a cross sectional view of an embodiment of a three walled container 1400 with a volume 1440 storing a biological fluid (e.g., human plasma), for example, plasma 1444. As shown in FIG. 14, container 1400 includes a third wall 1404, a first wall 1408, and a second wall 1412. Third wall 1404 may be positioned above and adjacent to first wall 1408 as shown in FIG. 14. In embodiments, third wall 1404, in addition to other functionalities, is used to provide a layer of protection for first wall 1408. Having third wall 1404 prevents damage to first wall 1408 that may occur when handling container 1400, and also avoids any direct contact of hands or other objects with first wall 1408.

In embodiments, third wall 1404 and second wall 1412 may be made from similar material, which in embodiments is similar to the materials described above with respect to wall 1208. Third wall 1404 and second wall 1412 may be made of any suitable material including polymers. In some embodiments, third wall 1404 and second wall 1412 may be made from a transparent or translucent material, non-limiting examples including polycarbonate, acrylics, polystyrene, polysulfone, polyethylene, polyolefin, polypropylene, polyvinylchloride, or combinations thereof. The use of a transparent or translucent material may be useful in embodiments where the material within container 1400 may be subjected to a pathogen reduction process that involves the use of a photosensitizer and illumination. In these embodiments, container 1400 may be able to be used as an illumination container. In embodiments, wall 1404 is also biocompatible, including at temperatures and pressures typical of a lyophilization process. In embodiments, third wall 1404 and wall 1412 include a polyolefin material. In embodiments, walls 1404 and 1408 may be made of different materials.

First wall 1408 may in some embodiments be made from a material that is permeable to at least some gasses. For example, 1408 may be made of a material that has a relatively high permeability to water vapor but low penetration of liquid water, i.e., is water resistant. Furthermore, in other embodiments, first wall 1408 is also made of a material that is biocompatible. Examples of possible materials for use in first wall 1408 include materials made from flashspun high-density polyethylene (HDPE) and polytetrafluoroethylene (PTFE). In one embodiment, first wall 1408 may include a non-woven textile that includes fibers made from flashspun HDPE. In other embodiments, the wall 1408 may be made from copolymers such as polyethylene copolymers, vinyl copolymers, acrylic copolymers, polypropylene copolymers, or amide copolymers that may be cast on a substrate (e.g., woven or nonwoven textile). In one embodiment, first wall 1408 may be made of an acrylic copolymer cast on a nylon nonwoven textile.

In embodiments, first wall 1408 has a water vapor transmission of greater than about 15 perms, greater than about 20 perms, greater than about 25 perms, greater than 30 perms, and even greater than about 35 perms. In some embodiments, first wall 1408 has a water vapor permeability of between about 10 perms to about 700 perms, such as between about 20 perms and about 650 perms, or between about 30 perms and about 600 perms. Also, in some embodiments, the first wall 1408 may have a water resistance (i.e. hydrostatic head) of greater than about 100 cm, greater than 150 cm, greater than about 200 cm, and even greater than about 250 cm. In some embodiments, first wall 1408 has a water resistance value of between about 50 cm to about 400 cm, such as between about 100 cm and about 350 cm, or between about 150 cm and about 300 cm. It is noted that in some embodiments, first wall 1408 may have any of the above-mentioned water vapor transmission values in combination with any of the above-mentioned water resistance values.

As shown in FIG. 14, first wall 1408 is attached to both walls 1404 and 1412 at one or more joints 1424. Therefore, in addition to other properties, the walls are also made of materials that are compatible with each other to allow them to be attached together to form container 1400. The walls 1404, 1408, and 1412 may be attached together using one or more suitable techniques, some non-limiting examples including heat sealing, ultrasonic welding, RF welding, solvent welding, laser welding, and adhesive bonding.

In one embodiment, container 1400 is used to lyophilize a biological fluid such as plasma 1444. In this embodiment, wall 1408 may be made of a material with a water vapor transmission of greater than about 75 perms and a water resistance of greater than about 100 cm so that during a sublimation step (e.g., sublimation of ice), water vapor may escape through wall 1408 and into volume 1448. Wall 1404 may include one or more openings that allow gasses, e.g., water vapor, to escape into the environment from volume 1448. The water resistance of wall 1408 will prevent any water vapor that may condense in volume 1448 from leaking into volume 1440 and rehydrating the lyophilized plasma.

Figure 15:
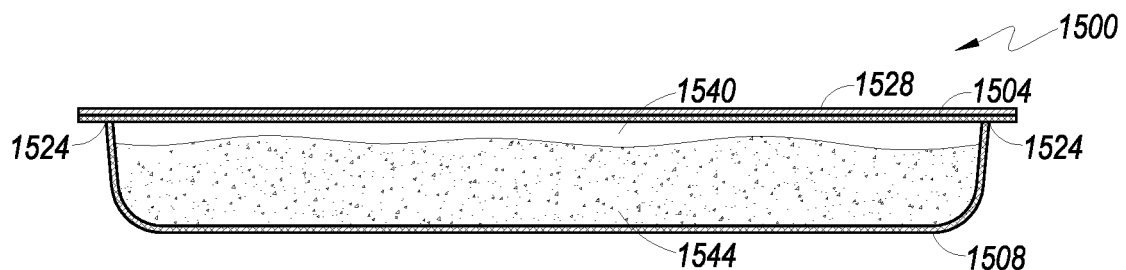
FIG. 15 illustrates a cross sectional view of a three walled container according to a second embodiment.

FIG. 15 illustrates a cross sectional view of a three walled container 1500 with a volume 1540 maintaining a biological fluid, for example, plasma 1544. As shown in FIG. 15, container 1500 includes a third wall 1528, a first wall 1504, and a second wall 1508. As shown in FIG. 15, third wall 1528 may be positioned above and adjacent to first wall 1504.

In embodiments, second wall 1508 may be made from material similar to the materials described above with respect to wall 1208 (FIGS. 12 and 13). Second wall 1508 may be made of any suitable material including polymers. In some embodiments, second wall 1508 may be made from a transparent or translucent material, non-limiting examples including polycarbonate, acrylics, polystyrene, polysulfone, polyethylene, polyolefin, polypropylene, polyvinylchloride, or combinations thereof. The use of a transparent or translucent material may be useful in embodiments where the material within container 1500 may be subjected to a pathogen reduction process that involves the use of a photosensitizer and illumination. In these embodiments, container 1500 may be able to be used as an illumination container. In embodiments, second wall 1508 may also be biocompatible, including at temperatures and pressures typical of a lyophilization process. In embodiments, third wall 1528 includes a polyolefin material.

Third wall 1528 and first wall 1504 may in some embodiments be made from a material that is permeable to at least some gasses. For example, third wall 1528 and first wall 1504 may be made of a material that has a relatively high permeability to water vapor but low penetration of liquid water, i.e., is water resistant. Furthermore, in other embodiments, third wall 1528 and first wall 1504 may also be made of a material that is biocompatible. Examples of possible materials for use in third wall 1528 and first wall 1504 include materials made from flashspun high-density polyethylene (HDPE) and polytetrafluoroethylene (PTFE). In one embodiment, third wall 1528 and first wall 1504 may include a non-woven textile that includes fibers made from flashspun HDPE. In another embodiment, third wall 1528 may include a cast polymer, cast on a non-woven textile.

In embodiments, third wall 1528 and first wall 1504 may have a water vapor transmission of greater than about 45 perms, greater than about 60 perms, greater than about 75 perms, greater than 90 perms, and even greater than about 105 perms. In some embodiments, third wall 1528 and first wall 1504 may have a water vapor permeability of between about 50 perms to about 900 perms, such as between about 100 perms and about 850 perms, or between about 150 perms and about 800 perms. Also, in some embodiments, the third wall 1528 and first wall 1504 may have a water resistance (i.e. hydrostatic head) of greater than about 75 cm, greater than 125 cm, greater than about 175 cm, and even greater than about 225 cm. In some embodiments, third wall 1528 and first wall 1504 may have a water resistance value of between about 25 cm to about 500 cm, such as between about 50 cm and about 400 cm, or between about 100 cm and about 300 cm. It is noted that in some embodiments, third wall 1528 and first wall 1504 may have any of the above-mentioned water vapor transmission values in combination with any of the above-mentioned water resistance values.

As shown in FIG. 15, first wall 1504 (and in some embodiments third wall 1528) may be attached to wall 1508 at one or more joints 1524. Therefore, in addition to other properties, first wall 1504 and second wall 1508 may also be made of materials that are compatible with each other to allow them to be attached together to form container 1500. The walls 1528, 1504, and 1508 may be attached together, in various combinations, using one or more suitable techniques, some non-limiting examples including heat sealing, ultrasonic welding, RF welding, solvent welding, laser welding, adhesive bonding, and/or combinations thereof.

It is noted that in some embodiments, third wall 1528 and first wall 1504 may be made from the same or similar material and/or materials with similar properties, non-limiting examples including thickness, tear strength, toughness, water vapor transmission, water resistance, etc. However, in other embodiments, third wall 1528 and first wall 1504 may differ in properties. For example, in some embodiments, third wall 1528 may be thicker than first wall 1504 in order to provide additional robustness to container 1500. In other embodiments, third wall 1528 may have a higher water vapor transmission, so that water vapor transported through first wall 1504 is more easily transported through third wall 1528 and into the environment. As yet another example, third wall 1528 may have a higher water resistance as well as be a more effective barrier against microorganisms in order to prevent water from seeping into volume 1540 and maintain the sterility of volume 1540.

Although not shown, in embodiments, container 1500 may include a fourth wall above third wall 1528. The fourth wall may be added as an additional layer of protection. Similar to third layer 1404 of container 1400, the fourth layer may prevent damage to third wall 1528 that may occur when handling container 1500, and also avoids any direct contact of hands or other objects with third wall 1528.

Figure 16:
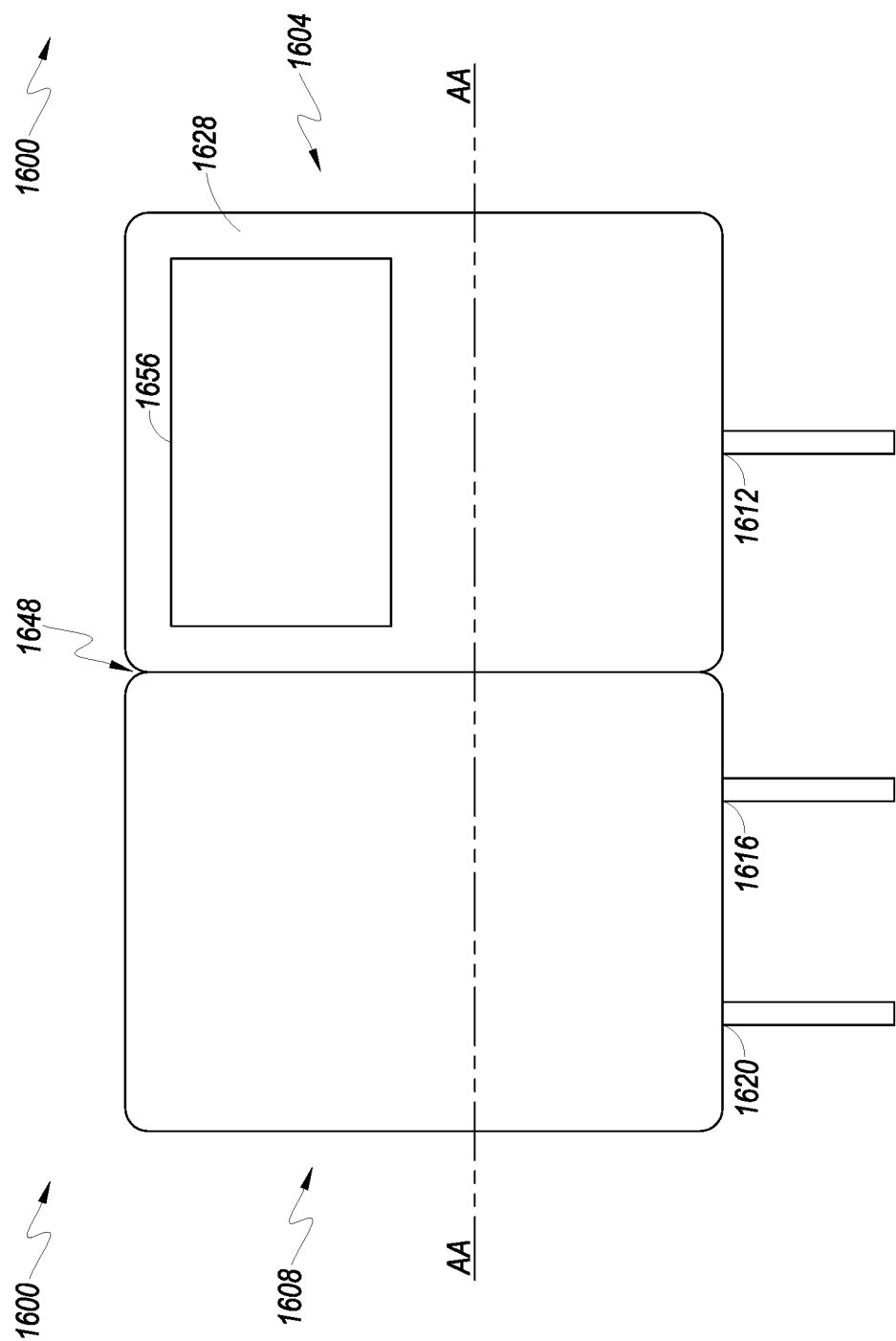
FIG. 16 illustrates a container that may be used to store material for lyophilization and after lyophilization according to embodiments.
Figure 17A:
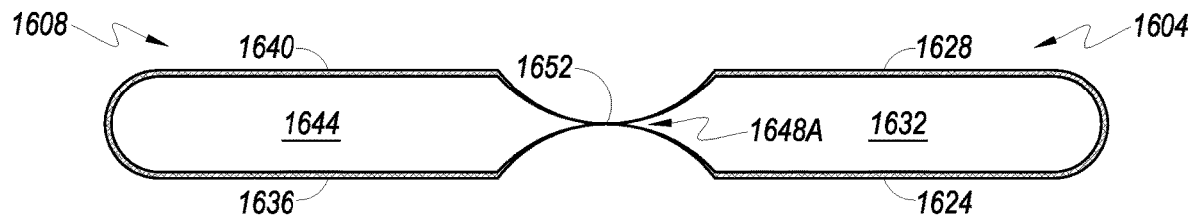
FIGS. 17A-17C illustrate cross sections of the container illustrated in FIG. 16.
Figure 17B:
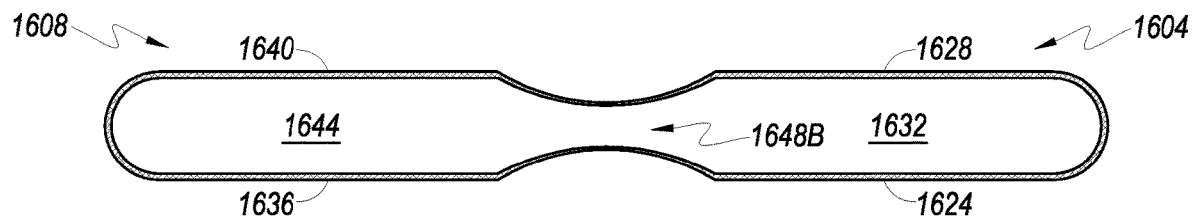
Figure 17C:
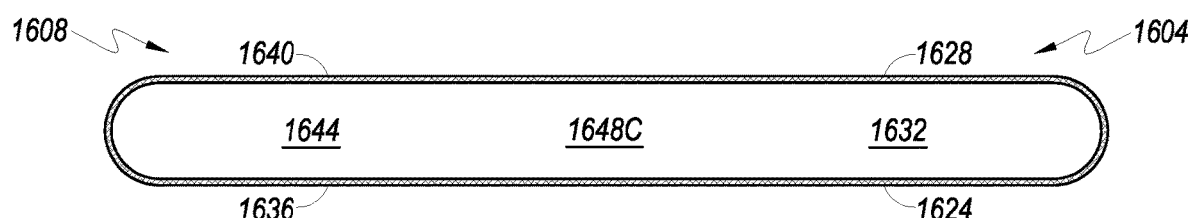

FIGS. 16-17C illustrate embodiments of a container 1600 that may be used to store material for lyophilization and after lyophilization. FIG. 16 illustrates a front view of container 1600. FIGS. 17A-17C illustrate various cross-sectional views of container 1600 taken at line AA (shown in FIG. 16). In some embodiments, container 1600 may be used to lyophilize a biological fluid such as whole blood or a blood component. However, embodiments of the present invention are not limited thereto. Any material, liquid or solid, may be lyophilized and stored using embodiments of container 1600.

As illustrated in FIG. 16, container 1600 includes a first chamber 1604 and a second chamber 1608. As described below, in the embodiment shown in FIGS. 16-17C, chamber 1604 may be used during lyophilization of a material, with chamber 1608 used to store the lyophilized material until it is rehydrated and used. Other embodiments may provide for different structures, designs, or components, which may include a first chamber for storing material during lyophilization and a second chamber for storing material after lyophilization.

First chamber 1604 includes a port 1612 through which material, such as blood or a blood component (e.g., human plasma), may enter chamber 1604. Chamber 1608 includes a port 1616 through which a hydration fluid may enter chamber 1608. Chamber 1608 also includes a port 1620 through which a rehydrated material may exit chamber 1608, e.g., a rehydrated blood component such as plasma may exit through port 1620 and be infused into a patient.

Referring to FIGS. 17A-17C, chamber 1604 includes a first wall 1624 and a second wall 1628, which is attached to the first wall, forming an interior volume 1632 of chamber 1604. As noted above, chamber 1604 may be used to store material during lyophilization; the material for lyophilization may be stored in volume 1632.

First wall 1624 in embodiments may be made from flexible polymeric materials. In some embodiments, wall 1624 may be made from transparent or translucent polymeric materials, non-limiting examples including polycarbonate, acrylics, polystyrene, polysulfone, polyethylene, polyolefin, polypropylene, polyvinylchloride, or combinations thereof.

As shown in FIG. 16, second wall 1628 may in embodiments include a region 1656 that has a permeability to a gas that is greater than the permeability of the first wall 1624. Because chamber 1604 is used to store material during lyophilization, the region 1656 is provided to allow a gas, e.g., water vapor, to escape volume 1632 during lyophilization.

Region 1656 may in embodiments be made from materials that have relatively high permeability to a gas, such as water vapor but are still robust enough to hold the material without leaking. In some embodiments, region 1656 may be made from one or more of the following materials: flashspun high-density polyethylene (HDPE), polytetrafluoroethylene (PTFE), acrylics cast on woven or nonwoven textiles, amides cast on woven or nonwoven textiles, and/or combinations thereof.

In some embodiments, region 1656 may be larger than shown in FIG. 16, such as making up more than half of wall 1628. In other embodiments, the entire wall 1628 may be made from a material that is permeable to gas, such as water vapor. In these embodiments, there would be no region 1656; instead, the entire wall 1628 would provide the region allowing gas, e.g., water vapor, to escape volume 1632. In yet other embodiments, there may be several regions 1656 of the same or different sizes as part of wall 1628.

The remaining portions of wall 1628 (and in embodiments also wall 1624), may be made from any suitable material. In embodiments, wall 1628 and/or wall 1624 may be made from flexible polymeric materials. Examples of flexible polymeric materials that may be used in portions of wall 1628 and in wall 1624 include without limitation: polycarbonate, acrylics, polystyrene, polysulfone, polyethylene, polyolefin, polypropylene, polyvinylchloride, or combinations thereof.

As noted above, container 1600 also has chamber 1608, which include a first wall 1636 that is attached to a second wall 1640 to define an interior volume 1644. In embodiments, chamber 1608 is designed to store material (e.g., whole blood or a blood component) after lyophilization. Walls 1636 and 1640 may therefore in embodiments be made from flexible polymeric materials that are robust and can withstand long storage periods and significant handling. In some embodiments, walls 1636 and 1640 may be made from transparent or translucent polymeric materials, non-limiting examples including polycarbonate, acrylics, polystyrene, polysulfone, polyethylene, polyolefin, polypropylene, polyvinylchloride, or combinations thereof.

In addition to chambers 1604 and 1608, container 1600 also has a pathway 1648, shown in FIGS. 17A, 17B, and 17C as 1648A, 1648B, and 1648C respectively. Pathway 1648 allows volumes 1632 and 1644 to be in communication, e.g., fluid communication, but may also be sealed with a seal 1652 to prevent communication between volumes 1632 and 1644.

FIG. 17A illustrates pathway 1648A sealed by seal 1652. In this embodiment, there is no communication, e.g., fluid communication, between volumes 1632 and 1644. This embodiment may be used when material in chamber 1604 is being lyophilized. Seal 1652 would prevent material, e.g., liquid or solid, from entering volume 1644. Maintaining the material in volume 1632 may make the lyophilization process more efficient because wall 1628 (which defines volume 1632) includes region 1656 through which gas, e.g., water vapor, escapes.

Seal 1652 may be created using any suitable material, mechanism, or process. Some non-limiting examples of seals that may be used as seal 1652 include welds, adhesives, frangibles, clamps, bonds, and/or combinations thereof. Creation of seal 1652 may involve mechanical clamping, welding (e.g., radio frequency, ultrasonic, induction, laser, etc.), heat sealing, adhesives, or other means. In embodiments, the seal 1652 may be opened to allow communication between volumes 1632 and 1644.

FIG. 17B illustrates pathway 1648B as open to allow communication between volume 1632 and 1644. Similarly, FIG. 17C illustrates pathway 1648C as open to allow communication between volume 1632 and 1644. FIGS. 17B and 17C illustrate two different embodiments where the pathway 1648 is opened different amounts, but both allowing material to flow from volume 1632 to volume 1644. It is noted that depending on the seal type, pathway 1648 may be opened to different extents.

The embodiments shown in FIGS. 17B and 17C may be used after a lyophilization process has been completed. Lyophilized material in volume 1632 may be transferred though pathway 1648B or 1648C into volume 1644. After the material is transferred, pathway 1648B or 1648C may be sealed again to prevent material from flowing back into volume 1632. In some embodiments, chamber 1604 may be removed after the lyophilized material is transferred into volume 1644 and pathway 1648B or 1648C is sealed. As one example, seal 1652 may be created by welding wall 1636 to 1640 and at the same time cutting walls 1624 and 1628 to separate chamber 1604 from chamber 1608.

Below is a description of a process according to embodiments of the present invention that provide for lyophilizing and storing whole blood or blood components, such as plasma. However, the present invention is not limited thereto and may be used to lyophilize and store other materials. Also, the description below may refer to specific features of container 1600 shown in FIGS. 16-17C, however the present invention is not limited to being performed by any particular structure and may utilize different features in other embodiments.

In embodiments, a liquid plasma product may be placed into a container, such as container 1600. More specifically, the plasma product may be placed into the chamber 1604 through port 1612. Chamber 1604 may provide a sterile barrier as well as allow the lyophilization of the plasma with water vapor escaping through a wall, such as through region 1656.

After a volume of liquid plasma is placed in chamber 1604, container 1600 may be placed in an apparatus for lyophilizing materials, such as apparatus 100 (FIG. 1) or apparatus 200 (FIG. 2). The liquid plasma may undergo a lyophilization process.

It is noted that during the lyophilization of the plasma, a seal, such as seal 1652 may be in the pathway 1648, which prevents communication between the volumes of chambers 1604 and 1608. That is, there may be no fluid communication between the volumes 1632 and 1644.

After the lyophilization of the plasma, container 1600 may be removed from the lyophilization apparatus. Seal 1652 may be removed/opened to allow communication through pathway 1648. The lyophilized plasma may then be transferred from volume 1632 into volume 1644. Seal 1652 may then be closed or resealed. In some embodiments, chamber 1604 may be removed from chamber 1608 after, or as part of resealing pathway 1648.

Chamber 1608 may be designed in some embodiments to be robust and made from materials that withstand the rigors of being significantly handled, e.g., carried in a backpack in a military environment or handling in mobile use such as an ambulance (helicopter or vehicle). Accordingly, the lyophilized plasma may be stored in chamber 1608 for relatively large periods of time until it is used, e.g., rehydrated and infused into a patient.

In some embodiments, before the lyophilized plasma is used, a rehydration liquid may be transferred into chamber 1608 through port 1616. After some time to hydrate the plasma (e.g., less than five minutes), the rehydrated plasma may be infused into a patient through port 1620.

In the embodiments where plasma is lyophilized, stored and transfused using container 1600, the two chambers 1604 and 1608, as well as other portions of the container, may be maintained sterile and remain a "closed" system throughout the process of filling, lyophilizing, transferring between chambers, storing, and using.

FIGS. 18A and 18B illustrate a front view of another container 1800 consistent with embodiments of the present invention. In the embodiment shown in FIGS. 18A and 18B, container 1800 initially has a single chamber 1804 with an interior volume 1808. Container 1800 includes a first portion 1804A (e.g., top portion) and a second portion 1804B (e.g., bottom portion).

Container 1800 includes a first wall (not shown) and a second wall 1828, which is attached to the first wall, forming an interior volume 1808 of chamber 1804. The first wall in embodiments may be made from flexible polymeric materials. In some embodiments, the first wall may be made from transparent or translucent polymeric materials, non-limiting examples including polycarbonate, acrylics, polystyrene, polysulfone, polyethylene, polyolefin, polypropylene, polyvinylchloride, or combinations thereof.

As illustrated in FIG. 18A, the top portion of wall 1828 includes a gas permeable region 1856 that allows a gas, such as water vapor, to escape volume 1808. The bottom portion of wall 1828 does not include a gas permeable region.

Region 1856 has a permeability to a gas that is greater than the permeability of the first wall and the remaining portion of second wall 1828. Region 1856 may be provided to allow a gas, e.g., water vapor, to escape volume 1808 during lyophilization.

Region 1856 may in embodiments be made from materials that have relatively high permeability to a gas, such as water vapor but are still robust enough to hold material to be lyophilized without leaking. In some embodiments, region 1856 may be made from one or more of the following materials: flashspun high-density polyethylene (HDPE), polytetrafluoroethylene (PTFE), acrylics cast on woven or nonwoven textiles, amides cast on woven or nonwoven textiles, and/or combinations thereof. The remaining portions of wall 1828 may be made from any suitable material. In embodiments, portions of second wall 1828 may be made from a flexible polymeric material. Examples of flexible polymeric materials that may be used in portions of wall 1828 include without limitation: polycarbonate, acrylics, polystyrene, polysulfone, polyethylene, polyolefin, polypropylene, polyvinylchloride, or combinations thereof.

In embodiments of using container 1800, material to be lyophilized may be transferred into volume 1808 through one or more of ports 1816 and/or 1820. After the material has been lyophilized, the lyophilized material may be moved, manually or automatically (e.g., by a mechanical system), within chamber 1804 so that most of the lyophilized material is in the bottom portion 1804B. After the lyophilized material has been moved to bottom portion 1804B, the bottom portion 1804B may be separated from top portion 1804A, as shown in FIG. 18B.

As part of the separation, or before the separation of portions 1804A and 1804B, a seal 1860 may be created on a top edge of bottom portion 1804B. The seal 1860 may ensure that the lyophilized material is maintained in a sterilized environment through-out the process of separating the bottom portion 1804B from the top portion 1804A. In embodiments, seal 1860 may be created using any suitable sealing device. Non-limiting examples of devices that may be used in embodiments to create seal 1860 as well as separate bottom portion 1804B from top portion 1804A, include without limitation: ultrasonic welders, laser welders, radio frequency welders, high frequency welders, induction welders, hot bar welders, impulse welders, hot gas welders, infrared welders, and/or microwave welders.

Bottom portion 1804B may be designed in some embodiments to be robust and made to withstand the rigors of being significantly handled, e.g., carried in a backpack in a military environment or handling in mobile use such as an ambulance (helicopter or vehicle). Accordingly, the lyophilized material may be stored in bottom portion 1804B until it is used.

In some embodiments, before the lyophilized material in bottom portion 1804B is used, a rehydration liquid may be transferred into bottom portion 1804B through one or more ports 1816 and/or 1820. After some time to hydrate the material, the material may be used and transferred out of bottom portion 1804B through one or more ports 1816 and/or 1820.

FIGS. 19A-19C illustrates a side view of another embodiment of a container 1900 that may be used to store material for lyophilization and after lyophilization. Container 1900 includes a first chamber 1904 and a second chamber 1908. As described below, chamber 1904 may be used in embodiments during lyophilization of a material with chamber 1908 being used to store the lyophilized material after lyophilization.

First chamber 1904 includes a port 1912 through which material, e.g. plasma, whole blood, or other blood component, may be introduced into chamber 1904. In addition, chamber 1904 include a first wall 1916 attached to a second wall 1920 through a side wall 1924 to form an interior volume of chamber 1904. It is noted that in some embodiments, side wall 1924, or a portion thereof, may be part of first wall 1916 or second wall 1920. For example, in embodiments first wall 1916 and/or second wall 1920 may be formed from a sheet with dimensions that allow the sheet to be folded to create side wall 1924 or a portion of side wall 1924. In other embodiments, wall 1920 may be in the form of a tray that includes side walls 1924. In embodiments, side wall 1924 extends between first wall 1916 and second wall 1920 along a perimeter of first wall 1916 and second wall 1920.

As shown in FIGS. 19A and 19B, side wall 1924 includes creases 1928A, 1928B, and 1928C, which allow side wall 1924 to collapse and expand. FIG. 19A illustrates side wall 1924 collapsed, which provides less volume within the interior volume of chamber 1904. FIG. 19B illustrates side wall 1924 in an expanded state, which provides greater volume within the interior volume of chamber 1904.

As shown in FIG. 19B, chamber 1904 is connected to chamber 1908 through a pathway 1932. In FIG. 19A, clip 1936 is positioned to close and/or seal pathway 1932 to avoid communication between chamber 1904 and 1908.

Referring back to chamber 1904, wall 1920 and/or side wall 1924 may, in embodiments, be made from flexible polymeric materials. In some embodiments, wall 1920 and/or side wall 1924 may be made from transparent or translucent polymeric materials, non-limiting examples including polycarbonate, acrylics, polystyrene, polysulfone, polyethylene, polyolefin, polypropylene, polyvinylchloride, or combinations thereof.

Wall 1916 may include materials that are permeable to a gas. That is, wall 1916 may include material that has a greater permeability to a gas (e.g., water vapor) than the permeability of wall 1920. Because chamber 1904 is used to store material during lyophilization, the permeable material is provided to allow a gas, e.g., water vapor, to escape chamber 1904 during lyophilization. In embodiments, the entire wall 1916 may be made of a gas permeable material. In other embodiments, only a region of wall 1916 may be include the permeable material, similar to wall 1828 of container 1800 (FIG. 18A).

The permeable materials that may be used in wall 1916 may in embodiments be made from materials that have relatively high permeability to a gas, such as water vapor but are still robust enough to hold the material without leaking. In some embodiments, wall 1916 may be made from one or more of the following materials: flashspun high-density polyethylene (HDPE), polytetrafluoroethylene (PTFE), acrylics cast on woven or nonwoven textiles, amides cast on woven or nonwoven textiles, and/or combinations thereof.

In embodiments, wall 1916 may have a water vapor transmission of greater than about 65 perms, greater than about 85 perms, greater than about 105 perms, greater than 125 perms, and even greater than about 145 perms. In some embodiments, wall 1916 may have a water vapor permeability of between about 70 perms to about 825 perms, such as between about 95 perms and about 775 perms, or between about 120 perms and about 725 perms. Also, in some embodiments, the wall 1916 may have a water resistance (i.e. hydrostatic head) of greater than about 70 cm, greater than about 85 cm, greater than about 100 cm, and even greater than about 115 cm. In some embodiments, wall 1916 may have a water resistance value of between about 20 cm to about 525 cm, such as between about 25 cm and about 500 cm, or between about 30 cm and about 475 cm. It is noted that in some embodiments, wall 1916 may have any of the above-mentioned water vapor transmission values in combination with any of the above-mentioned water resistance values.

In those embodiments where wall 1916 includes only a portion of permeable material, the remaining portions may be made from any suitable material. Examples of flexible polymeric materials that may be used in portions of wall 1916 include without limitation: polycarbonate, acrylics, polystyrene, polysulfone, polyethylene, polyolefin, polypropylene, polyvinylchloride, or combinations thereof.

As noted above, container 1900 also has chamber 1908, which includes a first wall 1940 that is attached to a second wall 1944 to define an interior volume of chamber 1908 (see FIGS. 19B & 19C). In embodiments, chamber 1908 is designed to store material (e.g., whole blood or a blood component) after lyophilization. Walls 1940 and 1944 may therefore in embodiments be made from flexible polymeric materials that are robust and can withstand long storage periods and significant handling. In some embodiments, walls 1940 and 1944 may be made from transparent or translucent polymeric materials, non-limiting examples including polycarbonate, acrylics, polystyrene, polysulfone, polyethylene, polyolefin, polypropylene, polyvinylchloride, or combinations thereof.

Chamber 1908 also includes a port 1948. In embodiments, port 1948 may be used to remove material from chamber 1908. In one embodiment, lyophilized material within chamber 1908 may be rehydrated in chamber 1908 and then removed from chamber 1908 through port 1948. As one example, lyophilized plasma may be stored within chamber 1908. After adding a rehydrating liquid to the lyophilized plasma, the rehydrated plasma may be infused into a patient through port 1948. In other embodiments, chamber 1908 may include more than one port. In these embodiments, port 1948 may be used to introduce reconstitution fluid to rehydrate the lyophilized plasma, with the other port being used to infuse the reconstituted plasma to a patient.

In FIG. 19A, chamber 1908 is rolled up so that it does not take up as much space as when it is extended as shown in FIG. 19B. The ability of chamber 1908 to be rolled up (FIG. 19A) allows container 1900 to take up less shelf space in a lyophilization apparatus (e.g., 100 or 200), for example. If chamber 1908 could not be rolled up, then container 1900 would take up shelf space that could be used to lyophilize additional material.

In addition to chambers 1904 and 1908, container 1900 also has a pathway 1932. Pathway 1932 allows volumes 1904 and 1908 to be in communication, e.g., fluid communication, but may also be sealed with a seal to prevent communication between volumes 1904 and 1908.

FIG. 19A illustrates pathway 1932 sealed by clip 1936. In this embodiment, there is no communication, e.g., fluid communication, between volumes 1904 and 1908. This embodiment may be used when material in chamber 1904 is being lyophilized. Clip 1936 prevents material that may be in chamber 1904, e.g., liquid or solid, from entering the volume of chamber 1908. Maintaining the material in volume 1904 may make the lyophilization process more efficient because wall 1916 includes a gas permeable material which allows gas, e.g., water vapor, to escape. If material were allowed to migrate into chamber 1908, any gas would have to travel to chamber 1904 to escape through wall 1916, which may prolong the lyophilization process.

In other embodiments, instead of clip 1936, the seal between chamber 1904 and 1908 may be created using any suitable material, mechanism, or process. Some non-limiting examples of seals that may be used instead of clip 1936 include welds, adhesives, frangibles, bonds, and/or combinations thereof. Creation of a seal between chambers 1904 and 1908 may involve mechanical clamping, welding (e.g., radio frequency, ultrasonic, induction, laser, etc.), heat sealing, adhesives, and/or other means.

FIG. 19B illustrates clip 1936 removed, and pathway 1932 open to allow communication between volume 1904 and 1908. The clip 1936 may be removed and pathway 1932 opened after material has been lyophilized in chamber 1904. With pathway 1932 open, the lyophilized material may then be transferred from chamber 1904 to chamber 1908 for longer term storage.

After the lyophilized material has been transferred into chamber 1908, chamber 1904 and chamber 1908 may be sealed again to prevent communication between the two chambers. As shown in FIG. 19C chamber 1904 may be separated from chamber 1908 with chamber 1908 being sealed with seal 1952. Chamber 1908 may then be used to store the lyophilized material for a relatively long period of time, e.g., about two years.

In embodiments of using container 1900, material to be lyophilized may be transferred into volume 1904 through port 1912 in one embodiment it may be plasma. As a result of introducing the plasma into chamber 1904, side wall 1924 may utilize creases 1928A-C to expand the volume of chamber 1904 (see chamber 1904 in FIG. 19B). While chamber 1908 is still in a rolled up state (see chamber 1908 in FIG. 19A), container 1900 may be place in a lyophilization apparatus such as apparatus 100 (FIG. 1) or apparatus (FIG. 2) and have the plasma lyophilized. As noted above, the lyophilization process may involve steps such as exposing the material and container 1900 to a first pressure below atmospheric pressure, freezing, and sublimating a component of the material. Gasses generated during the sublimation process may escape chamber 1904 through the gas permeable material of wall 1916.

After the material has been lyophilized, the lyophilized material may be moved, manually or automatically (e.g., by a mechanical system), from chamber 1904 to chamber 1908. Initially, clip 1936 is removed, which allows communication between chamber 1904 and 1908. The lyophilized material may then be moved to chamber 1908. Chamber 1908 may be sealed and chamber 1904 may then be separated from chamber 1908, as shown in FIG. 19C.

As part of the separation, or before the separation of chamber 1904 and 1908, a seal 1952 may be created on an end of chamber 1908. The seal 1952 may ensure that the lyophilized material is maintained in a sterilized environment through-out the process of separating the chamber 1904 and chamber 1908. In embodiments, seal 1952 may be created using any suitable sealing device. Non-limiting examples of devices that may be used in embodiments to create seal 1952 as well as separate chamber 1904 and chamber 1908, including without limitation: ultrasonic welders, laser welders, radio frequency welders, high frequency welders, induction welders, hot bar welders, impulse welders, hot gas welders, infrared welders, and/or microwave welders.

Figure 20A:
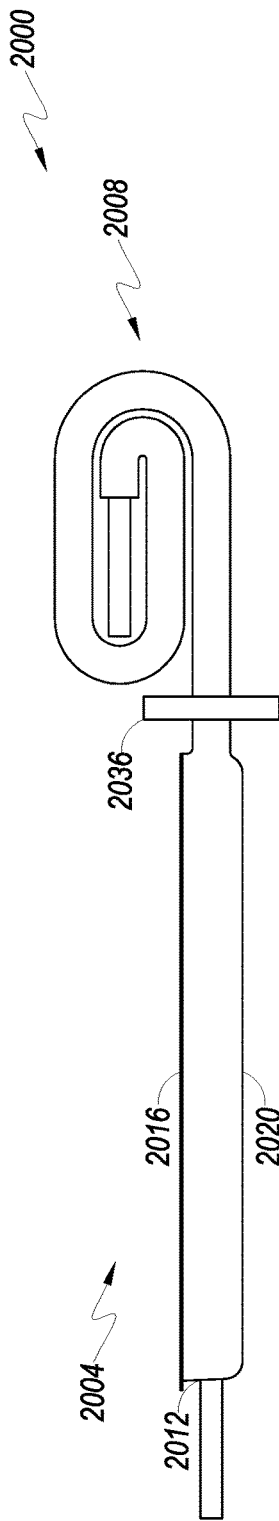
FIGS. 20A-20C illustrate a container that may be used to store material for lyophilization and after lyophilization according to yet other embodiments.
Figure 20B:
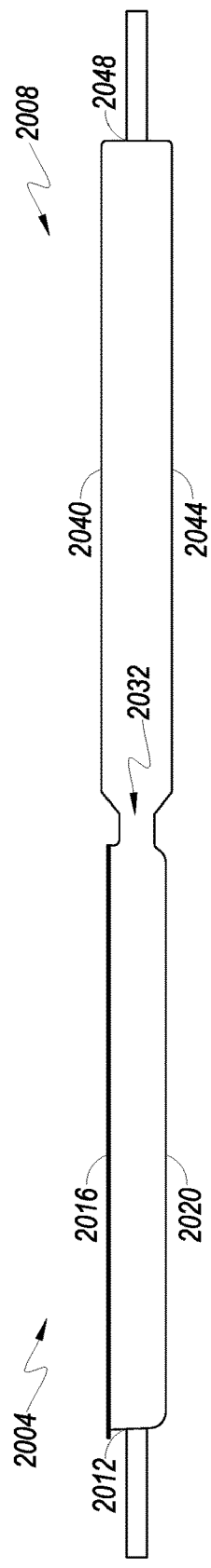
Figure 20C:
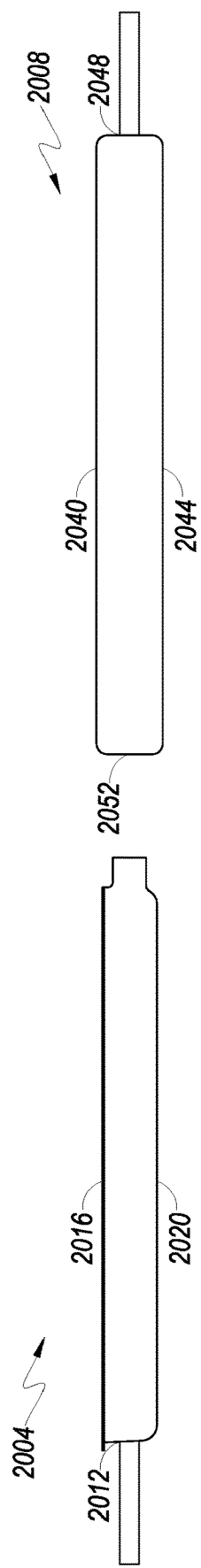

FIGS. 20A-20C illustrates a side view of another embodiment of a container 2000 that may be used to store material for lyophilization and after lyophilization. Container 2000 includes a first chamber 2004 and a second chamber 2008. As described below, chamber 2004 may be used in embodiments during lyophilization of a material with chamber 2008 being used to store the lyophilized material for storage until it is rehydrated and used.

First chamber 2004 includes a port 2012 through which material, e.g. plasma, whole blood, or other blood component, may be introduced into chamber 2004. In addition, chamber 2004 includes a first wall 2016 attached to a second wall 2020 to form an interior volume of chamber 2004. It is noted that in some embodiments, wall 2020 may provide some depth for material that is stored in container chamber 2004. In these embodiments, wall 2020 may be in the form of a tray.

As shown in FIG. 20B, chamber 2004 is connected to chamber 2008 through a pathway 2032. In FIG. 20A, clip 2036 is positioned to close and/or seal pathway 2032 to avoid communication between chamber 2004 and 2008.

Referring back to chamber 2004, wall 2020, in embodiments, may be made from flexible polymeric materials. In some embodiments, wall 2020 may be made from transparent or translucent polymeric materials, non-limiting examples including polycarbonate, acrylics, polystyrene, polysulfone, polyethylene, polyolefin, polypropylene, polyvinylchloride, or combinations thereof.

Wall 2016 may include materials that are permeable to a gas. Wall 2016 may include material that has a greater permeability to a gas (e.g., water vapor) than the permeability of wall 2020. Because chamber 2004 is used to store material during lyophilization, the permeable material is provided to allow a gas, e.g., water vapor, to escape chamber 2004 during lyophilization. In embodiments, the entire wall 2016 may be made of a gas permeable material. In other embodiments, only a region of wall 2016 may be made of the permeable material, similar to wall 1828 of container 1800 (FIG. 18A).

The permeable materials that may be used in wall 2016 may in embodiments be made from materials that have relatively high permeability to a gas, such as water vapor but are still robust enough to hold the material without leaking. In some embodiments, wall 2016 may be made from one or more of the following materials: flashspun high-density polyethylene (HDPE), polytetrafluoroethylene (PTFE), acrylics cast on woven or nonwoven textiles, amides cast on woven or nonwoven textiles, and/or combinations thereof.

In embodiments, wall 2016 may have a water vapor transmission of greater than about 135 perms, greater than about 150 perms, greater than about 165 perms, greater than 180 perms, and even greater than about 195 perms. In some embodiments, wall 2016 may have a water vapor permeability of between about 115 perms to about 725 perms, such as between about 130 perms and about 700 perms, or between about 145 perms and about 675 perms. Also, in some embodiments, the wall 2016 may have a water resistance (i.e. hydrostatic head) of greater than about 80 cm, greater than about 90 cm, greater than about 100 cm, and even greater than about 110 cm. In some embodiments, wall 2016 may have a water resistance value of between about 20 cm to about 500 cm, such as between about 30 cm and about 450 cm, or between about 40 cm and about 400 cm. It is noted that in some embodiments, wall 2016 may have any of the above-mentioned water vapor transmission values in combination with any of the above-mentioned water resistance values.

In those embodiments where wall 2016 includes only a portion of permeable material, the remaining portions may be made from any suitable material. Examples of flexible polymeric materials that may be used in portions of wall 2016 include without limitation: polycarbonate, acrylics, polystyrene, polysulfone, polyethylene, polyolefin, polypropylene, polyvinylchloride, or combinations thereof.

As noted above, container 2000 also has chamber 2008, which include a first wall 2040 that is attached to a second wall 2044 to define an interior volume of chamber 2008 (see FIG. 20B). In embodiments, chamber 2008 is designed to store material (e.g., whole blood or a blood component) after lyophilization. Walls 2040 and 2044 may therefore in embodiments be made from flexible polymeric materials that are robust and can withstand long storage periods and significant handling. In some embodiments, walls 2040 and 2044 may be made from transparent or translucent polymeric materials, non-limiting examples including polycarbonate, acrylics, polystyrene, polysulfone, polyethylene, polyolefin, polypropylene, polyvinylchloride, or combinations thereof.

Chamber 2008 also includes a port 2048. In embodiments, port 2048 may be used to remove material from chamber 2008. In one embodiment, lyophilized material within chamber 2008 may be rehydrated in chamber 2008 and then removed from chamber 2008 through port 2048. As one example, lyophilized plasma may be stored within chamber 2008. After adding a rehydrating liquid to the lyophilized plasma, the rehydrated plasma may be infused into a patient through port 2048. In other embodiments, chamber 2008 may include more than one port. In these embodiments, port 2048 may be used to introduce reconstitution fluid to rehydrate the lyophilized plasma, with the other port being used to infuse the reconstituted plasma to a patient.

In FIG. 20A, chamber 2008 is rolled up so that it does not take up as much space as when it is extended as shown in FIG. 20B. The ability of chamber 2008 to be rolled up (FIG. 20A) allows container 2000 to take up less shelf space in a lyophilization apparatus (e.g., FIG. 1 or FIG. 2), for example. If chamber 2008 could not be rolled up, then container 2000 would take up shelf space that could be used to lyophilize additional material.

In addition to chambers 2004 and 2008, container 2000 also has a pathway 2032. Pathway 2032 allows volumes 2004 and 2008 to be in communication, e.g., fluid communication, but may also be sealed with a seal to prevent communication between volumes 2004 and 2008.

FIG. 20A illustrates pathway 2032 sealed by clip 2036. In this embodiment, there is no communication, e.g., fluid communication, between volumes 2004 and 2008. This embodiment may be used when material in chamber 2004 is being lyophilized. Clip 2036 prevents material that may be in chamber 2004, e.g., liquid or solid, from entering the volume of chamber 2008. Maintaining the material in volume 2004 may make the lyophilization process more efficient because wall 2016 includes a gas permeable material which allows gas, e.g., water vapor, to escape.

In other embodiments, instead of clip 2036, the seal between chamber 2004 and 2008 may be created using any suitable material, mechanism, or process. Some non-limiting examples of seals that may be used instead of clip 2036 include welds, adhesives, frangibles, bonds, and/or combinations thereof. Creation of a seal between chambers 2004 and 2008 may involve mechanical clamping, welding (e.g., radio frequency, ultrasonic, induction, laser, etc.), heat sealing, adhesives, or other means.

FIG. 20B illustrates clip 2036 removed, and pathway 2032 open to allow communication between volume 2004 and 2008. The clip 2036 may be removed and pathway 2032 opened after material has been lyophilized in chamber 2004. With pathway 2032 open, the lyophilized material may then be transferred from chamber 2004 to chamber 2008 for longer term storage.

After the lyophilized material has been transferred into chamber 2008, chamber 2004 and chamber 2008 may be sealed again to prevent communication between the two chambers. As shown in FIG. 20C chamber 2004 may be separated from chamber 2008 with chamber 2008 being sealed with seal 2052. Chamber 2008 may then be used to store the lyophilized material for a relatively long period of time, e.g., about two years.

Figure 21:
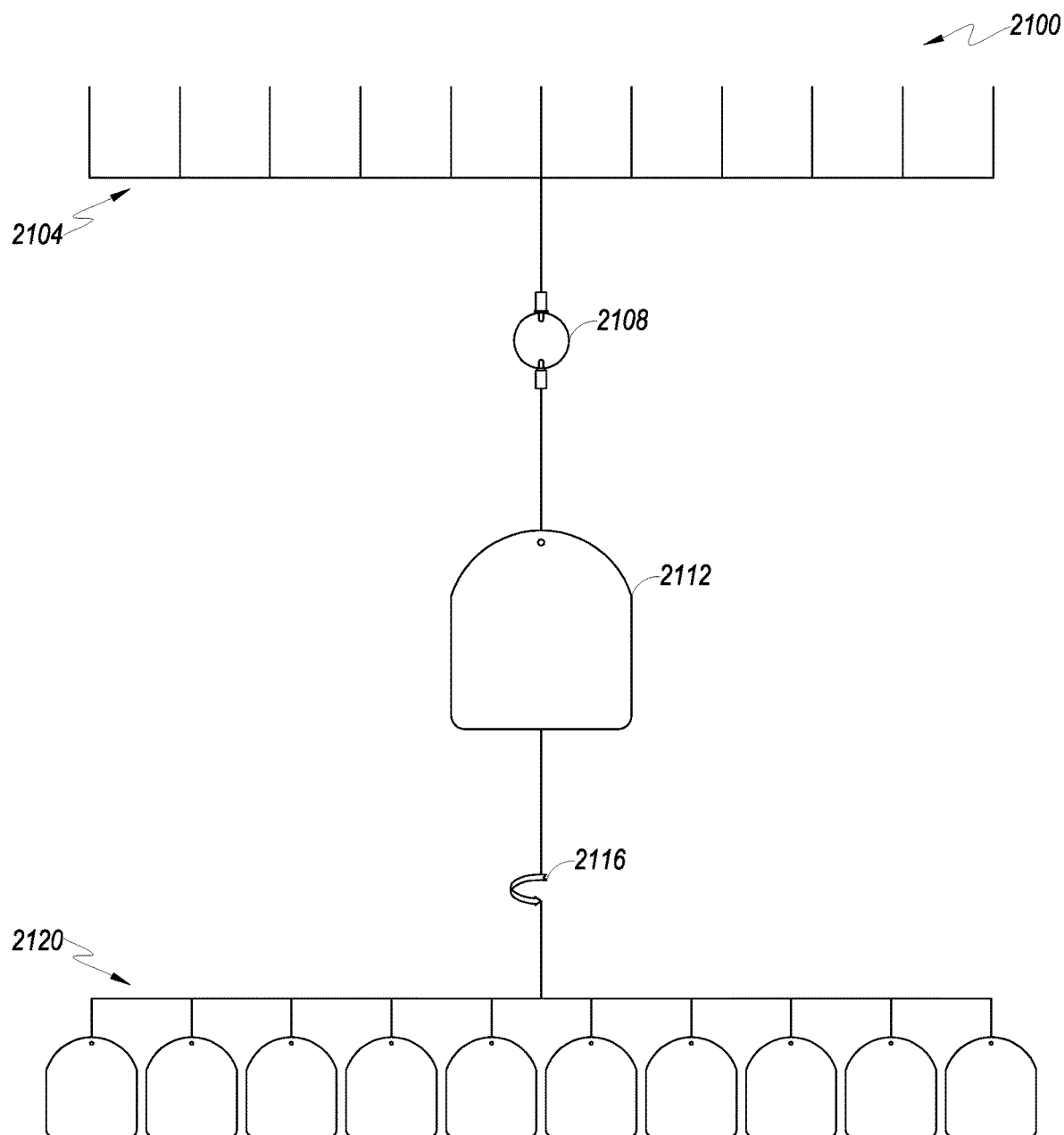
FIG. 21 illustrates an embodiment of a system for pooling and filling containers with a biological fluid for later lyophilizing.

Referring now to FIG. 21, an embodiment of a system 2100 for filling containers with a biological fluid is illustrated. In one embodiment, system 2100 is used to pool blood or blood components for later lyophilizing. In one embodiment, system 2100 is used to pool human plasma. The description below expands on the embodiment for pooling plasma; however it is noted that other embodiments may involve pooling other biological fluids.

System 2100 includes ports 2104 where a number of containers, e.g., bags, with plasma may be connected. The plasma may in embodiments come from different donors, with each bag containing plasma from a single donor. In some embodiments, the plasma may be selected based on the blood types of the donors. For example, the plasma may all be from donors of a single blood type or of compatible blood types. In one embodiment, the specific blood types of the donors may be selected to create a universal blood type. The use of plasma from donors with blood types, A, B, and AB may in embodiments be used to create universal plasma that may be infused into patients of any blood type.

After being connected to ports 2104, plasma may be passed through filter 2108, which may be used to remove some components or contaminants from the plasma. In one embodiment, filter 2108 is designed to remove cells, such as leukocytes, from the plasma. Although system 2100 illustrates only a single filter 2108, in other embodiments, system 2100 may include a series of filters each for filtering the same, or a different, component or contaminant from the plasma.

After filtering, the plasma is pooled together in container 2112, which in embodiments is a bag that can accommodate a relatively large volume of plasma, e.g., at least the volume of plasma in the containers connected to ports 2104. While in container 2112, the plasma may undergo agitation to mix the plasma. In these embodiments, system 2100 may include additional features that effect the agitation, non-limiting examples including, rollers, motors, ultrasonic transducers, power source(s), etc.

System 2100 may in embodiment rely on gravity to create the flow of plasma from, and to, different parts of system 2100. In other embodiments, pumps can be utilized to pump plasma from, and to, different parts of system 2100. In the specific embodiment shown in FIG. 21, pump 2116 is used to move plasma from container 2112 into containers 2120. It is noted that in other embodiments, pumps may be used in other parts of the system, for example, a pump may be used to move plasma from filter 2108 to container 2112.

Although containers 2120 may be any suitable container for holding plasma, embodiments, the containers are similar to container 1200 (FIGS. 12-13), 1600 (FIGS. 17-18), 1800 (FIG. 18), 1900 (FIG. 19), and/or 2000 (FIG. 20). As described in greater detail below, system 2100 may be used with containers 2120 in a process for pooling biological fluids (e.g., plasma), lyophilizing the fluids into a solid, storing the solid, reconstituting the solid into the biological fluid, and using the biological fluid in a patient.

Figure 22:
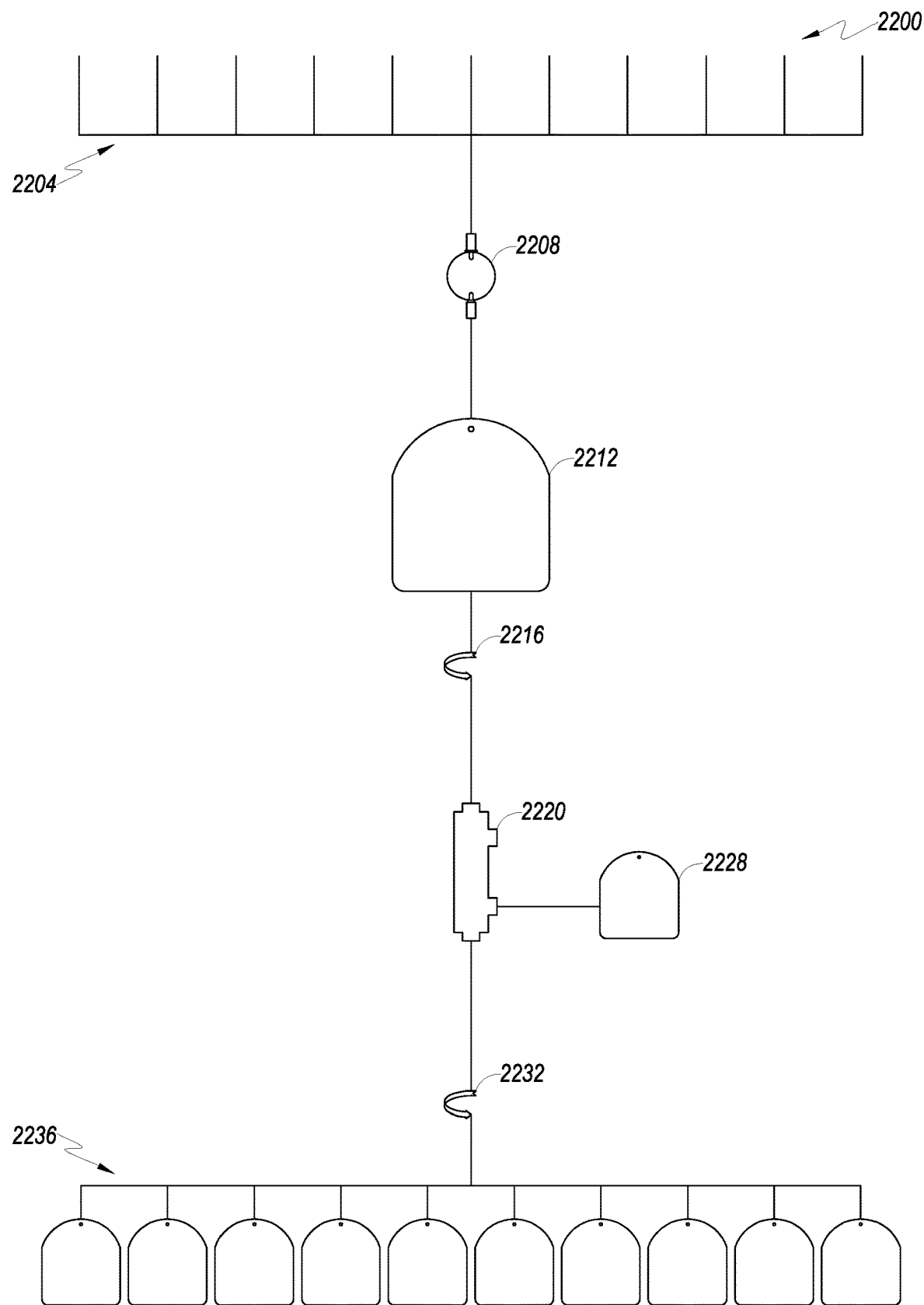
FIG. 22 illustrates an embodiment of a system for pooling a biological fluid, reducing a volume of the biological fluid, and filling containers with the biological fluid for later lyophilizing.

FIG. 22 illustrates a second embodiment of a system 2200 that may be used to pool and fill containers with a biological fluid. System 2200 includes similar features to system 2100 but also includes some additional features. Similar to system 2100, system 2200 includes ports 2204 where a number of containers, e.g., bags, with plasma may be connected. The plasma may in embodiments come from different donors, with each bag containing plasma from a single donor. As noted above, the plasma may be selected based on the blood types of the donors to create plasma for a single blood type or create universal plasma that may be infused into patients of any blood type.

Plasma flows from ports 2204 through filter 2208, which is similar to filter 2108 and may be used to remove some components or contaminants from the plasma, e.g., cells such as leukocytes. In other embodiments, system 2200 may include a series of filters each for filtering the same, or a different, component or contaminant from the plasma.

After filtering, the plasma is pooled together in container 2212, which in embodiments is a bag. System 2200 may include additional components that effect agitation of the plasma, not limiting examples including, rollers, motors, ultrasonic transducers, power source(s), etc.

System 2200 also includes pump 2216, in embodiments, which is used to move plasma from container 2212 into filter 2220. It is noted that in other embodiments, pumps may be used in other parts of the system, for example, a pump may be used to move plasma from filter 2208 to container 2212.

Filter 2220 may be used to concentrate the plasma by removing water and some salt from the plasma. In one embodiment, filter 2220 may be a hollow fiber membrane filter, which removes water, salt, and some lower molecular weight molecules from the plasma. The water, salt, and molecules from filter 2220 are collected in container 2228, where they may be stored for later use, or discarded. Although system 2200 illustrates only a single filter 2220, in other embodiments, system 2200 may include a series of filters each removing at least some water or other component from the plasma.

Pump 2232 is used to move plasma from filter 2220 into containers 2236. Although containers 2236 may be any suitable container for holding concentrated plasma, in embodiments, the containers may be similar to containers 1200 (FIGS. 12-13) 1600 (FIGS. 16-17C), 1800 (FIG. 18), 1900 (FIG. 19), and/or 2000 (FIG. 20). System 2200 may be used with the containers in processes for pooling biological fluids (e.g., plasma), lyophilizing the fluids into a solid, storing the solid, reconstituting the solid into the biological fluid, and using the biological fluid in a patient.

Figure 23:
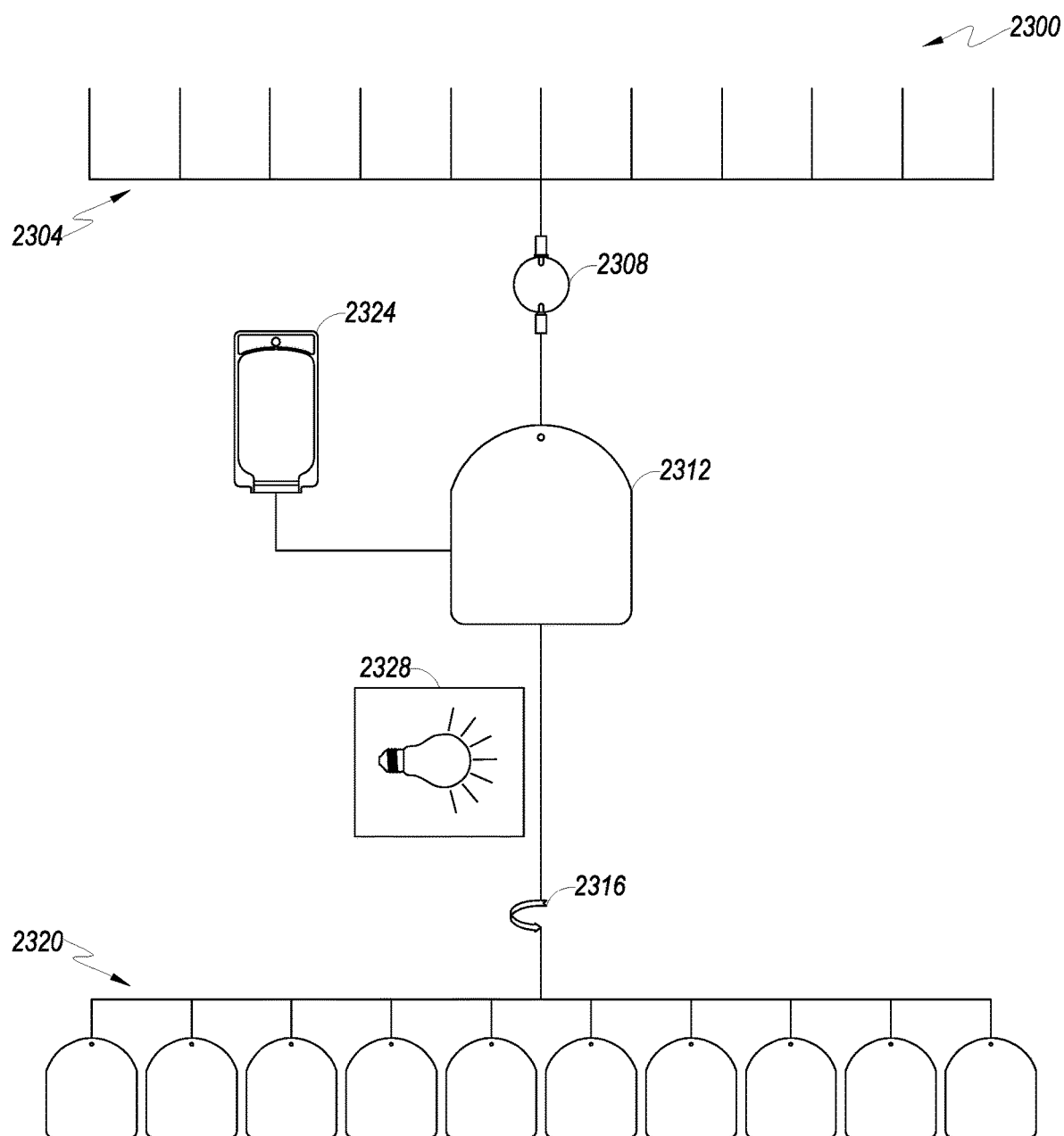
FIG. 23 illustrates an embodiment of a system for pooling a biological fluid, pathogen reducing the fluid, and filling containers with the biological fluid for later lyophilizing.

FIG. 23 illustrates an embodiment of a system 2300 for filling containers with a biological fluid. System 2300 is similar to system 2100 described above, however it includes additional pathogen reduction features. In embodiments, system 2300 is used to pool blood or blood components and pathogen reduce the blood or blood components prior to lyophilizing. In one embodiment, system 2200 is used to pool and pathogen reduce human plasma. The description below expands on the embodiment for pooling and pathogen reducing plasma; however it is noted that other embodiments may involve pooling other biological fluids.

System 2300 includes ports 2304 where a number of containers, e.g., bags, with plasma may be connected. The plasma may in embodiments come from different donors, with each bag containing plasma from a single donor. In some embodiments, the plasma may be selected based on the blood types of the donors. For example, the plasma may all be from donors of a single blood type or of compatible blood types. In one embodiment, the specific blood types of the donors may be selected to create a universal blood type. The use of plasma from donors with blood types, A, B, and AB may in embodiments be used to create universal plasma that may be infused into patients of any blood type.

After being connected to ports 2304, plasma may be passed through filter 2308, which may be used to remove some components or contaminants from the plasma. After filtering, the plasma may be pooled together in container 2312, which in embodiments is a bag that can accommodate a relatively large volume of plasma, e.g., at least the volume of plasma in the containers connected to ports 2304. While in container 2312, the plasma may undergo agitation to mix the plasma. In these embodiments, system 2300 may include additional features that effect the agitation, non-limiting examples including, rollers, motors, ultrasonic transducers, power source(s), etc.

System 2300 may in embodiment rely on gravity to create the flow of plasma from, and to, different parts of system 2300. In other embodiments, pumps can be utilized to pump plasma from, and to, different parts of system 2300. For example, pump 2316, may be used to pump plasma from container 2324 to containers 2320.

System 2300 also includes a container 2324 that stores a photosensitizer that may be used in pathogen reducing the plasma pooled in container 2312. In embodiments, container 2324 may store an endogenous photosensitizer non-limiting examples including flavins such as riboflavin.

Container 2312 may be made from materials that are transparent or at least translucent to the wavelength of light used in the pathogen reduction process. In some embodiments, container 2312 may be made of flexible polymeric materials that are transparent or at least translucent to light of wavelengths between about 250 nm to about 600 nm.

After the plasma is pooled together in container 2312, the photosensitizer may be mixed into the plasma in container 2312. System 2300 may include additional components that effect agitation of the plasma and photosensitizer, not limiting examples including, rollers, motors, ultrasonic transducers, power source(s), etc.

After the photosensitizer has been mixed into the plasma in container 2312, the plasma may be exposed to a light source such as light source 2328. In embodiments, light source 2328 may be of a wavelength that interacts with the photosensitizer to pathogen reduce the plasma. Examples and further description of pathogen reduction, which may be used in embodiments, including combinations of light wavelengths and photosensitizers, are provided in U.S. Pat. Nos. 6,548,241; 6,258,577; and 6,277,337, which are all hereby incorporated by reference in their entirety as if set forth herein in full.

After exposure to the light source 2328, the pathogen reduced plasma may be directed to the containers 2320 (by pump 2316) for later lyophilization. Any suitable container for holding the pathogen reduced plasma may be used as container 2320. In embodiments, the containers may be similar to container 1200 (FIGS. 12-13), 1600 (FIGS. 16C-17), 1800 (FIG. 18), 1900 (FIG. 19), and/or 2000 (FIG. 20).

Figure 24:
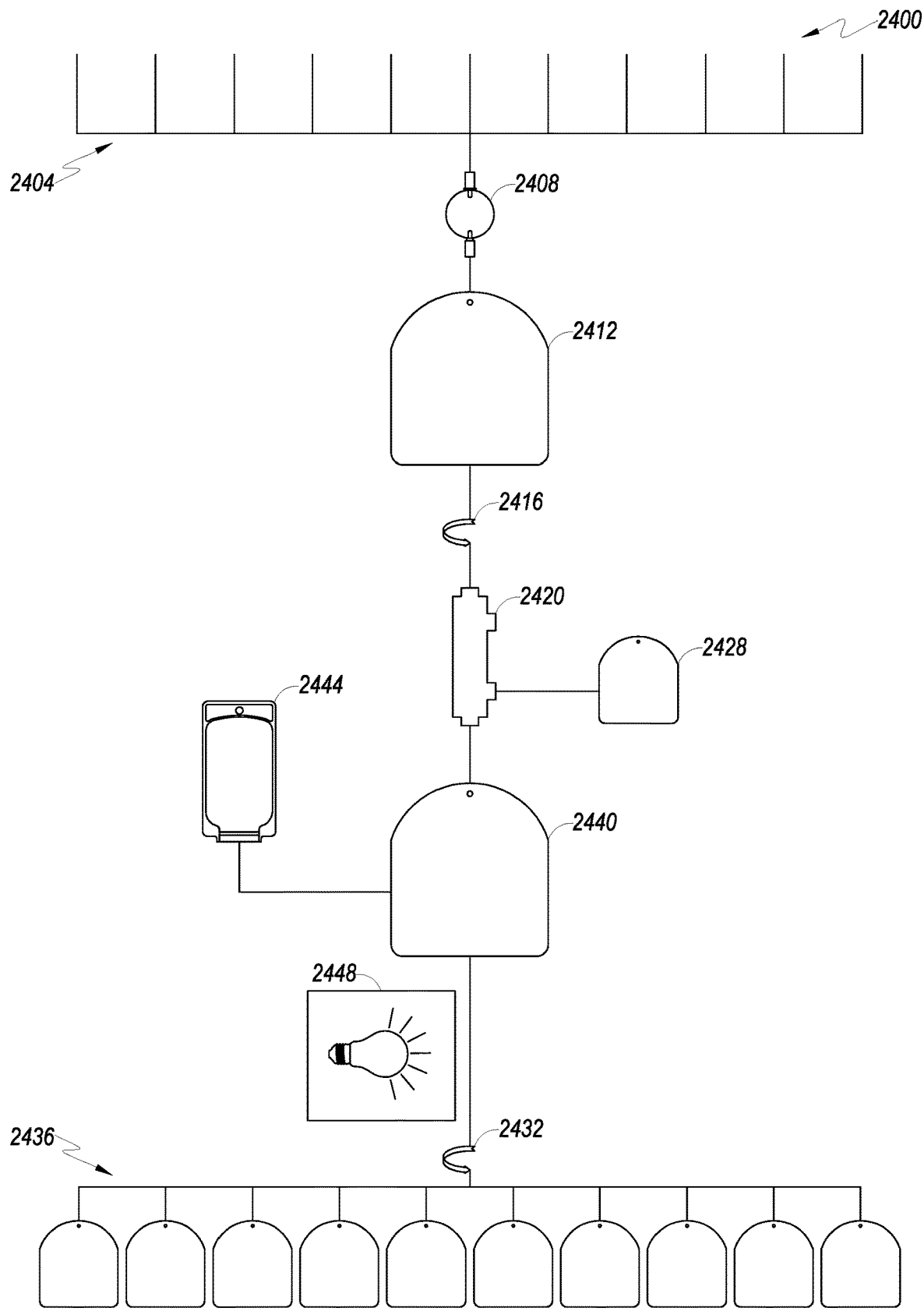
FIG. 24 illustrates an embodiment of a system for pooling a biological fluid, reducing a volume of the biological fluid, pathogen reducing the reduced volume of fluid, and filling containers with the biological fluid for later lyophilizing.

FIG. 24 illustrates an embodiment of a system 2400 for filling containers with a biological fluid. System 2400 is similar to system 2200 described above, however it includes additional pathogen reduction features. In embodiments, system 2400 is used to pool blood or blood components and pathogen reduce the blood or blood components prior to lyophilizing. In one embodiment, system 2400 is used to pool and pathogen reduce human plasma.

Plasma flows from ports 2404 through filter 2408, which is similar to filter 2208 and may be used to remove some components or contaminants from the plasma, e.g., cells such as leukocytes. In other embodiments, system 2400 may include a series of filters each for filtering the same, or a different, component or contaminant from the plasma.

After filtering, the plasma is pooled together in container 2412, which in embodiments is a bag. System 2400 may include additional components that effect agitation of the plasma, not limiting examples including, rollers, motors, ultrasonic transducers, power source(s), etc.

System 2400 also includes pump 2416, which is used to move plasma from container 2412 into filter 2420. It is noted that in other embodiments, pumps may be used in other parts of the system, for example, a pump may be used to move plasma from filter 2408 to container 2412.

Filter 2420 may be used to concentrate the plasma by removing water and some salt from the plasma. In one embodiment, filter 2420 may be a hollow fiber membrane filter, which removes water, salt, and some lower molecular weight molecules from the plasma. The water, salt, and molecules from filter 2420 may be collected in container 2428, where they may be stored for later use, or discarded. Although system 2400 illustrates only a single filter 2420, in other embodiments, system 2400 may include a series of filters each removing at least some water or other component from the plasma.

Pump 2432 is used to move plasma from filter 2420 into container 2440. After the plasma is moved into container 2440, a photosensitizer stored in container 2244 may be mixed into the plasma in container 2440. System 2400 may include additional components that effect agitation of the plasma and photosensitizer, not limiting examples including, rollers, motors, ultrasonic transducers, power source(s), etc.

Container 2440 may be made from materials that are transparent or at least translucent to the wavelength of light used in the pathogen reduction process. In some embodiments, container 2440 may be made of flexible polymeric materials that are transparent or at least translucent to light of wavelengths between about 275 nm to about 625 nm.

After the photosensitizer has been mixed into the plasma in container 2440, the plasma may be exposed to a light source such as light source 2448. In embodiments, light source 2448 may be of a wavelength that interacts with the photosensitizer to pathogen reduce the plasma. Examples and further description of pathogen reduction, which may be used in embodiments, including combinations of light wavelengths and photosensitizers, are provided in U.S. Pat. Nos. 6,548,241; 6,258,577; and 6,277,337, which are all hereby incorporated by reference in their entirety as if set forth herein in full.

After exposure to the light source 2448, the pathogen reduced plasma may be pumped by pump 2432 to the containers 2436 for later lyophilization. Any suitable container for holding the pathogen reduced plasma may be used as containers 2436. In embodiments, the containers may be similar to container 1200 (FIGS. 12-13), 1600 (FIGS. 16-17C), 1800 (FIG. 18), 1900 (FIG. 19), and/or 2000 (FIG. 20).

Figure 25:
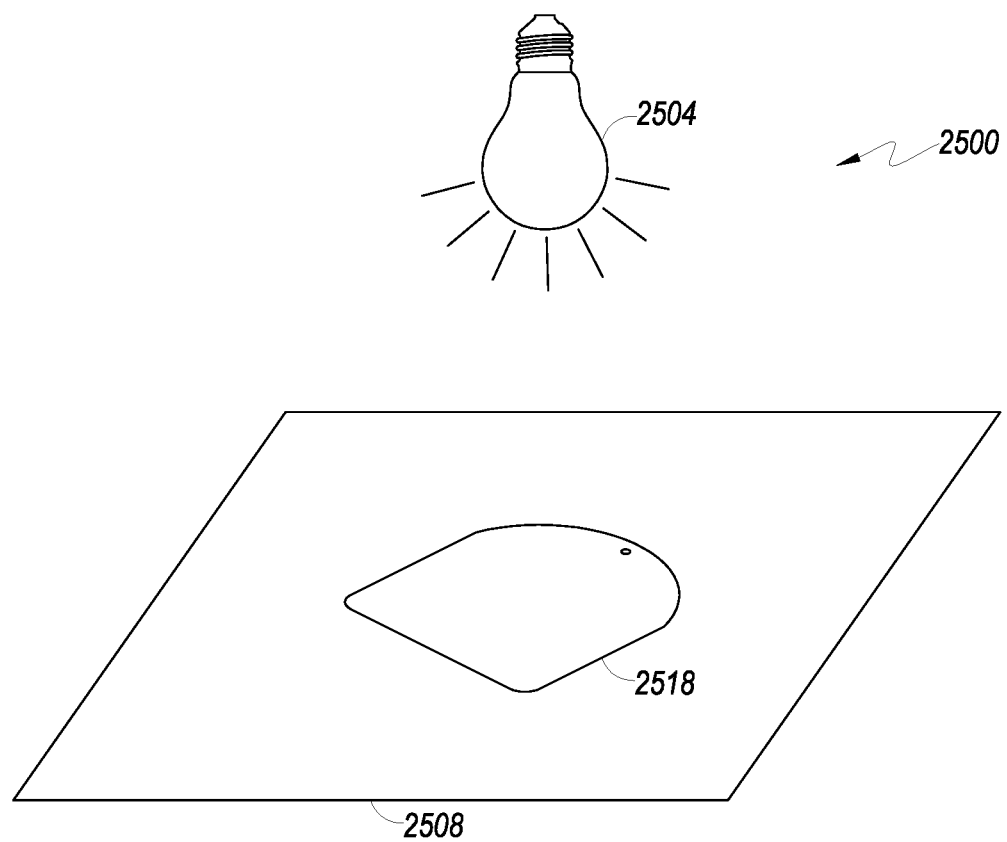
FIG. 25 depicts a bag containing fluid for treatment, and a shaker table for agitating the fluid while exposing the fluid to photoradiation from a light source in accordance with embodiments.

In systems 2300 and 2400, the light sources (2328 and 2448) may include additional components and features in addition to a light source. For example, in FIG. 25, a system 2500 is shown that may be used as light sources 2328 (FIG. 23) and/or 2448 (FIG. 24). As shown in FIG. 25, system 2500 includes a light source 2504, as well as an agitator 2508 (e.g., shaker table) for agitating the fluid in container 2518 (in embodiments containers 2312 or 2440) while exposing the fluid to light source 2504.

Figure 26:
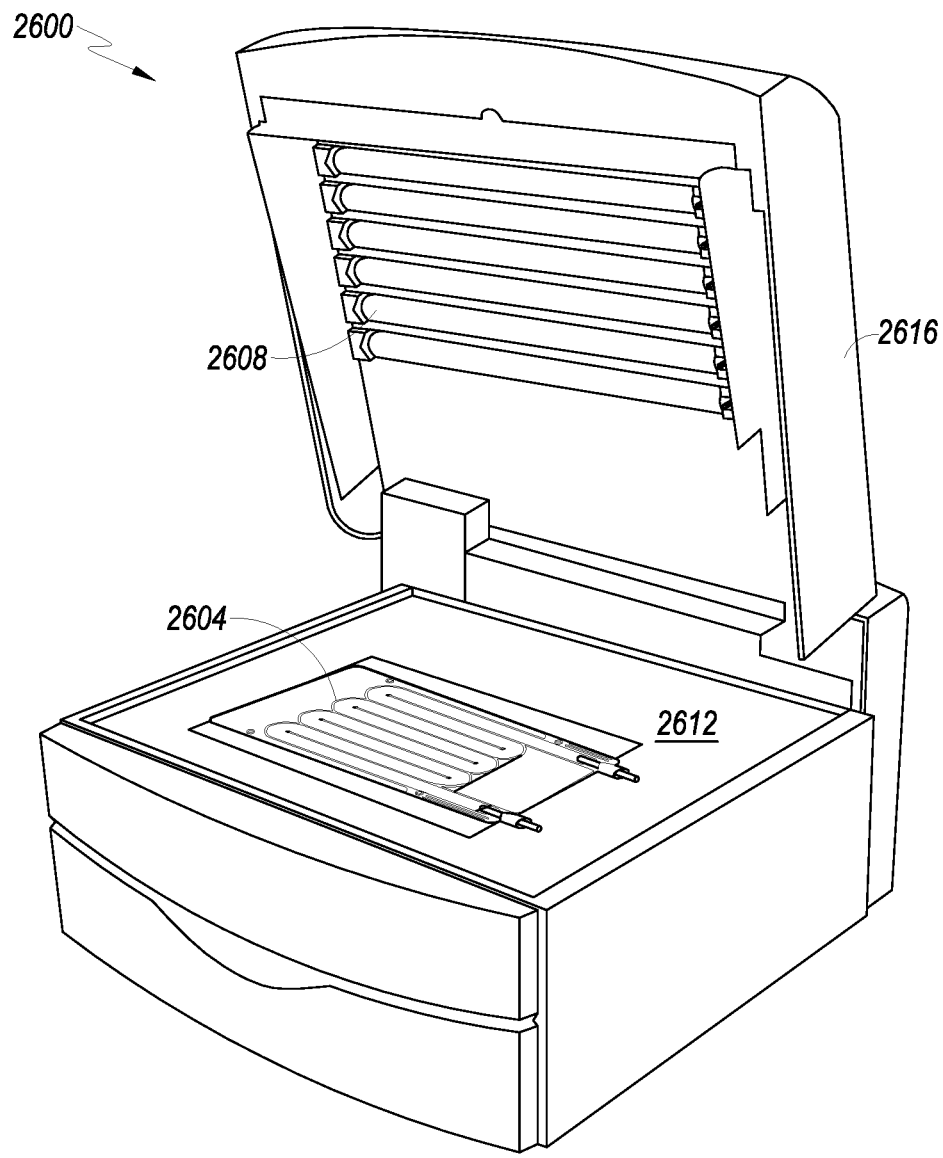
FIG. 26 illustrates an apparatus for reducing or inactivating pathogens and microorganisms in accordance with embodiments.

FIG. 26 illustrates another example embodiment of an apparatus 2600, e.g., a pathogen reduction apparatus that may be used as part of light sources (2328 and 2448). As illustrated in FIG. 26, apparatus 2600 includes a light source 2608 on a door 2616 that opens and closes. When door 2616 is opened, a container with fluid may be placed on a table 2612, which in embodiments has a window where a second light source 2604 is positioned to expose the fluid in the container to the light source 2604. Door 2616 can be closed and the fluid in the container can be exposed to both light sources 2604 and 2608. In embodiments, table 2612 may shake to agitate the fluid in the container before, after, or during exposure to light sources 2604 and 2608

In some embodiments, systems (or portions of the systems) 2100, 2200, 2300, and 2400 may be implemented as disposable sets that interface with some permanent components of the systems, e.g., light sources. For example, in some embodiments, ports, filters, containers, may be manufactured as a disposable set, with tubing connecting the various components of the system. Permanent components, such as pumps and/or light sources may interface with the disposable components.

Figure 27:
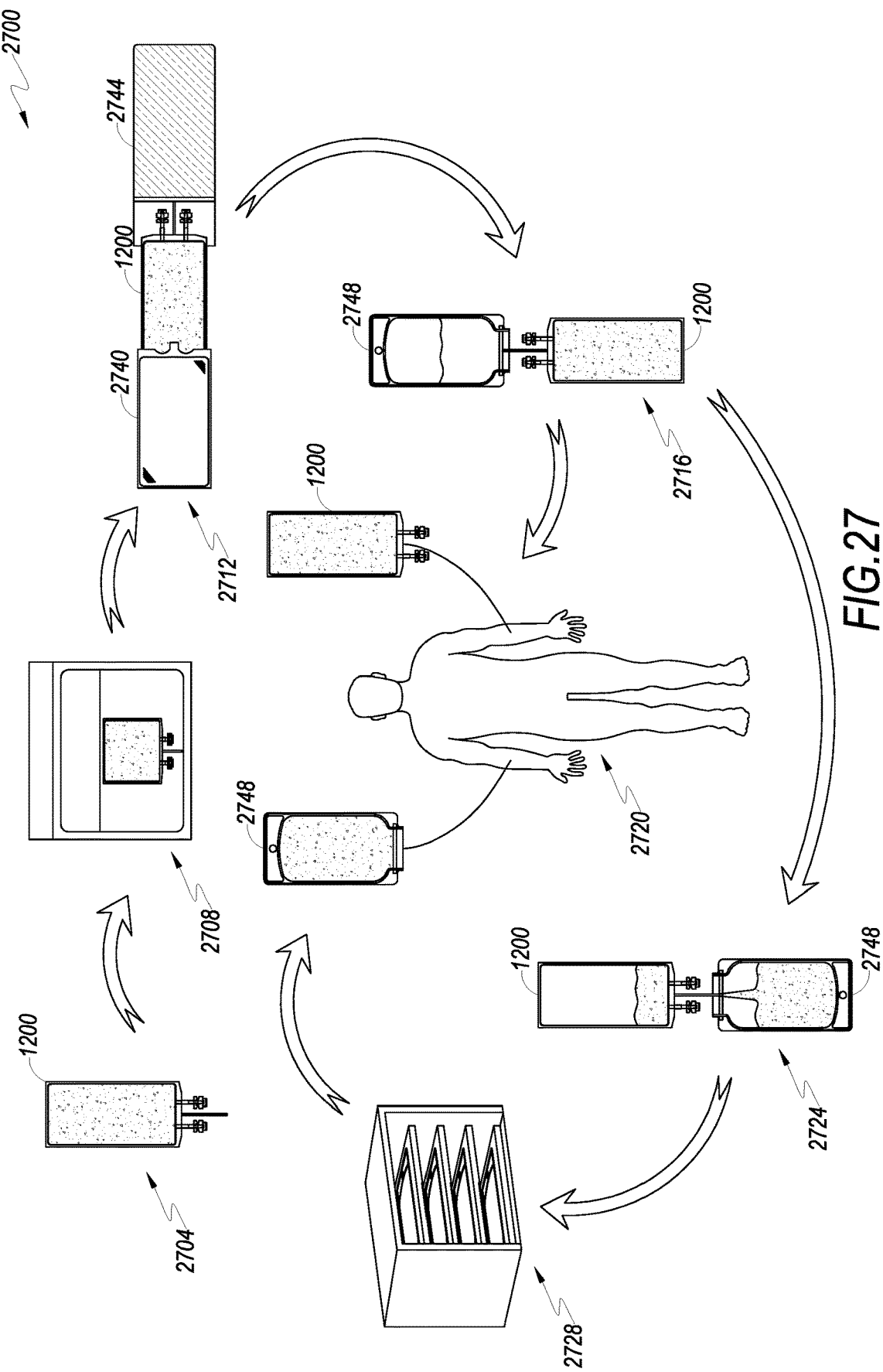
FIG. 27 illustrates a process for lyophilizing, storing, reconstituting, storing, and transfusing a blood component according to an embodiment.

FIG. 27 illustrates a process 2700 for lyophilizing, storing, reconstituting, storing, and transfusing a biological fluid, which in FIG. 27 may be plasma. The process 2700 may be performed using a suitable container, such as a bag with features described above with respect to containers 1200 (FIGS. 12 and 13), 1600 (FIG. 16-17C), 1800 (FIG. 18), 1900 (FIG. 19), and 2000 (FIG. 20). The description below is directed to the processing of plasma using a container referenced below as bag 1200; however, other embodiments are not limited thereto.

At 2704, bag 1200 is filled with plasma. In embodiments, the bag 1200 may be filled using a system for pooling plasma, such as systems 2100, 2200, 2300, and/or 2400. At 2708, the plasma in bag 1200 is lyophilized in bag 1200 using an apparatus which may include one or more features of plate structures 800 (FIG. 8), 900 (FIG. 9), and/or 1000 (FIG. 10). The lyophilization process may involve steps as described below with respect to flow diagram 2800, including without limitation, evaporating liquid from the plasma while subjecting the plasma to a first pressure (e.g., below atmospheric pressure), pressing the remaining plasma while freezing to create a frozen plasma, and sublimating a portion of the frozen plasma while subjecting the plasma to a second pressure.

It is noted that although FIG. 27 illustrates the use of a container such as container 1200, in other embodiments a different container may be used. As one example, containers such as 1600 (FIGS. 16 and 17C), 1800 (FIG. 18), 1900 (FIG. 19), and/or 2000 (FIG. 20) may be used. In these embodiments, one chamber (or portion) of the container may be used for the lyophilization of the plasma. After the lyophilization, the lyophilized plasma may be moved to a second chamber, or portion, of the container and the first chamber (or portion) then separated from the first portion.

At 2712, bag 1200, with the lyophilized plasma, is packaged for storage. The packaging may involve a number of different steps and utilize different packaging materials. In process 2700, a sleeve 2740 is placed over bag 1200 to provide additional robustness and is generally kept on bag 1200 during subsequent process steps. The sleeve 2740 may be made from any suitable material such as a polymer. In embodiments, sleeve 2740 may be made from a transparent or translucent polymer that is flexible, such as polycarbonate, acrylic, polystyrene, polysulfone, polyethylene, polyolefin, polypropylene, polyvinylchloride, or combinations thereof.

The bag 1200 and sleeve 2740 may also be placed in a foil bag 2744. The foil bag 2744 provides additional protection that may prolong the viability of the lyophilized plasma in bag 1200. The foil bag 2744 with its metalized layer may block light, be water proof, may include a water vapor desiccant, and be vacuum packed, in order to extend the shelf life of the lyophilized plasma. The use of a flexible bag 1200, flexible sleeve 2740, and flexible foil bag 2744 provides a flexible product that can be easily stored and transported, such as in a back pack. In embodiments, the lyophilization of the plasma along with the packaging may allow the plasma to have a shelf life of at least two years.

A bag 2748, which includes reconstitution fluid, may be packaged in foil bag 2744 with the bag 1200. When needed, the lyophilized plasma in bag 1200 may be reconstituted using the fluid in bag 2748, see step 2716 in FIG. 27. Bag 2748 may be connected to bag 1200 to allow the reconstitution fluid to flow into bag 1200. After a short time (e.g., two minutes or less), and in some embodiments some agitation, the reconstituted plasma is ready to be infused into a patient at 2720.

In other embodiments, at 2724, the reconstituted plasma may be moved into bag 2748 for additional storage at step 2728. In these embodiments, bag 2748 may include features, such as materials that allow liquids to be stored for some period of time. In some embodiments, the lyophilization of the plasma and the use of bag 2748 allow the reconstituted plasma to be stored for at least a day before being infused into a patient at 2720 from bag 2748.

Figure 28:
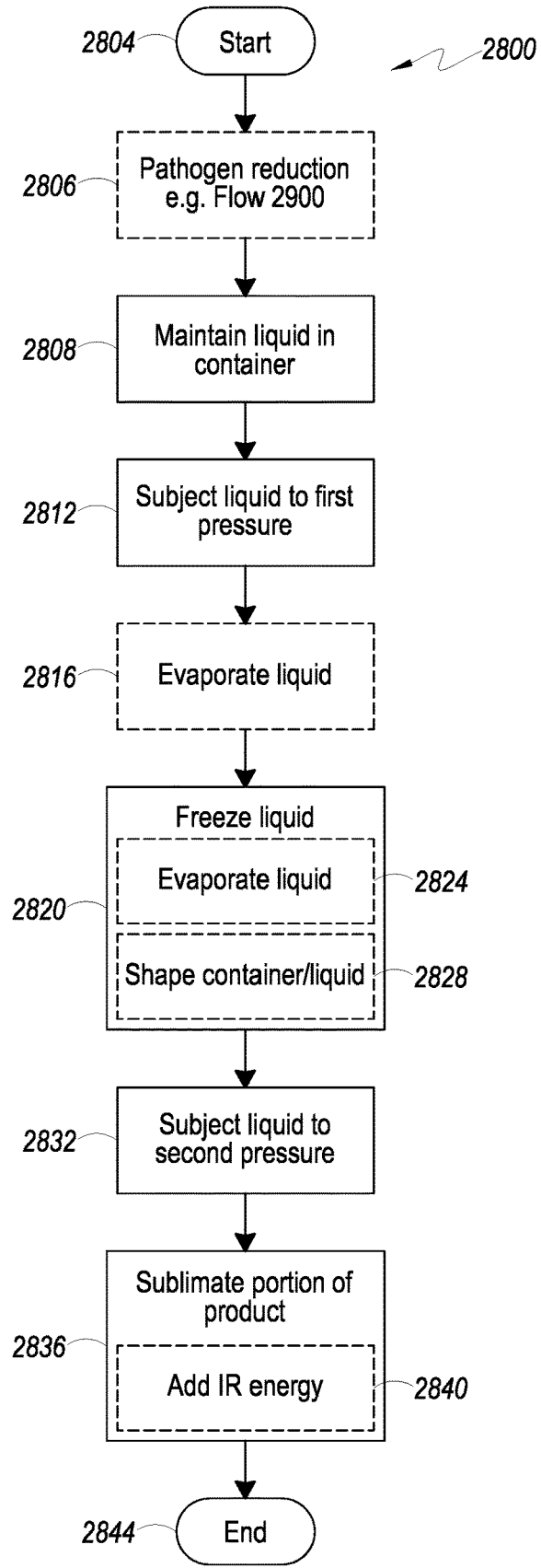
FIG. 28 illustrates a flow chart of a process of lyophilizing material according to an embodiment.

Referring now to FIG. 28, a flow chart 2800 is illustrated for a process of lyophilizing material according to an embodiment. Although specific devices may be described below for performing steps in flow chart 2800, embodiments are not limited thereto. For example, some steps may be described as performed by a processor, while others are performed by one or more features of a lyophilization apparatus. This is done merely for illustrative purposes, and flow chart 2800 is not limited to being performed by any specific device, feature, or component. In embodiments, flow chart 2800 may be implemented by a lyophilization apparatus, such as apparatus 100 or 200, with features of one or more plate structures 800, 900, or 1000 described above with respect to FIGS. 8, 9, and 10.

Furthermore, any material may be lyophilized using the process illustrated in flow chart 2800 including biological liquids such as blood and blood components. In one specific embodiment, plasma is lyophilized using the process illustrated in FIG. 28; however this is merely one example. The description of flow chart 2800 is made with respect to a biological liquid, e.g., plasma, but this is done merely for purposes of illustration and is not intended to limit the application of flow chart 2800 to lyophilize other materials.

Flow 2800 starts at 2804. Flow 2800 may in embodiments include optional pathogen reduction step or steps 2806. One embodiment of a pathogen reduction process is described below with respect to FIG. 29 and flow 2900.

After the optional pathogen reduction process (step 2806), a liquid (or other material to be lyophilized) is maintained within a container at step 2808. In embodiments, the container is designed to be used to store the liquid prior to lyophilization, in the lyophilization, to store the lyophilized material for a relatively long period of time, to reconstitute the lyophilized material, and in some embodiments to infuse the reconstituted material into a patient. In one embodiment, the container may include one or more features described above with respect to container 1200. In other embodiments, containers 1600, 1800, 1900, or 2000 may be used where one chamber (or portion) of the container is used for lyophilization and another chamber (or portion) is used to store the lyophilized material. In embodiments, step 2808 may include sub-steps such as placing the container on a shelf within a lyophilization apparatus such as apparatus 100 or 200.

Returning to flow 2800, from 2808 flow passes to 2812 where the container and liquid is subjected to a first pressure. In embodiments, the pressure is created by a lyophilization apparatus. The first pressure may be below atmospheric pressure and may depend on the specific material (e.g., liquid) being lyophilized. In embodiments where the plasma includes water, the first pressure may be less than about 100 Torr absolute pressure, less than about 75 Torr, less than about 50 Torr, and even less than about 25 Torr. In other embodiments, the first pressure may be greater than about $5 \times 10^{-2}$ Torr, greater than about $1 \times 10^{-1}$ Torr, greater than about $5 \times 10^{-1}$ Torr, greater than about 1 Torr, greater than about 1 Torr, greater than about 5 Torr, or even greater than about 10 Torr. In yet other embodiments, the first pressure may range from about 40 Torr to about 0 Torr, from about 30 Torr to about 1 Torr, from about 20 to about 2 Torr, or even from about 15 Torr to about 3 Torr. These are merely some examples of ranges of the first pressure and other embodiments may utilize different pressures.

From step 2812, flow passes to optional step 2816 where liquid from the material being lyophilized may be evaporated. In some embodiments, such as when the material is plasma, the liquid being evaporated may be water. Because the material is below atmospheric pressure, only a relatively small amount of energy may be required to evaporate liquid from the material. The energy may be supplied for example by a thermal fluid circulating through a plate of the shelf or by an IR radiator that is part of the shelf in a lyophilization apparatus.

Step 2816 may be performed in some embodiments to reduce the volume of the liquid to be lyophilized. Without being bound by theory, it is believed that by performing step 2816 to reduce the volume of the liquid, a subsequent sublimation step may be performed more quickly and/or efficiently.

Step 2820 follows step 2816. At step 2820, the liquid is cooled to freeze liquid into a solid and create a frozen product. In embodiments, a thermal fluid circulating through a plate of the shelf may remove energy and cool the liquid to freeze the liquid into a solid. In some embodiments, step 2820 may involve a number of optional sub-steps. For example, sub-step 2824 may involve evaporating a portion of the liquid. The evaporation may cool the liquid to an extent that it freezes into a solid. In some embodiments, sub-step 2824 may be performed as part of step 2816 described above.

Additionally, in some embodiments, sub-step 2828 may be performed to shape, e.g. by pressing the container and the liquid within the container. Without being bound by theory, it is believed that pressing (or otherwise shaping) the container and the liquid (or other material) in the container, as part of the freezing step 2820, may create a more uniform cross-section when the liquid (or other material) is cooled and frozen. Accordingly, it is believed that the more uniform cross-section will increase the efficiency of removing a component, such as ice, from the frozen product during a subsequent sublimation step. In other words, reducing variations in thickness may allow sublimation to occur at a similar rate throughout the material improving the efficiency of the process.

In some embodiments, the pressure may be applied using a shelf system 300 or 500 such as described above with respect to FIGS. 3-6. In other embodiments, the pressure for pressing the material may be provided using a different system, such as a flexible balloon or bladder that may be filled with a fluid. The balloon or bladder may be positioned above the material to be lyophilized. The balloon or bladder may be filled with a fluid (e.g., gas or liquid) which cause the balloon or bladder to expand and press the liquid during freezing. This is merely one alternative, and any way for applying some pressure on the container, and the liquid, may be utilized with other embodiments to shape the container and/or material (e.g., liquid).

At step 2832, the container and the frozen product is subjected to a second pressure. In embodiments, the pressure is created by the lyophilization apparatus. The second pressure may be below atmospheric pressure and below the first pressure. The specific pressure may depend on the specific material being lyophilized. In embodiments where the material may include water, the second pressure may be less than about $5 \times 10^{-1}$ Torr, less than about $1 \times 10^{-1}$ Torr, less than about $5 \times 10^{-2}$ Torr, or even less than less than about $1 \times 10^{-2}$ Torr. In other embodiments, the second pressure may be greater than about $1 \times 10^{-4}$ Torr, greater than about $5 \times 10^{-4}$ Torr, greater than about $1 \times 10^{-3}$ Torr, greater than about $5 \times 10^{-3}$ Torr, or even greater than about $1 \times 10^{-2}$ Torr. These are merely some examples of ranges of the second pressure and other embodiments may utilize different pressures.

After step 2832, a portion of the frozen product, e.g., the solid created at step 2820 from remaining liquid, may be sublimated at step 2836. Energy may be required to sublimate material from the frozen product. The energy may be supplied for example by a thermal fluid circulating through a plate of the shelf. In some embodiments, step 2832 may involve a sub-step 2840 of adding infrared energy using an IR radiator that may be part of the shelf in the lyophilization apparatus. In embodiments where the shelf includes a plate structure similar to structures 800 or 900, the IR energy may be added from the top, while thermal energy from a thermal fluid may be added from the bottom. Flow then ends at 2844.

Although flow 2800 has been described with steps listed in a particular order, the present disclosure is not limited thereto. In other embodiments, steps may be performed in different order, in parallel, or any different number of times, e.g., before and after another step. Also, as indicated above, flow 2800 includes some optional steps/sub-steps. However, those steps above that are not indicated as optional should not be considered as essential to the invention, but may be performed in some embodiments of the present invention and not in others.

In some embodiments, portions of flow 2800 may be performed as part of a customized lyophilization process run on a lyophilization apparatus or system. For example, an operator may utilize an application running on a computer system (e.g. computer system described 3300 below) to create custom processes that may include one or more steps of flow 2800. The processes may then be run in a lyophilization apparatus or system to lyophilize material. In some embodiments, once created, the custom processes may be run by simply pressing a button.

Figure 29:
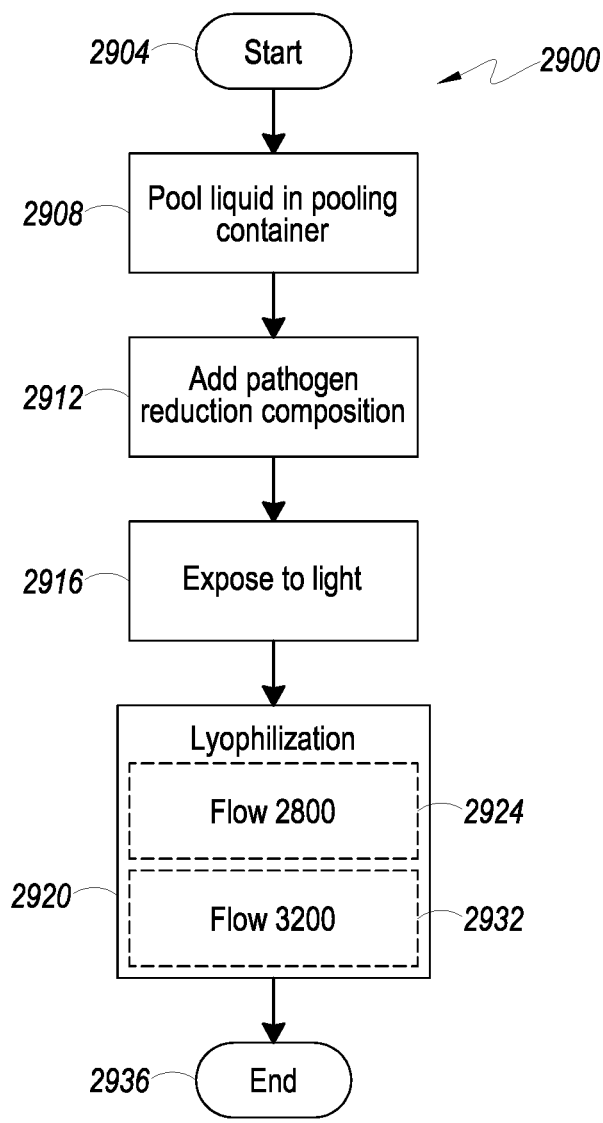
FIG. 29 illustrates a flow chart of a process for pathogen reducing and lyophilizing material according to an embodiment.

FIG. 29 illustrates a flow chart 2900 for a process of lyophilizing material according to another embodiment. Although specific devices may be described below for performing steps in flow chart 2900, embodiments are not limited thereto. For example, some steps may be described as performed by a pathogen reduction apparatus, while others are performed by one or more features of a lyophilization apparatus. This is done merely for illustrative purposes, and flow chart 2900 is not limited to being performed by any specific device, feature, or component. In embodiments, flow chart 2900 may be implemented by a lyophilization apparatus, such as apparatus 100 or 200.

Furthermore, any material may be lyophilized using the process illustrated in flow chart 2900 including biological liquids such as blood and blood components. In one specific embodiment, plasma is lyophilized using the process illustrated in FIG. 29; however this is merely one example. The description of flow chart 2900 is made with respect to a biological liquid, e.g., plasma, but this is done merely for purposes of illustration and is not intended to limit the application of flow chart 2900 to lyophilize other materials.

Flow 2900 starts at 2904 and passes to step 2908 where liquid is pooled in a container. In embodiments, systems such as systems 2400 and 2500 may be used to pool a number of units of e.g., plasma, into a larger container. Also, in embodiments step 2908 may involve agitating the liquid being pooled in the container to effect mixing of the pooled liquid. The agitation may involve the use of mechanisms to agitate the liquid, some non-limiting examples including, pumps, shakers, aerators, rollers, motors, ultrasonic transducers, power source(s), etc.

After step 2908, flow passes to step 2912 where a pathogen reduction composition is added. In embodiments, the pathogen reduction composition may include an endogenous photosensitizer, such as a flavin, including riboflavin. In other embodiments, the pathogen reduction composition may additionally include other compositions. For example, the pathogen reduction composition may include surfactants, buffers, salts, pH modifiers, solvents, etc.

At step 2916, the liquid with the pathogen reduction composition is exposed to light. Step 2916 may involve the use of any suitable system that provides a light source that exposes the liquid, with the pathogen reduction composition, to the necessary wavelength of light to reduce pathogens in the liquid. In embodiments, a system such as system 2500 may be used to both agitate and expose the liquid to a light source. In other embodiments, a pathogen reduction apparatus such as apparatus 2600 illustrated in FIG. 26 may be used to both agitate the liquid, as well as expose the liquid to a light source. The agitation may involve the use of mechanisms to agitate the liquid, some non-limiting examples including, pumps, shakers, aerators, rollers, motors, ultrasonic transducers, power source(s), etc.

After step 2916, the liquid may be lyophilized using any suitable lyophilization process 2920. For example, in some embodiments, flow 2900 may pass to flow 2800 described above where the liquid, which has been pathogen reduced, is lyophilized. In other embodiments, the lyophilization process may involve flow 3200 discussed below with respect to FIG. 32. Flow 2900 then ends at 2936.

Figure 30:
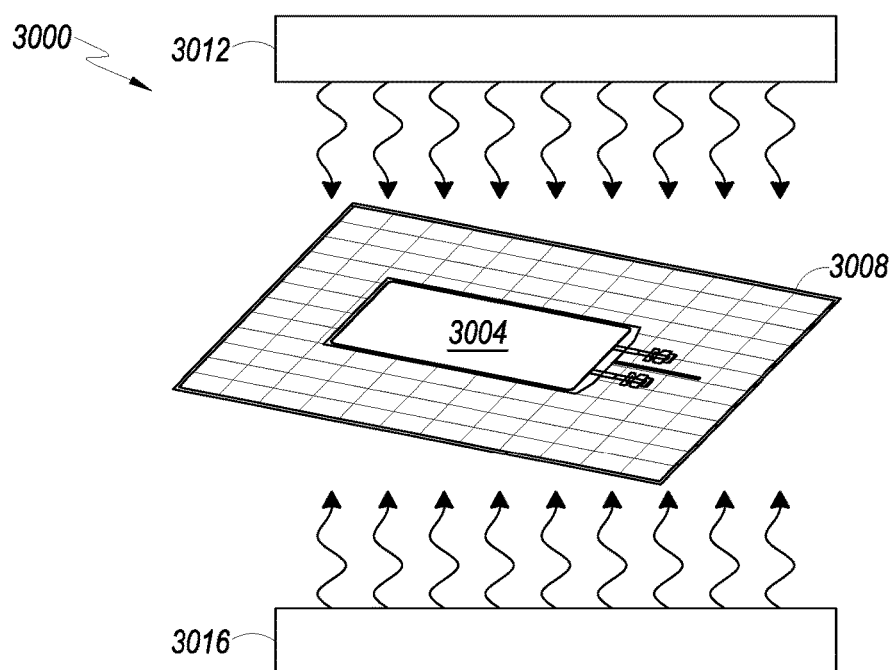
FIG. 30 illustrates an embodiment of system for lyophilizing material using IR radiation.
Figure 31:
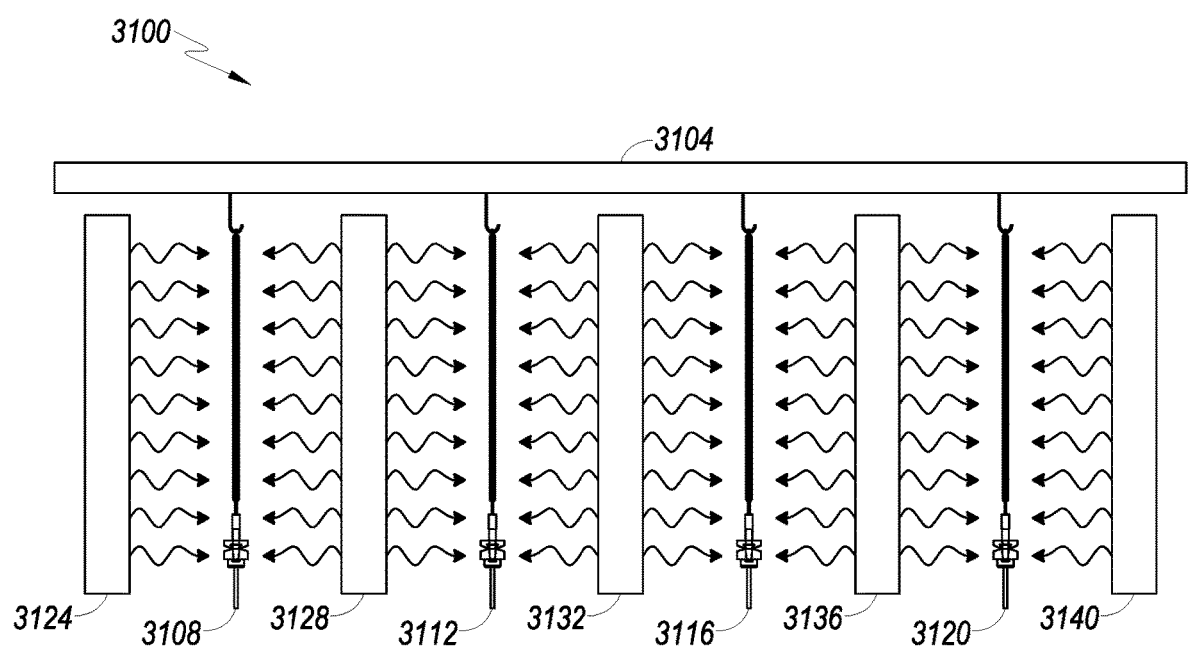
FIG. 31 illustrates another embodiment of system for lyophilizing material using IR radiation.

FIGS. 30 and 31 illustrate embodiments of systems for lyophilizing material by using primarily IR (infrared) energy. As discussed above with respect to plate structures 800, 900, 1000, and flow 2800 (FIG. 28), the present invention provides for lyophilization processes that may involve the use of IR energy in addition, or in lieu of, thermal energy. Systems 3000 (FIG. 30) and 3100 (FIG. 31) are examples of systems that may be used in embodiments that utilize primarily IR energy in the sublimation step of a lyophilization process. Accordingly, the description below assumes that the material has been frozen using other features of system 3000 or system 3100, or the material may have been frozen in a different system or apparatus (e.g., systems 100 and 200 using plate structures 800, 900 and/or 1000).

FIG. 30 illustrates a system 3000 for sublimating a material in container 3004 as part of a lyophilization process. In some embodiments, container 3004 may include two walls attached to define an interior volume where material to be lyophilized may be placed. The materials that may be used for the walls of container 3004 may be made from materials that have relatively high permeability to a gas, such as water vapor, but are still robust enough to hold the material without leaking. In some embodiments, the walls of container 3004 may be made from one or more of the following materials: flashspun high-density polyethylene (HDPE), polytetrafluoroethylene (PTFE), acrylics cast on woven or nonwoven textiles, amides cast on woven or nonwoven textiles, and/or combinations thereof.

Container 3004, with frozen material inside, is place on a shelf 3008 that is designed to allow gas that is transported through container 3004 to dissipate. In embodiments, shelf 3008 may simply include some perforations that allow gas to flow away from container 3004. In other embodiments, shelf 3008 may be made from a screen or other porous structure that allows gas to dissipate away from container 3004.

In addition, system 3000 includes IR radiators 3012 and 3016. As shown in FIG. 30, the IR radiators 3012 and 3016 are positioned so that they radiate IR energy to both sides of container 3004. As previously noted, sublimation may occur at a surface of a material. Using the design shown in FIG. 30, two surfaces may be subjected to sublimation at the same time, which may reduce the overall lyophilization time of the material.

FIG. 31 illustrates another embodiment of a system 3100 for sublimating material in containers (3108, 3112, 3116, and 3120) as part of a lyophilization process. Similar to container 3004, containers 3108, 3112, 3116, and 3120 may include two walls attached to define an interior volume where material to be lyophilized may be placed in the interior volume. The materials that may be used for the walls of the containers 3108, 3112, 3116, and 3120 may be made from materials that have relatively high permeability to a gas, such as water vapor, but are still robust enough to hold the material without leaking. In some embodiments, the walls of containers 3108, 3112, 3116, and 3120 may be made from one or more of the following materials: flashspun high-density polyethylene (HDPE), polytetrafluoroethylene (PTFE), acrylics cast on woven or nonwoven textiles, amides cast on woven or nonwoven textiles, and/or combinations thereof.

System 3100 includes a hanger 3104 from which the containers 3108, 3112, 3116, and 3120 with frozen material inside, may be hung. Hanger 3104 may be designed with various hooks or other features for holding containers 3108, 3112, 3116, and 3120 vertically.

System 3100 includes IR radiators 3124, 3128, 3132, 3136, and 3140. As shown in FIG. 31, the IR radiators 3124, 3128, 3132, 3136, and 3140 are positioned so that they radiate IR energy to both sides of containers 3108, 3112, 3116, and 3120. As previously noted, sublimation may occur at a surface of a material. Using the design shown in FIG. 31, two surfaces may be subjected to sublimation at the same time, which may reduce the overall lyophilization time of the material.

Figure 32:
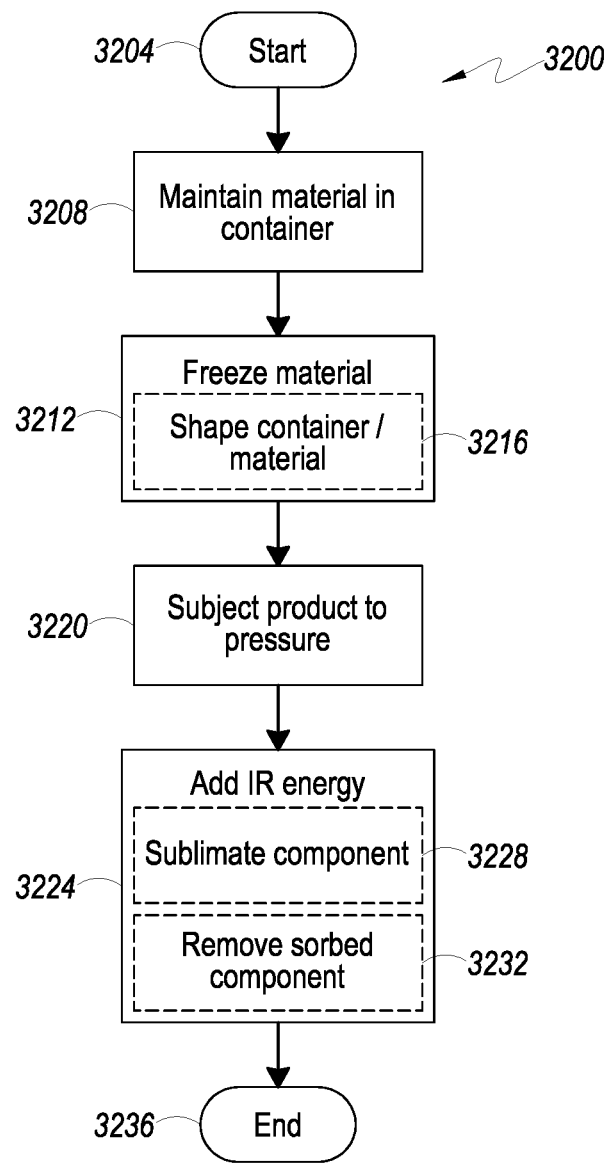
FIG. 32 illustrates a flow chart of a process of lyophilizing material using IR radiation according to an embodiment.

FIG. 32 illustrates a flow chart 3200 for a process of lyophilizing material according to an embodiment. Although specific devices may be described below for performing steps in flow chart 3200, embodiments are not limited thereto.

Flow 3200 starts at 3204 and passes to step 3208 where material is maintained in a container. The material may be in some embodiments a liquid, such as blood or blood components. In one specific embodiment, the material is human plasma. The container where the material is stored may in embodiments include walls with materials that have relatively high permeability to a gas, such as water vapor, but are still robust enough to hold the material during processing. Non-limiting examples of materials that may be used include: flashspun high-density polyethylene (HDPE), polytetrafluoroethylene (PTFE), acrylics cast on woven or nonwoven textiles, amides cast on woven or nonwoven textiles, and/or combinations thereof.

Step 3208 may in embodiments involve moving material from one container to another. For example, in the embodiment of human plasma, step 3208 may involve pooling a number of units of plasma and transferring volumes of plasma into containers and maintaining the plasma in the containers.

After step 3208, flow 3200 passes to step 3212 where the material is frozen. In some embodiments step 3212 may involve the use of shelves with plate structures that may include features of plate structures 800 (FIGS. 8A-8B), 900 (FIG. 9), or 1000 (FIG. 10). For example, step 3208 may involve placing the container on a shelf that includes pathways for circulating a thermal fluid that cools the material and freezes any liquid in the material at step 3212.

Step 3212 may involve a number of other sub-steps. For example, in one embodiment, step 3212 involves sub-step 3216 where the container and material are shaped, e.g., pressed during freezing. The shaping may be performed using one or more shelf systems such as systems 300 (FIG. 3) or 500 (FIG. 5), which may use plate structures 800 (FIGS. 8A-8B), 900 (FIG. 9), and/or 1000 (FIG. 10). In other embodiments, step 3212 may involve other steps or structures (e.g., forms, textures, stamps, etc.) for shaping the material during the freezing.

Flow 3200 passes from step 3212 to step 3220 where the material is subjected to a pressure that is below atmospheric pressure. The pressure may depend on the specific material being lyophilized. In embodiments where the material may include water, the pressure may be less than about $5 \times 10^{-1}$ Torr, less than about $1 \times 10^{-1}$ Torr, less than about $5 \times 10^{-2}$ Torr, or even less than less than about $1 \times 10^{-2}$ Torr. In other embodiments, the second pressure may be greater than about $1 \times 10^{-4}$ Torr, greater than about $5 \times 10^{-4}$ Torr, greater than about $1 \times 10^{-3}$ Torr, greater than about $5 \times 10^{-3}$ Torr, or even greater than about $1 \times 10^{-2}$ Torr. These are merely some examples of ranges of the second pressure and other embodiments may utilize different pressure ranges. Step 3220 may be performed in some embodiments using lyophilization apparatuses such as apparatuses 100 (FIG. 1) and/or 200 (FIG. 2).

From 3220, flow passes to step 3224, where IR energy is added to the material. Step 3224 may involve in embodiments adding IR energy to only one side of the container. In other embodiments, step 3224 may involve adding IR energy to two or more sides of a container. Step 3224 may be performed in systems that provide IR energy some non-limiting examples including systems 3000 (FIG. 30) and/or 3100 (FIG. 31). Other examples of structures that may be used to add IR energy include plate structures 800 (FIGS. 8A-8B), 900 (FIG. 9), or 1000 (FIG. 10).

As part of step 3224, IR energy may be provided to effect changes in the material. For example, IR energy may be provided to sublimate a component 3228 of the material, e.g., ice. Additional IR energy may be provided to not only sublimate a component, but also to remove a component that may be absorbed or adsorbed in the material (step 3232), e.g., water of hydration. Flow 3200 ends at 3236.

Figure 33:
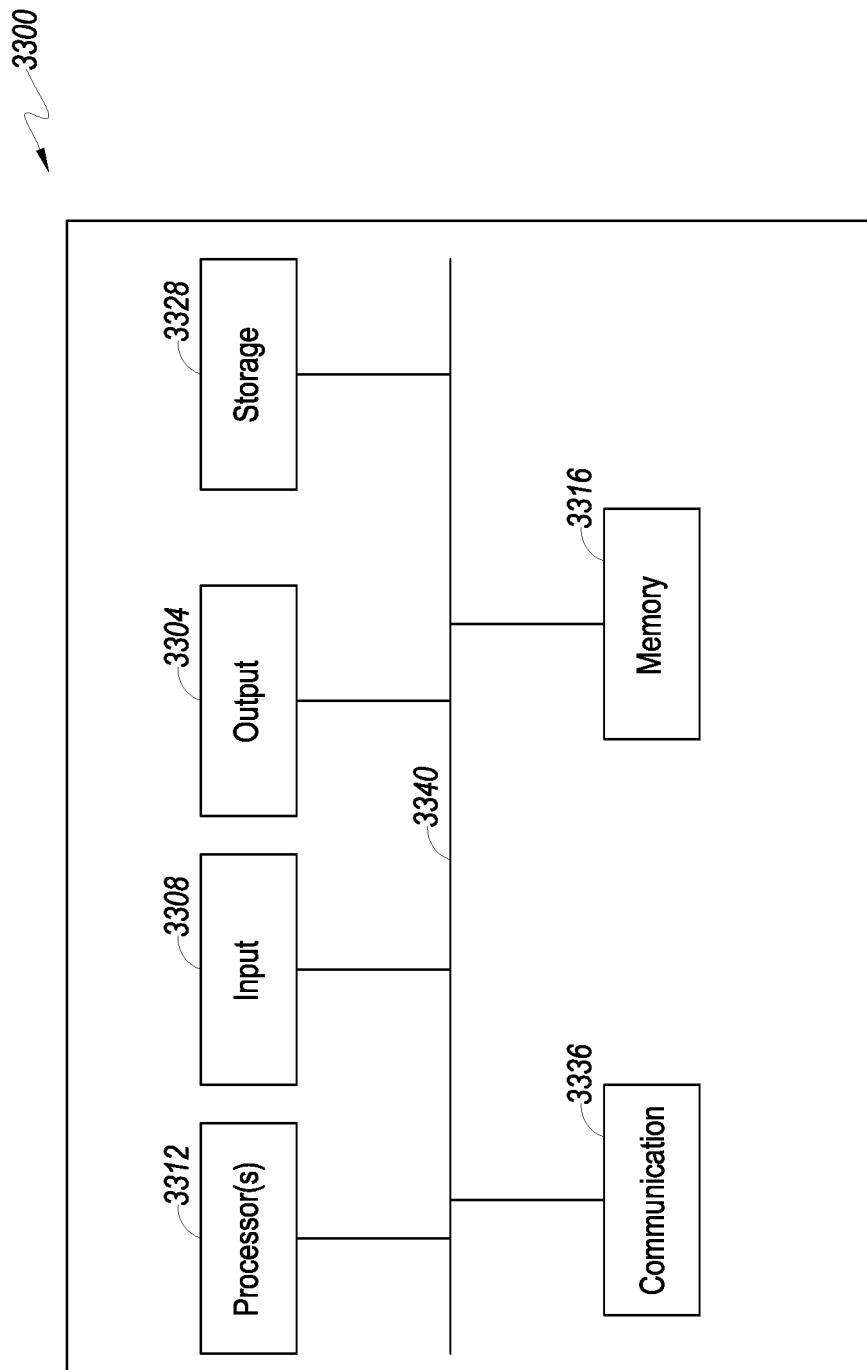
FIG. 33 illustrates an embodiment of a computer system that may be used to implement embodiments.

FIG. 33 illustrates example components of a basic computer system 3300 upon which embodiments of the present invention may be implemented. For example, systems 100 (FIG. 1) or 200 (FIG. 2) may incorporate features of the basic computer system 3300 shown in FIG. 33. Computer system 3300 includes output device(s) 3304, and input device(s) 3308. Output device(s) 3304 may include, among other things, one or more displays, including CRT, LCD, and/or plasma displays. Output device(s) 3304 may also include printers, speakers etc. Input device(s) 3308 may include, without limitation, a keyboard, touch input devices, a mouse, voice input device, scanners, etc.

Basic computer system 3300 may also include one or more processor(s) 3312 and memory 3316, according to embodiments of the present invention. In embodiments, the processor(s) 3312 may be a general purpose processor(s) operable to execute processor executable instructions stored in memory 3316. Processor(s) 3312 may include a single processor or multiple processors, according to embodiments. Further, in embodiments, each processor may be a single core or a multi-core processor, having one or more cores to read and execute separate instructions. The processors may include, in embodiments, general purpose processors, application specific integrated circuits (ASICs), field programmable gate arrays (FPGAs), and other integrated circuits.

The memory 3316 may include any tangible storage medium for short-term or long-term storage of data and/or processor executable instructions. The memory 3316 may include, for example, Random Access Memory (RAM), Read-Only Memory (ROM), or Electrically Erasable Programmable Read-Only Memory (EEPROM). Other storage media may include, for example, CD-ROM, tape, digital versatile disks (DVD) or other optical storage, tape, magnetic disk storage, magnetic tape, other magnetic storage devices, etc.

Storage 3328 may be any long-term data storage device or component. Storage 3328 may include one or more of the devices described above with respect to memory 3316. Storage 3328 may be permanent or removable.

Computer system 3300 also includes communication devices 3336. Devices 3336 allow system 3300 to communicate over networks, e.g., wide area networks, local area networks, storage area networks, etc., and may include a number of devices such as modems, hubs, network interface cards, wireless network interface cards, routers, switches, bridges, gateways, wireless access points, etc.

The components of computer system 3300 are shown in FIG. 33 as connected by system bus 3340. It is noted, however, that in other embodiments, the components of system 3300 may be connected using more than a single bus.

It will be apparent to those skilled in the art that various modifications and variations can be made to the methods and structure of the present invention without departing from its scope. Thus it should be understood that the invention is not to be limited to the specific examples given. Rather, the invention is intended to cover modifications and variations within the scope of the following claims and their equivalents.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the claimed invention.

What is claimed is:

1. A method of preparing a liquid comprising a blood component for lyophilization, the method comprising:
    pooling a plurality of volumes of liquid comprising a blood component to generate a pooled volume of liquid;
    removing a portion of liquid from the pooled volume of liquid to create a reduced volume of liquid; and
    filling a plurality of containers with the reduced volume of liquid, wherein the plurality of containers comprise a wall that is permeable to water vapor.

2. The method of claim 1, further comprising reducing pathogens in the reduced volume of liquid.

3. The method of claim 2, wherein the reducing pathogens comprises:

adding a photosensitizer to the reduced volume of liquid; and exposing the photosensitizer and the reduced volume of liquid to a light source.

* * * * *